(12) United States Patent
Fu

(10) Patent No.: US 7,811,983 B2
(45) Date of Patent: *Oct. 12, 2010

(54) INCREASED T-CELL TUMOR INFILTRATION AND ERADICATION OF METASTASES BY MUTANT LIGHT

(75) Inventor: Yang-Xin Fu, Chicago, IL (US)

(73) Assignee: The University of Chicago, Chicago, IL (US)

(*) Notice: Subject to any disclaimer, the term of this patent is extended or adjusted under 35 U.S.C. 154(b) by 921 days.

This patent is subject to a terminal disclaimer.

(21) Appl. No.: 11/500,177

(22) Filed: Aug. 7, 2006

(65) Prior Publication Data

US 2009/0092640 A1    Apr. 9, 2009

Related U.S. Application Data

(63) Continuation-in-part of application No. 10/865,623, filed on Jun. 10, 2004.

(60) Provisional application No. 60/478,126, filed on Jun. 12, 2003.

(51) Int. Cl.
*A61K 38/00* (2006.01)
*A61K 39/00* (2006.01)
*A61K 35/12* (2006.01)

(52) U.S. Cl. ............... 514/2; 424/184.1; 424/277.1

(58) Field of Classification Search ............... None
See application file for complete search history.

(56) References Cited

U.S. PATENT DOCUMENTS

| | | | |
|---|---|---|---|
| 4,797,368 A | 1/1989 | Carter et al. | |
| 4,980,286 A | 12/1990 | Morgan et al. | |
| 5,399,346 A | 3/1995 | Anderson et al. | |
| 5,436,146 A | 7/1995 | Shenk et al. | |
| 5,994,523 A | 11/1999 | Kawakami et al. | |
| 6,048,551 A | 4/2000 | Hilfinger et al. | |
| 6,140,467 A | 10/2000 | Ware | |
| 6,207,147 B1 | 3/2001 | Hiserodt et al. | |
| 6,475,986 B1* | 11/2002 | Aggarwal | 514/12 |
| 6,635,743 B1* | 10/2003 | Ebner et al. | 530/388.23 |
| 7,118,742 B2 | 10/2006 | Ware | |
| 7,241,576 B2 | 7/2007 | Aggarwal | |
| 2003/0166546 A1 | 9/2003 | Aggarwal | |
| 2005/0025754 A1 | 2/2005 | Fu | |
| 2009/0093429 A1 | 4/2009 | Fu et al. | |

FOREIGN PATENT DOCUMENTS

| WO | WO 00/53223 | * 9/2000 |
|---|---|---|
| WO | WO 01/79496 | 10/2001 |
| WO | WO 02/32463 | 4/2002 |
| WO | WO 02/34780 | 5/2002 |
| WO | WO 03/040307 | 5/2003 |
| WO | WO 2008/098183 | 8/2008 |

OTHER PUBLICATIONS

Yu et al, Nature Immunology, vol. 5, p. 141-149, Jan 4, 2004.*
Tamada et al, Nature Medicine, vol. 6, p. 283-289, 2000, IDS filed Jan. 11, 2007, BF.*
Harrop et al, J Biol Chem, vol. 273, p. 27548-27556, 1998.*
MeSH word search results for LIGHT, fibrrosarcoma and L1210 cell (2009).*
Sequence search result (2009).*
Sequence search result -2 (2009).*
MeSH word search results for fibrrosarcoma (2009).*
MeSH word search results for L1210 cell (2009).*
Database WPI (2002): "Section Ch, Week 200203," Derwent Publications Ltd., Longdon, GB, AN 2002-026029 (WO01/79496-Abstract).
Database WPI (2003): "Section Ch, Week 200340," Derwent Publications Ltd., Longdon, GB, AN 2003-430659 (WO03/040307-Abstract).
International Search Report issued in PCT/US2004/018631 (2004).
Boon et al., "Human tumor antigens recognized by T. lymphocytes," *J. Exp. Med.*, 183: 725-729 (1996).
Cannon et al., "Induction of transgene expression in Tg.AC(v-HA-ras) transgenic mice concomitant with DNA hypomethylation," *Mol Carcinog.*, 21: 244-250 (1998).
Chen et al., "Constiunulation of T cells for tumor immunity," *Immunol Today*, 14: 483-486 (1993).
Cyster, "Chemokines and cell migration in secondary lymphoid organs," *Science*, 286: 2098-2102 (1999).
Dougall et al. "RANK is essential for osteoclast and lymph node development," *Genes Dev*, 13: 2412-2424 (1999).
Ettinger, "The Role of tumor necrosis factor and lymphotoxin in lymphoid organ development," *Curr Top Microbiol Immunol*, 251: 203-210 (2000).
Fu et al., "Development and maturation of secondary lymphoid tissues," *Annu Rev Inununol*,17: 399-433 (1999).
Kang, et al, "Signaling via LTbetaR on the lamina propria stromal cells of the gut is required for IgA production," *Nat Immunol*, 3: 576-582 (2002).
Kim et al., "Regulation of peripheral lymph node genesis by the tumor necrosis factor family member TRANCE," *J Exp Med*, 192: 1467-1478 (2000).
Kong et al., "Activated T cells regulate bone loss and joint destruction in adjuvant arthritis through osteoprotegerin ligand," *Nature*, 402: 304-309 (1999).

(Continued)

*Primary Examiner*—Larry R. Helms
*Assistant Examiner*—Lei Yao
(74) *Attorney, Agent, or Firm*—Barnes & Thornburg LLP; Alice O. Martin

(57) ABSTRACT

Mutant LIGHT expressed in a tumor environment elicited high levels of chemokines and adhesion molecules, accompanied by massive infiltration of naïve T lymphocytes. Methods and compositions to elicit immune responses against tumors including tumor volume reduction and eradication of metastasis using mutant LIGHT are disclosed.

8 Claims, 28 Drawing Sheets

OTHER PUBLICATIONS

Leder, et al., "v-HA-ras transgene abrogates the initiation step in mouse skin tumorgenesis: effects of phorbol esters and terinoic acid," *Proc. Natl. Acad. Sci. USA*, 87: 9178-9182 (1990).

Mauri et al., "LIGHT, a new member of TNF superfamily, and lymphotoxin alpha are ligands for herpes virus entry mediator," *Immunity*, 8:21-30 (1998).

Melero et al., "Monoclonal antibodies against the 4-1BB T0cell activation molecule eradicate established tumors," *Nat Med*, 3: 682-685 (1997).

Ochsenbein et al., "Roles of tumor localization, second signals and cross priming in cytotoxic T-cell induction," *Nature*, 411: 1058-1064 (2001).

Ostrand-Rosenberg, "Cell-based vaccines for the stimulation of immunity to metastatic cancers," *Immunol Rev*, 170: 101-114 (1991).

Peace et al., "Lysis of ras oncogene-transformed cells by specific cytotoxic T lymphocytes elicited by primary in vitro immunization with mutated rats peptide," *J Exp Med*, 179: 473-479 (1994).

Rooney et al., "The lymphotoxin-beta receptor is necessary and sufficient for LIGHT-mediated apoptosis of tumor cells," *J Biol Chem*, 275: 14307-14315 (2000).

Rosenberg, et al., "Progress in human tumor immunology and immunotherapy," *Nature*, 411: 380-384 (2001).

Ruddle, "Lymphoid neo-organeogenesis: lymphotoxin's role in inflammation and development," *Immuno Res*, 19: 119-125 (1999).

Sarma et al., "Cytotoxic T lymphocytes to an unmutated tumor rejection antigen PIA: normal development but restrained effector function in vivo," *J Exp Med*, 189: 811-820 (1999).

Schreiber, "Tumor Immunology," In: *Fundamental Immunology* (ed. Paul, W.E.) Lippincott Rave Press, New York, 1247-1280 (1999).

Sha et al., "Selective expression of an antigen receptor on CD8-bearing T lymphocytes in transgenic mice," *Nature*, 335: 271-274 (1988).

Tamada et al., "Modulation of T-cell-mediated immunity in tumor and graft-versus-host disease models through the LIGHT co-stimulatory pathway," *Nat Med*, 6: 283-289 (2000).

Wang et al., "The complementation of lymphotoxin deficiency with LIGHT, a newly discovered TNF family member, for the restoration of secondary lymphoid structure and function," *Eur J Immunol*, 32: 1969 (2002).

Wang et al., "The regulation of T cell homeostasis and autoimmunity by T cell derived LIGHT," *J clinic. Invest*, 108: 1771-1780 (2001).

Wick et al., "Antigenic cancer cells grow progressively in immune hosts without evidence for T cell exhaustion or systemic anergy," *J Exp Med*, 186. 229-238 (1997).

Wu et al., "The requirement of membrane lymphotoxin for the presence of dendritic cells in lymphoid tissues," *J Exp Med*, 190: 629-638 (1999).

Ye et al., "Modulation of LIGHT-HVEM costimulation prolongs cardiac allograft survival" *J Exp Med*, 195: 795-800 (2002).

Ye et al., "Gene therapy for cancer using single-chain Fv fragments specific for 4-IBB," *Nat Med*, 8: 343-348 (2002).

Zhai et al., "LIGHT, a novel ligand for lymphotoxin beta receptor and TR2/HVEM induces apoptosis and suppresses in vivo tumor formation via gene transfer," *Journal of Clinical Investigation*, 102: 1142-1151 (1998).

Zinkernagel, "Immunity against solid tumors?," *Int J Cancer*, 93: 1-5 (2001).

Fan et al., "NK-cell activation by LIGHT triggers tumor-specific CD8+ T-cell immunity to reject established tumors," *Blood*, 107: 1342-1351 (2006).

Fidler, "The pathogenesis of cancer metastasis: the seed and soil hypothesis revisited," *Nature Reviews Cancer*, 3: 453-458 (2003).

Ghobrial et al., "Targeting Apoptosis Pathways in Cancer Therapy," *CA Cancer J. Clin.*, 55 (3): 178-194 (2005).

Houghton, "LIGHTing the way for tumor immunity," *Nature Immunology*, 5(2): 123-124 (2004).

Koscielny et al., "Breast Cancer: Relationship between the size of the primary tumour and the probability of metastatic dissemination," *Br. J. Cancer*, 49: 709-715 (1984).

Koscielny et al., "A simulation model of the natural history of human breast cancer," *Br. J. Cancer*, 52: 515-524 (1985).

Mezhir et al., "Ionizing radiation: a genetic switch for cancer therapy," *Cancer Gene Therapy*, 13: 1-6 (2006).

Rosenberg et al., "Cancer immunotherapy: moving beyond current vaccines," *Nature Medicine*, 10(9): 909-915 (2004).

Rosenberg et al., "Shedding Light on Immunotherapy for Cancer," *The New England Journal of Medicine*, 350(14): 1461-1463 (2004).

Schneider et al., "Lymphotoxin and LIGHT signaling pathways and target genes," *Immunological Reviews*, 202: 49-66 (2004).

Tamada et al., "Renewed interest in cancer immunotherapy with the tumor necrosis factor superfamily molecules," *Cancer Immunol. Immunother.*, 55: 355-362 (2006).

Wang et al., "The Role of LIGHT in T Cell-Mediated Immunity," *Immunologic Research*, 30(2): 201-214 (2004).

Ware, "Network Communications: Lymphotoxins, LIGHT, and TNF," *Annu. Rev. Immunol.*, 23: 787-819 (2005).

International Search Report issued in PCT/US2008/53448 (2008).

* cited by examiner

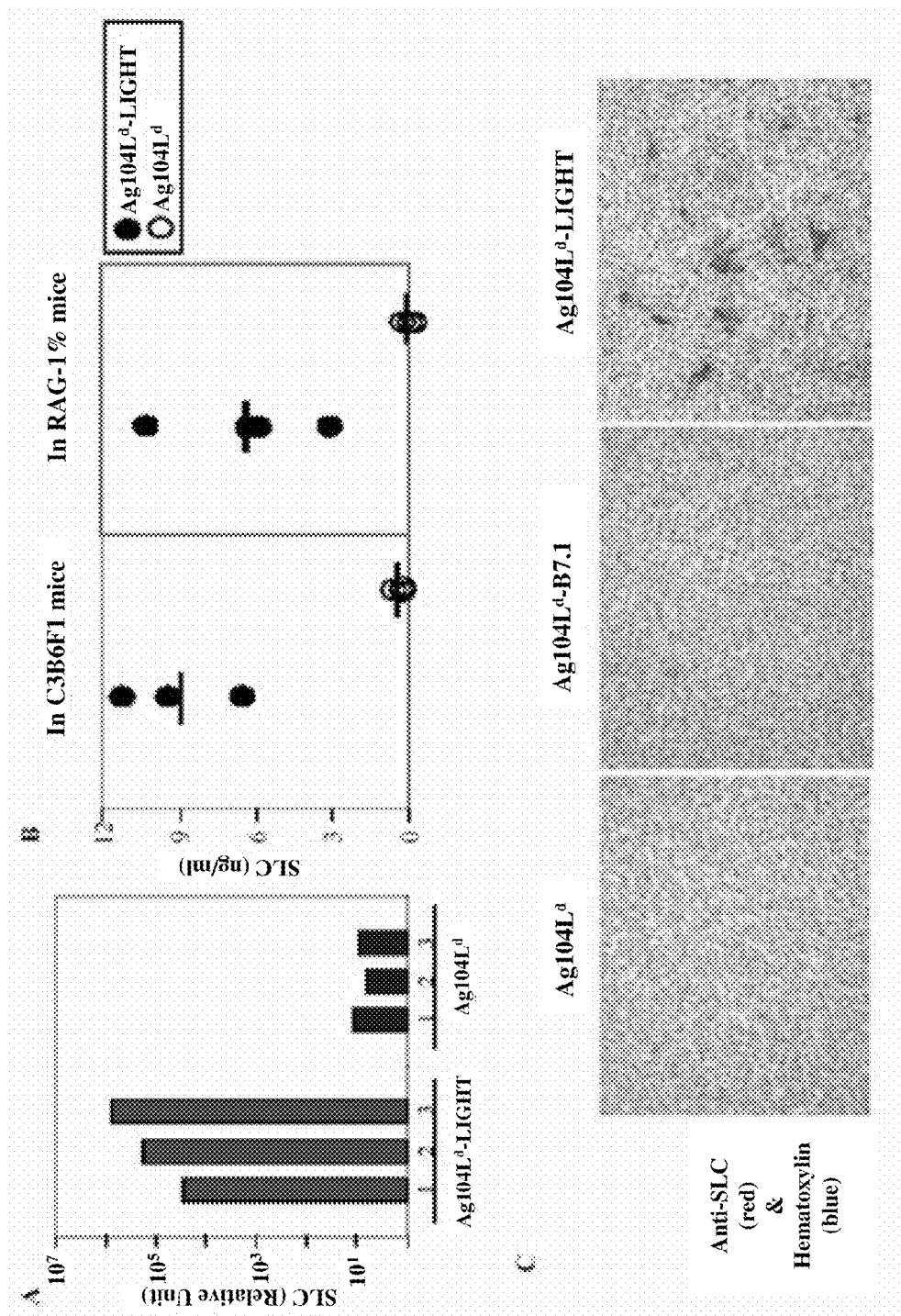
FIG. 6A-C

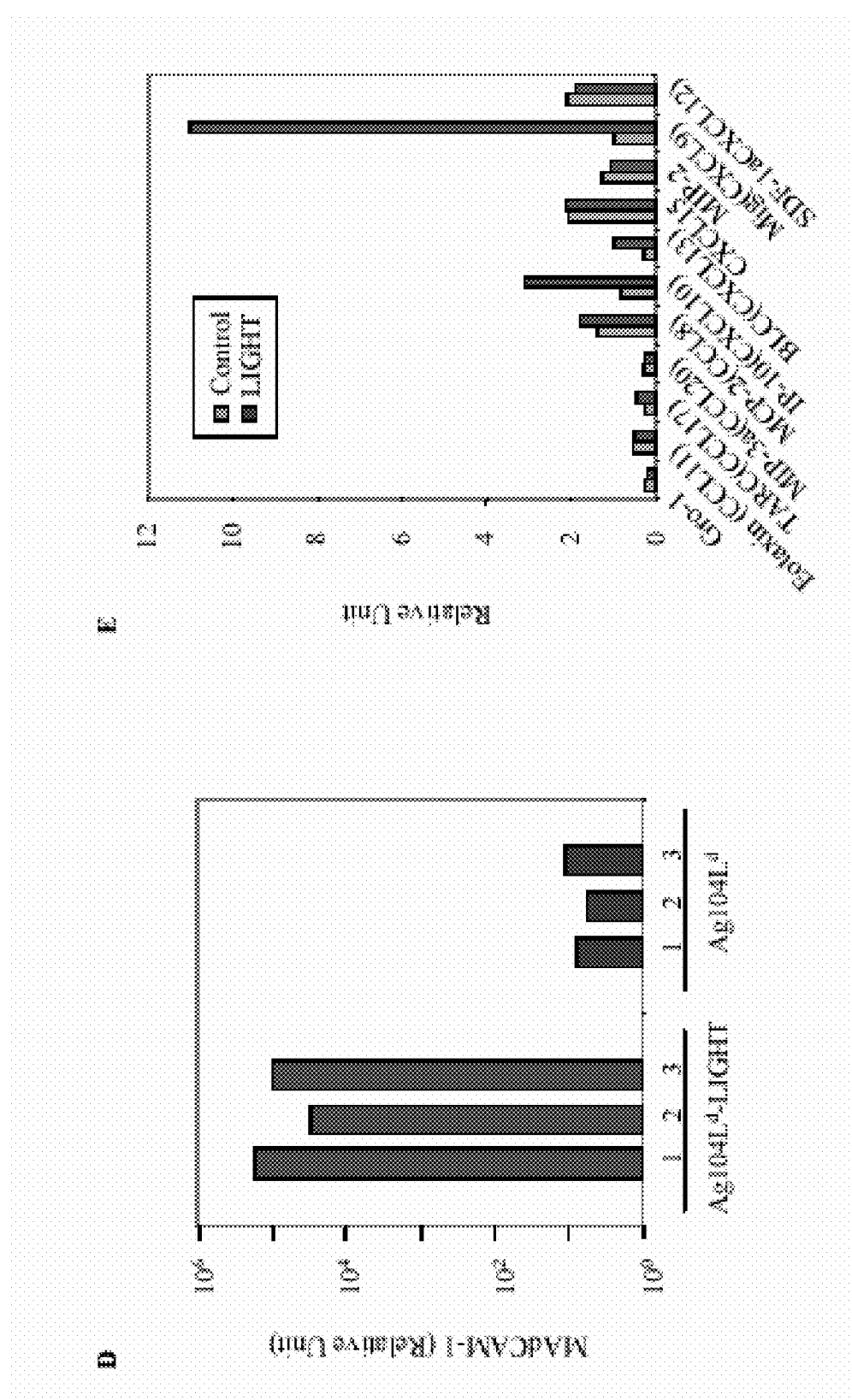
FIG. 6D-E

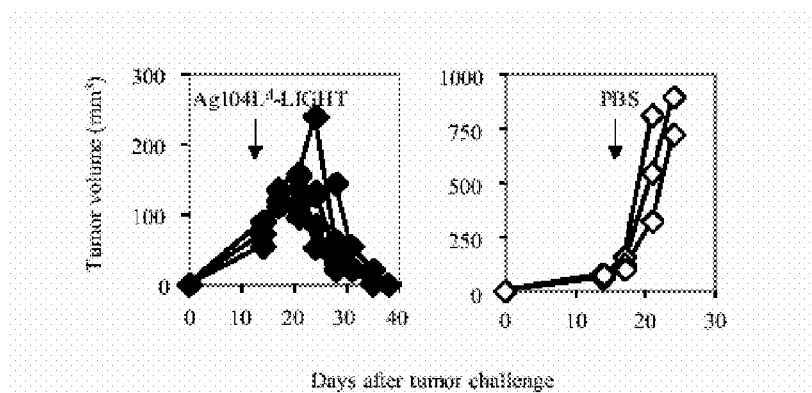

FIG. 8

```
1    gcccaacacg ctcgggcagt ttgcacagcc cgagcgtgtt gggcaattgt ggtttcctcc
61   ggagaggagg aactcaggct tgccaaccct ttccctgggc ttcggagcct cagctgctct
121  ggcatggaga gtgtggtaca gccttcagtg tttgtggtgg atggacagac ggacatccca
181  ttcaggcggc tggaacagaa ccaccggaga cggcgctgtg cactgtcca ggtcagcctg
241  gccctggtgc tgctgctagg tgctgggctg gccactcagg gctggtttct cctgagactg
301  catcaacgtc ttggagacat agtagctcat ctgccagatg gaggcaaagg ctcctgggag
361  aagctgatac aagatcaacg atctcaccag gccaacccag cagcacatct tacaggagcc
421  aacgccagct tgataggtat tggtggacct ctgttatggg agacacgact tggcctggcc
481  ttcttgaggg gcttgacgta tcatgatggg gccctggtga ccatggagcc cggttactac
541  tatgtgtact ccaaagtgca gctgagcggc gtgggctgcc cccaggggct ggccaatggc
601  ctccccatca cccatggact atacaagcgc acatcccgct acccgaagga gttagaactg
661  ctggtcagtc ggcggtcacc ctgtggccgg ccaacagct cccgagtctg gtgggacagc
721  agcttcctgg gcggcgtggt acatctggag gctggggaag aggtggtggt ccgcgtgcct
781  ggaaaccgcc tggtcagacc acgtgacggc accaggtcct atttcggagc tttcatggtc
841  tgaaggctgc ggtgacaatg tattttgtgg agggacctct ccaggactca cctcaaaccc
901  agcaataggg tttgaagtcc tcccttttaag gagccctgaa ctctgcagtg ctcggggcgg
961  tgtagactgc tgacctgctt tgggcaatct tcaaatcaga gacctggaga cttggggcgt
1021 ggagccagg agcgaggggt cagctcattt gctgatatt caggaagaaa gaatcaagct
1081 ggggtattta tgcttctgat gcaaacactg agatttcggc tttctgggtt ttgagctgga
1141 ggcaagaaac cttcccagag tgtcatcagg accatgttgg caggacttgg ggctccagac
1201 ttgccaccac actctggcct ctcccatcca tccgctgcat tggtttccag ccaccaaaac
1261 agcactggcc ccctggctgc aactggccag gtacgagctt ctgagcacct acattcctca
1321 gggacatctt gatgagatct cagtactcag tccaatgcgc agcagcgaca gacatgccag
1381 gaatggttgg tcagaaggga agggaggaaa gggaggaaag aagggaatgc agaagagaag
1441 ggggaaaac aagaccaaaa caaacagca acaacaaagc ggcagggagg aggtgacacc
1501 cttggggata ctttagtcaa cacacttaga acagattgtg ccaggcctgt tggattcctg
1561 gagttgatgg gatcgtggga aggcacaatg gggagcaagt gggcttgggt tatggctcag
1621 tgggtaaagt gcaattatgg ggatctgagt ttgaatccct ggtacccata taagacaca
1681 gatgcggtga tgggcacttg tgacaatgag atcatcaata gggaatggag acaggaggga
1741 cctctggggt tcactggcca ggcagtctag ctgaatcaaa gagctccaag ttcagtcgat
1801 agctcctgaa gatgacaact gaggctattc tccaaacccc acacgcagga cacatgcgta
1861 at
```

FIG. 9

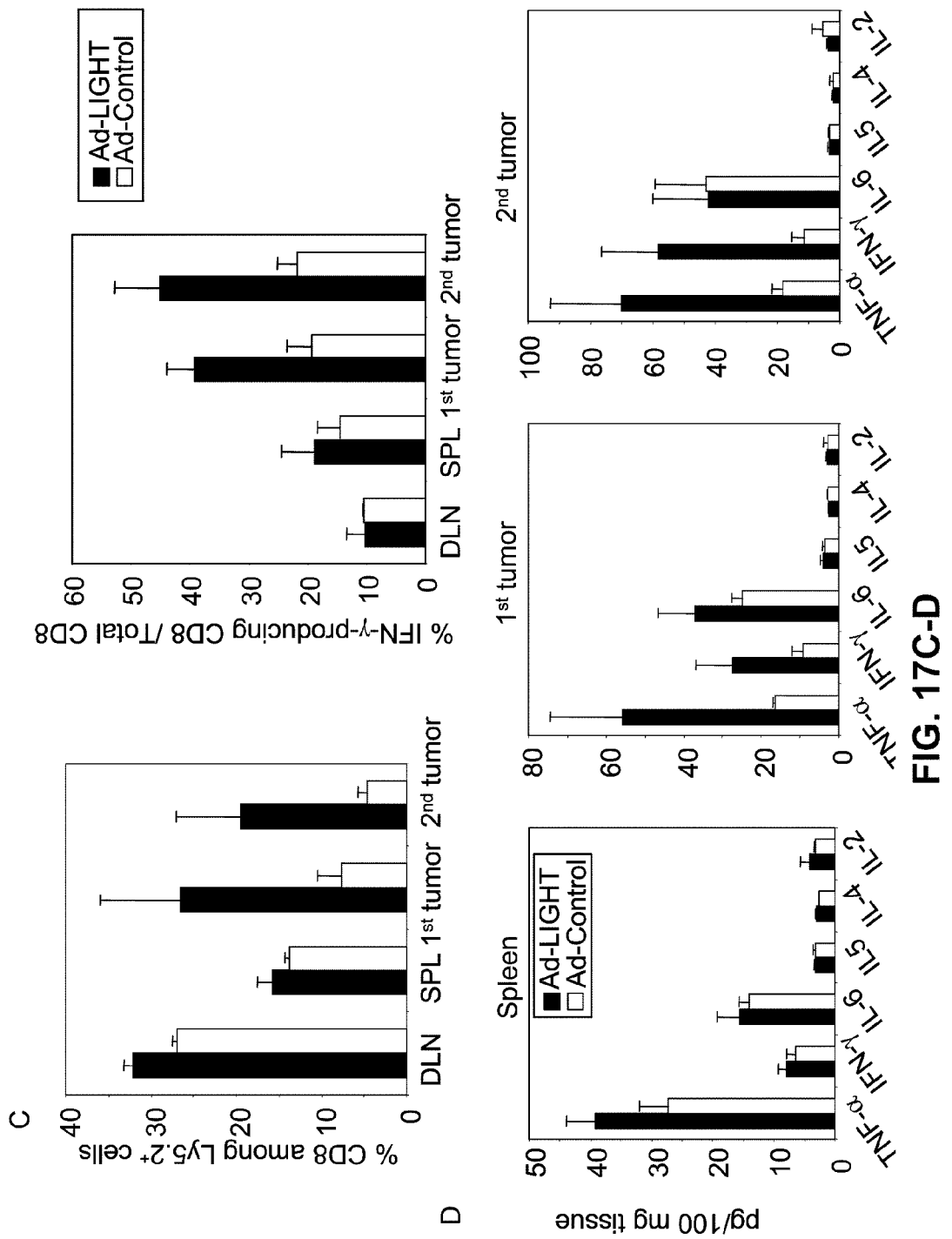
FIG. 17C-D

+ : AD293 cells/adv-cmv-null
* : AD293 cells/adv-cmv-mutant hLIGHT#7

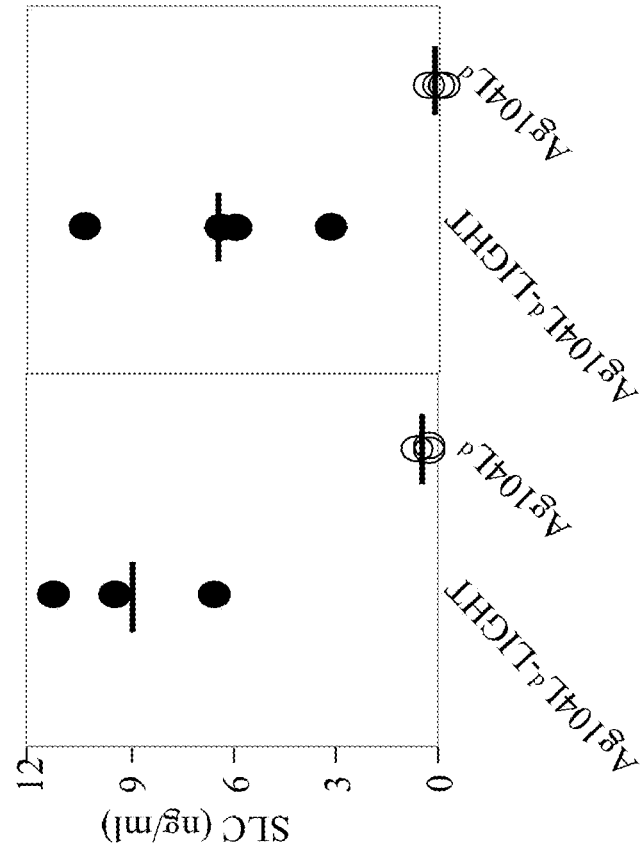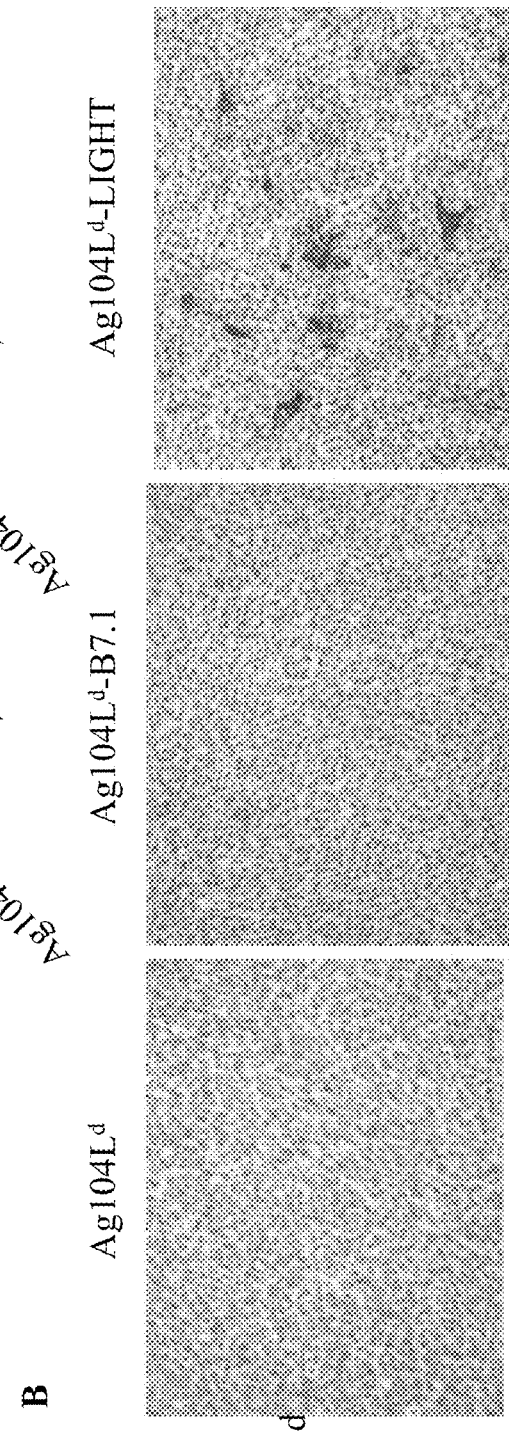
FIG. 21 ically, increase of infiltration of T cells to the tumor site

SEQUENCE LISTING

<160> NUMBER OF SEQ ID NOS: 24

<210> SEQ ID NO 1
<211> LENGTH: 181
<212> TYPE: PRT
<213> ORGANISM: Artificial Sequence
<220> FEATURE:
<223> OTHER INFORMATION: Description of Artificial Sequence: Recombinant
      Polypeptide

<400> SEQUENCE: 1

Gln Leu His Trp Arg Leu Gly Glu Met Val Thr Arg Leu Pro Asp Gly
 1               5                  10                  15

Pro Ala Gly Ser Trp Glu Gln Leu Ile Gln Glu Arg Arg Ser His Glu
            20                  25                  30

Val Asn Pro Ala Ala His Leu Thr Gly Ala Asn Ser Ser Leu Thr Gly
        35                  40                  45

Ser Gly Gly Pro Leu Leu Trp Glu Thr Gln Leu Gly Leu Ala Phe Leu
    50                  55                  60

Arg Gly Leu Ser Tyr His Asp Gly Ala Leu Val Val Thr Lys Ala Gly
65                  70                  75                  80

Tyr Tyr Tyr Ile Tyr Ser Lys Val Gln Leu Gly Gly Val Gly Cys Pro
                85                  90                  95

Leu Gly Leu Ala Ser Thr Ile Thr His Gly Leu Tyr Lys Arg Thr Pro
            100                 105                 110

Arg Tyr Pro Glu Glu Leu Glu Leu Val Ser Gln Gln Ser Pro Cys
        115                 120                 125

Gly Arg Ala Thr Ser Ser Ser Arg Val Trp Trp Asp Ser Ser Phe Leu
    130                 135                 140

Gly Gly Val Val His Leu Glu Ala Gly Glu Lys Val Val Val Arg Val
145                 150                 155                 160

Leu Asp Glu Arg Leu Val Arg Leu Arg Asp Gly Thr Arg Ser Tyr Phe
                165                 170                 175

Gly Ala Phe Met Val
            180

<210> SEQ ID NO 2
<211> LENGTH: 723
<212> TYPE: DNA
<213> ORGANISM: Artificial Sequence
<220> FEATURE:
<223> OTHER INFORMATION: Description of Artificial Sequence: Recombinant
      Nucleic Acid

<400> SEQUENCE: 2
atggaggaga gtgtcgtacg gccctcagtg tttgtggtgg atggacagac cgacatccca      60
ttcacgaggc tgggacgaag ccaccggaga cagtcgtgca gtgtggcccg ggtgggtctg     120
ggtctcttgc tgttgctgat gggggctggg ctggccgtcc aaggctggtt cctcctgcag     180
ctgcactggc gtctaggaga gatggtcacc cgcctgcctg acggacctgc aggctcctgg     240
gagcagctga tacaagagcg aaggtctcac gaggtcaacc cagcagcgca tctcacaggg     300

| | |
|---|---|
| gccaactcca gcttgaccgg cagcggggggg ccgctgttat gggagactca gctgggcctg | 360 |
| gccttcctga ggggcctcag ctaccacgat ggggcccttg tggtcaccaa agctggctac | 420 |
| tactacatct actccaaggt gcagctgggc ggtgtgggct gcccgctggg cctggccagc | 480 |
| accatcaccc acggcctcta caagcgcaca ccccgctacc ccgaggagct ggagctgttg | 540 |
| gtcagccagc agtcaccctg cggacgggcc accagcagct cccgggtctg gtgggacagc | 600 |
| agcttcctgg gtggtgtggt acacctggag gctggggaga aggtggtcgt ccgtgtgctg | 660 |
| gatgaacgcc tggttcgact gcgtgatggt acccggtctt acttcggggc tttcatggtg | 720 |
| tga | 723 |

<210> SEQ ID NO 3
<211> LENGTH: 1862
<212> TYPE: DNA
<213> ORGANISM: Artificial Sequence
<220> FEATURE:
<223> OTHER INFORMATION: Description of Artificial Sequence: Recombinant
    Nucleic Acid

<400> SEQUENCE: 3

| | |
|---|---|
| gcccaacacg ctcgggcagt ttgcacagcc cgagcgtgtt gggcaattgt ggtttcctcc | 60 |
| ggagaggagg aactcaggct tgccaaccct ttccctgggc ttcggagcct cagctgctct | 120 |
| ggcatggaga gtgtggtaca gccttcagtg tttgtggtgg atggacagac ggacatccca | 180 |
| ttcaggcggc tggaacagaa ccaccggaga cggcgctgtg gcactgtcca ggtcagcctg | 240 |
| gccctggtgc tgctgctagg tgctgggctg gccactcagg gctggtttct cctgagactg | 300 |
| catcaacgtc ttggagacat agtagctcat ctgccagatg gaggcaaagg ctcctgggag | 360 |
| aagctgatac aagatcaacg atctcaccag gccaacccag cagcacatct tacaggagcc | 420 |
| aacgccagct tgataggtat tggtggacct ctgttatggg agacacgact tggcctggcc | 480 |
| ttcttgaggg gcttgacgta tcatgatggg gccctggtga ccatggagcc cggttactac | 540 |
| tatgtgtact ccaaagtgca gctgagcggc gtgggctgcc ccaggggct ggccaatggc | 600 |
| ctccccatca cccatggact atacaagcgc acatcccgct acccgaagga gttagaactg | 660 |
| ctggtcagtc ggcggtcacc ctgtggccgg gccaacagct cccgagtctg gtgggacagc | 720 |
| agcttcctgg gcgcgtggt acatctggag gctggggaag aggtggtggt ccgcgtgcct | 780 |
| ggaaaccgcc tggtcagacc acgtgacggc accaggtcct atttcggagc tttcatggtc | 840 |
| tgaaggctgc ggtgacaatg tattttgtgg agggacctct ccaggactca cctcaaaccc | 900 |
| agcaataggg tttgaagtcc tccctttaag gagccctgaa ctctgcagtg ctcggggcgg | 960 |
| tgtagactgc tgacctgctt tgggcaatct tcaaatcaga gacctggaga cttggggcgt | 1020 |
| ggagcccagg agcgagggt cagctcattt gcctgatatt caggaagaaa gaatcaagct | 1080 |
| ggggtattta tgcttctgat gcaaacactg agatttcggc tttctgggtt ttgagctgga | 1140 |
| ggcaagaaac cttcccagag tgtcatcagg accatgttgg caggacttgg ggctccagac | 1200 |
| ttgccaccac actctggcct ctcccatcca tccgctgcat tggtttccag ccaccaaaac | 1260 |
| agcactggcc ccctggctgc aactggccag gtacgagctt ctgagcacct acattcctca | 1320 |
| gggacatctt gatgagatct cagtactcag tccaatgcgc agcagcgaca gacatgccag | 1380 |
| gaatggttgg tcagaaggga agggaggaaa gggaggaaag aagggaatgc agaagagaag | 1440 |
| gggggaaaac aagaccaaaa caaaacagca acaacaaagc ggcagggagg aggtgacacc | 1500 |
| cttggggata cttagtcaa cacacttaga acagattgtg ccaggcctgt tggattcctg | 1560 |

```
gagttgatgg gatcgtggga aggcacaatg gggagcaagt gggcttgggt tatggctcag    1620
tgggtaaagt gcaattatgg ggatctgagt ttgaatccct ggtacccata taaagacaca    1680
gatgcggtga tgggcacttg tgacaatgag atcatcaata gggaatggag acaggaggga    1740
cctctggggt tcactggcca ggcagtctag ctgaatcaaa gagctccaag ttcagtcgat    1800
agctcctgaa gatgacaact gaggctattc tccaaacccc acacgcagga cacatgcgta    1860
at                                                                   1862
```

<210> SEQ ID NO 4
<211> LENGTH: 4
<212> TYPE: PRT
<213> ORGANISM: Unknown Organism
<220> FEATURE:
<223> OTHER INFORMATION: Description of Unknown Organism: proteolytic
      peptide from various organisms

<400> SEQUENCE: 4

Glu Lys Leu Ile
 1

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
agactcagga gcccaaagca                                                20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
gttgaagcag ggcaagggt                                                 19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
ccacctcatg ctggcctccg tc                                             22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
gacaccagct tgggcagtgt                                                20

-continued

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
cagcatgccc cgtacagag                                              19

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
cagaccctcc caggcagcag tatcc                                       25

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
ttcaccacca tggagaaggc                                             20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
ggcatggact gtggtcatga                                             20

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
tgcatcctgc accaccaact gcttag                                      26

<210> SEQ ID NO 14
<211> LENGTH: 723
<212> TYPE: DNA
<213> ORGANISM: Homo sapiens

<400> SEQUENCE: 14
atggaggaga gtgtcgtacg gccctcagtg tttgtggtgg atggacagac cgacatccca      60
ttcacgaggc tgggacgaag ccaccggaga cagtcgtgca gtgtggcccg ggtgggtctg     120
ggtctcttgc tgttgctgat gggggctggg ctggccgtcc aaggctggtt cctcctgcag     180
ctgcactggc gtctaggaga gatggtcacc cgcctgcctg acggacctgc aggctcctgg     240

-continued

```
gagcagctga tacaagagcg aaggtctcac gaggtcaacc cagcagcgca tctcacaggg    300
gccaactcca gcttgaccgg cagcgggggg ccgctgttat gggagactca gctgggcctg    360
gccttcctga ggggcctcag ctaccacgat ggggcccttg tggtcaccaa agctggctac    420
tactacatct actccaaggt gcagctgggc ggtgtgggct gcccgctggg cctggccagc    480
accatcaccc acggcctcta caagcgcaca cccgctacc ccgaggagct ggagctgttg     540
gtcagccagc agtcaccctg cggacgggcc accagcagct cccgggtctg gtgggacagc    600
agcttcctgg gtggtgtggt acacctggag gctggggaga aggtggtcgt ccgtgtgctg    660
gatgaacgcc tggttcgact gcgtgatggt acccggtctt acttcggggc tttcatggtg    720
tga                                                                  723
```

<210> SEQ ID NO 15
<211> LENGTH: 240
<212> TYPE: PRT
<213> ORGANISM: Homo sapiens

<400> SEQUENCE: 15

```
Met Glu Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 16
<211> LENGTH: 236
<212> TYPE: PRT
<213> ORGANISM: Homo sapiens

<400> SEQUENCE: 16

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
                35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Gln Glu Arg Arg Ser His Glu Val Asn Pro Ala Ala His Leu Thr Gly
                85                  90                  95

Ala Asn Ser Ser Leu Thr Gly Ser Gly Pro Leu Leu Trp Glu Thr
                100                 105                 110

Gln Leu Gly Leu Ala Phe Leu Arg Gly Leu Ser Tyr His Asp Gly Ala
            115                 120                 125

Leu Val Val Thr Lys Ala Gly Tyr Tyr Tyr Ile Tyr Ser Lys Val Gln
            130                 135                 140

Leu Gly Gly Val Gly Cys Pro Leu Gly Leu Ala Ser Thr Ile Thr His
145                 150                 155                 160

Gly Leu Tyr Lys Arg Thr Pro Arg Tyr Pro Glu Glu Leu Glu Leu Leu
                165                 170                 175

Val Ser Gln Gln Ser Pro Cys Gly Arg Ala Thr Ser Ser Ser Arg Val
            180                 185                 190

Trp Trp Asp Ser Ser Phe Leu Gly Gly Val Val His Leu Glu Ala Gly
        195                 200                 205

Glu Lys Val Val Val Arg Val Leu Asp Glu Arg Leu Val Arg Leu Arg
    210                 215                 220

Asp Gly Thr Arg Ser Tyr Phe Gly Ala Phe Met Val
225                 230                 235

<210> SEQ ID NO 17
<211> LENGTH: 4
<212> TYPE: PRT
<213> ORGANISM: Unknown Organism
<220> FEATURE:
<223> OTHER INFORMATION: Description of Unknown Organism: proteolytic
      peptide from various organisms

<400> SEQUENCE: 17

Glu Gln Leu Ile
 1

<210> SEQ ID NO 18
<211> LENGTH: 767
<212> TYPE: DNA
<213> ORGANISM: Mus musculus

<400> SEQUENCE: 18
gggcgaattg ggtaccggat ccgccaccat ggagagcgtg gtgcagccca gcgtgttcgt      60
ggtggacggc cagaccgaca tccccttcag gaggctggag cagaaccaca ggcggaggag     120
atgtggcacc gtgcaggtgt ccctggccct ggtgctgctg ctgggcgctg gcctggccac     180
ccagggctgg tttctgctga ggctgcacca gaggctgggc gacatcgtgg cccacctgcc     240
cgatggcgga aagggcagct ggcaggacca gaggagccac caggccaacc ctgccgccca     300
cctgacaggc gccaacgcca gcctgatcgg catcggcgga cccctgctgt gggagaccag     360

```
gctgggcctg gctttcctga ggggcctgac ctaccacgac ggcgccctgg tgaccatgga    420
gcccggctac tactacgtgt acagcaaggt gcagctgtcc ggagtgggct gccctcaggg    480
cctggccaac ggcctgccca tcacccacgg cctgtacaag aggaccagca gatacccaa    540 ggagctggag ctgctggtct ccaggcggag ccctgtggc agggccaaca gcagccgagt    600
gtggtgggac agcagcttcc tgggcggcgt ggtgcacctg gaggcggcg aggaggtggt    660 ggtgagggtg cccggcaaca ggctggtgag gcccagggac ggcaccagga gctacttcgg    720
cgccttcatg gtgtgatgag cggccgcgag ctccagcttt tgttccc               767

<210> SEQ ID NO 19
<211> LENGTH: 814
<212> TYPE: DNA
<213> ORGANISM: Homo sapiens

<400> SEQUENCE: 19
gaattcgagc tcggtacccg acacggtacc ggatccgcca ccatggagga gagcgttgtg     60
aggcccagcg tgttcgtggt ggacggccag accgacatcc ccttcacccg gctgggccgg    120
agccaccgga ggcagagctg ctccgtggcc agagtggggc tgggcctgct gctcctgctg    180
atgggagccg gctggccgt gcagggctgg ttcctgctgc agctgcactg gcggctgggc    240
gagatggtga cccggctgcc cgatggccct gccggcagct ggcaggagcg gcggagccac    300
gaggtgaacc ctgccgccca cctgaccggc gccaacagca gcctgaccgg cagcggcgga    360
cccctgctgt gggagaccca gctgggcctg gccttcctga ggggcctgag ctaccacgac    420
ggcgccctgg tggtgaccaa ggccggctac tactacatct acagcaaggt gcagctgggc    480
ggagtgggct gccctctggg gctggccagc accatcaccc acggcctgta caagcggacc    540
cccagatacc ccgaggagct ggagctgctg gtgtcccagc agagcccctg tggcagggcc    600
acctccagca gccgggtgtg gtgggacagc agcttcctgg gcggcgtggt gcacctggag    660
gccggcgaga aagtggttgt gagggtgctg gacgagcggc ttgtgaggct gagggacggc    720
acccggagct acttcggcgc cttcatggtg tgatgagcgg ccgcgagctc gtctcgggga    780
tcctctagag tcgacctgca ggcatgcaag cttg                               814

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
catggatcca agaccatgga gagtgtggta ca                                   32

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
agatcgttga tcttgccagg agcctttgcc                                      30

<210> SEQ ID NO 22
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22
ggcaaaggct cctggcaaga tcaacgatct                                      30

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23
acctctagat cagaccatga aagctccga                                       29

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Recombinant
      protease digestion site

<400> SEQUENCE: 24
gagcagctga ta                                                         12
```

INCREASED T-CELL TUMOR INFILTRATION AND ERADICATION OF METASTASES BY MUTANT LIGHT This application is a continuation-in-part of U.S. Ser. No. 10/865,623, filed Jun. 10, 2004, which claims priority from U.S. Ser. No. 60/477,733 filed Jun. 11, 2003 and U.S. Ser. No. 60/478,126 filed Jun. 12, 2003.

The government has rights in the invention due to partial support from NIH R01 HD 37104, R01-062026, and R01-DK58897.

BACKGROUND OF THE DISCLOSURE

The paucity of activated T cells infiltrating established tumors in immunocompetent hosts helps to explain the inability of hosts to dispose of tumors. Experiments in animal models as well as clinical studies indicate that the immune system can recognize and kill individual tumor cells, but a host cannot generally eradicate established solid tumors. There may be several explanations for the failure of the host to respond effectively to established tumors: 1) lack of early T cell priming due to poor direct or indirect presentation in lymphoid tissues because of an inadequate number of tumor cells (especially those of non-hemopoietic origin) migrating to the lymphoid tissue; 2) inadequate numbers of immune cells migrating to tumor sites due to biological barriers around tumor tissues; 3) exhausted or short-lived activated antigen-specific T cells that fail to combat tumor growth due to limited repertoires; 4) unresponsiveness or ignorance of T cells to tumors; 5) an inhibitory microenvironment or lack of stimulation inside tumors to activate the immune system.

Clinically, increase of infiltration of T cells to the tumor site is closely associated with better prognosis. Previous studies have shown that preventive vaccinations were effective in inducing the rejection of inoculated tumor cells. After tumor growth has been established, however, the therapeutic vaccinations usually fail to reject tumors. Surgical debulk of tumor does not boost the immune response to tumors. Furthermore, it was reported that even the expression of a strong antigen on tumor cells was insufficient in promoting the rejection of an established tumor, despite the presence of excessive numbers of antigen-specific T cells in the lymphoid tissues. Lack of T cells priming and/or infiltrating an established tumor is one of the major obstacles for either natural or therapeutic approaches against antigenic cancers. In addition, insufficient expression of costimulatory molecules inside tumor tissues may fail to activate infiltrating T cells and result in the anergy of tumor-reactive T cells.

The lack of early T cell priming is possibly attributed to only a few tumor cells that migrated from solid tissue to lymphoid tissues for direct presentation. Genetic analysis using bone marrow chimeras has revealed two modes of antigen presentation for priming MHC-I-restricted CD8$^+$ T cells. Direct-priming is mediated by the engagement of T cells with the cells that synthesize the protein with antigenic epitopes, whereas cross-priming is mediated by the host antigen-presenting cells that take up antigens synthesized by other cells. The mechanisms for priming tumor-specific T cells has been vigorously debated and so far remains inconclusive. Understanding how and where tumor antigens are presented to T cells would help find a therapeutic action against tumors.

LIGHT (homologous to lymphotoxin, exhibits inducible expression, and competes with HSV glycoprotein D for herpes virus entry mediator, a receptor expressed by T lymphocytes) is a recently identified type II transmembrane glycoprotein of the TNF ligand superfamily. LIGHT (TNFSF14) is a tumor-necrosis factor (TNF) family member that interacts with Lymphotoxin β receptor (LTβR) and herpes virus entry mediator (HVEM) mainly expressed on stromal cells and T cells, respectively. LTβR signaling is required for the formation of organized lymphoid structures, which can be attributed, at least in part, to its ability to induce the expression of chemokines and adhesion molecules that attract naïve T cells and dendritic cells (DC) in lymphoid organs. Stimulation of LTβR on stromal cells by LIGHT in vivo leads to the expression of CCL21, which attracts naïve T cells in the T cell area of the spleen in the absence of LTαβ, another ligand for LTβR. These results demonstrate that LIGHT is able to interact with LTβR to regulate CCL21 chemokine expression. In addition, LIGHT also exhibits a potent, CD28-independent co-stimulatory activity for T cell priming and expansion leading to enhanced T cell immunity against tumors and/or increased autoimmunity. Signaling via LTβR is required for the formation of organized lymphoid tissues. Lymphotoxin β receptor (LTβR) plays an important role in the formation of lymphoid structures. LTβR is activated by two members of the TNF family, membrane lymphotoxin αβ and LIGHT (FIG. 1). LTβR plays pivotal roles in the formation of LNs and the distinct organization of T, B zones in secondary lymphoid organs. Signaling via LTβR regulates the expression of chemokines and adhesion molecules within secondary lymphoid organs. Chemokines and adhesion molecules control the migration and positioning of DCs and lymphocytes in the spleen. Over-expression of soluble LT or TNF in non-lymphoid tissues was sufficient to promote functional lymphoid neogenesis.

LIGHT plays a unique role in T cell activation and the formation of lymphoid tissue. LIGHT is a ligand for LTβR and herpes virus entry mediator (HVEM). LIGHT is predominantly expressed on lymphoid tissues. Interactions between LIGHT and LTβR restore lymphoid structures in the spleen of LTα$^{-/-}$ mice. In addition, upregulation of LIGHT causes T cell activation and migration into non-lymphoid tissues and forms lymphoid-like structures. Conversely, LIGHT$^{-/-}$ mice showed impaired T cell activation and delayed cardiac rejection. Therefore, LIGHT is a potent costimulatory molecule that also promotes the formation of lymphoid tissues to enhance local immune responses. Lack of efficient priming of naïve T cells in draining lymphoid tissues and the inability to expand tumor-specific T cells within tumors prevent the eradication of cancer.

Micrometastases (small aggregates of cancer cells visible microscopically) can become established at a very early stage in the development of heterogeneous primary tumors and seed distal tissue sites prior to their clinical detection. For example, the detectable metastasis in breast cancer can be observed when the primary tumor size is very small. Therefore, at the time of diagnosis many cancer patients already have microscopic metastasis, an observation that has led to the development of post-surgical adjuvant therapy for patients with solid tumors. Despite these advances, success has been limited, and optimal treatment of metastatic disease continues to pose a significant challenge in cancer therapy.

A variety of human and murine cancers have been proven to be antigenic and able to be recognized by T cells. Tumor-reactive T cells could theoretically seek out and destroy tumor antigen-positive cancer cells and spare the surrounding healthy tissues. However, the naturally existing T cell responses against malignancies in human are often not sufficient to cause regression of the tumors, primary or metastases. It has been recently reported that sporadic spontaneous but immunogenic tumors avoid destruction by inducing T cell tolerance but that activation of tumor antigen-specific T cells may completely prevent the development of spontaneous tumors. Thus, breaking tolerance and generating such T cells capable of rejecting tumors around the time of treatment of the primary tumor could represent a potential approach to clearing metastatic tumor cells. As antigen-lost variants can escape under immunological pressure, immunotherapy should be applicable independent of knowledge of specific tumor antigens.

From an immunological perspective, present clinical strategies hinder the immune defense against malignancies and further diminish the effectiveness of immunotherapy. Although removal of a tumor may reverse tumor-induced immune suppression, surgical excision of the primary tumor before immunotherapy also removes the major source of antigen, which may lead to a reduction of the activation of CTLs since the efficiency of priming is correlated with the tumor antigen load. In addition, currently utilized adjuvant treatment with chemotherapy and radiation therapy that is meant to kill residual tumor cells may in fact impair anti-tumor immune responses by destroying or inhibiting T cells.

A challenge in developing an effective immunotherapy is to devise an approach to increase the number or enhance the function of circulating tumor-specific T cells that may detect and destroy microscopic metastatic cells before they become clinically meaningful.

In the present disclosure, inducing immune responses in tumor tissues via mutant LIGHT prior to surgery generated sufficient primed antigen-specific effector T cells to exit the tumor and eradicate metastasis. Delivery of mutant LIGHT, using a recombinant adenovirus into to the primary tumor of 4T1 mammary carcinoma bearing mice also mediated prevention and eradication of spontaneous metastasis.

SUMMARY

"Mutant LIGHT" refers to a LIGHT protein or a LIGHT-derived peptide that is resistant to proteolytic cleavage, stably expressed in the surface of tumor cells, and exhibits increased activation of tumor specific T-cells, compared to normal or native LIGHT protein.

Mutant LIGHT creates a lymphoid-like microenvironment that expresses chemokines, adhesion molecules and co-stimulatory molecules for priming T-cells to kill tumor cells.

Mutant LIGHT resists protease digestion and is expressed on tumor cells. Non-mutant LIGHT is not expressed on the surface of tumors and does not induce effective anti-tumor activity.

Mutant LIGHT-expressing tumors as a therapeutic vaccine attracts more naïve T cells and then activates them so that more anti-tumor specific T cells are generated to combat local and distal tumors.

Mutant LIGHT and tumor (or tumor antigens) prime T cells and lead to long-term protection as a preventive vaccine.

A novel method to treat tumors (solid tumors in particular) is to create lymphoid-like microenvironments that express chemokines, adhesion molecules, and costimulatory molecules required for priming naïve T cells and expanding activated T cells by the use of mutant LIGHT molecules. Broader T cells are generated against tumors. Adenoviral vectors that include mutant LIGHT encoding sequences, are effective against tumors and metastasis. Tumor volume was reduced in vivo when vectors delivered mutant LIGHT to tumors as compared to tumors injected with control vectors.

Also described is method of reducing cancer metastasis, including the steps of:
   (a) introducing a nucleic acid molecule encoding mutant LIGHT or a fragment thereof into a tumor site, wherein the mutant LIGHT does not have a proteolytic site;
   (b) expressing the nucleic acid molecule in the tumor; and
   (c) reducing cancer metastasis by stimulating activation of tumor-specific T-cells against the tumor.

In various embodiments, the mutant LIGHT has an amino acid change in a proteolytic site including an amino acid sequence EQLI (SEQ ID NO: 17) from positions 81-84 of native LIGHT protein; the mutant LIGHT does not have the proteolytic site, an amino acid sequence EQLI (SEQ ID NO: 17) from positions 81-84 of native LIGHT protein; the mutant LIGHT has an amino acid change in a proteolytic site comprising an amino acid sequence EKLI (SEQ ID NO: 4) from positions 79-82 of native LIGHT protein; the mutant LIGHT does not have the proteolytic site comprising an amino acid sequence EKLI (SEQ ID NO: 4) from positions 79-82 of native LIGHT protein.

The nucleic acid molecule disclosed encodes a recombinant mutant LIGHT including an extracellular domain: (SEQ ID NO: 1)

QLHWRLGEMVTRLPDGPAGSWEQLIQERRSHEVNPAAHLTGANSSLTGSG

GPLLWETQLGLAFLRGLSYHDGALVVTKAGYYYIYSKVQLGGVGCPLGLA

STITHGLYKRTPRYPEELELLVSQQSPCGRATSSSRVWWDSSFLGGVVHL

EAGEKVVVRVLDERLVRLRDGTRSYFGAFMV.

The nucleic acid molecule is introduced into a tumor by a nucleic acid delivery system, e.g., a viral vector. The viral vector is suitably selected from adenovirus, adeno-associated virus, lentivirus, and retrovirus.

The nucleic acid molecule is introduced directly into a tumor or is introduced adjacent to a tumor.

Cancer metastasis is reduced by stimulation of cytotoxic T-lymphocytes, and/or by stimulation of production of chemokines, adhesion molecules, and costimulatory molecules for priming naïve T-cells.

A method of reducing cancer metastasis includes the steps of:
   (a) obtaining cells from a tumor from an individual diagnosed with cancer;
   (b) introducing a nucleic acid molecule encoding mutant LIGHT or a fragment thereof into the cells, wherein the mutant LIGHT does not have a proteolytic site;
   (c) culturing the cells expressing the nucleic acid molecule in a suitable growth medium;
   (d) delivering the cells containing mutant LIGHT into the individual; and
   (e) reducing cancer metastasis by stimulating activation of T-cells against tumor cells.

Cells are delivered to a pre-existing tumor site, and/or to a site distal to a pre-existing tumor site. The delivered cells are in the concentration range of about 10,000 to about 1,000,000 cells per dose. Cells may be delivered after the removal of a tumor, and/or prior to the removal of a tumor.

The cancer types treated include breast cancer, lung cancer, prostrate cancer, colon cancer, and skin cancer.

A method of inducing tumor-specific T-cell generation to control metastasis includes the steps of:

(a) introducing a nucleic acid molecule encoding mutant LIGHT or a fragment thereof into an individual at a tumor site, wherein the mutant LIGHT does not have a proteolytic site; and (b) controlling metastasis by inducing T-cell generation, wherein the T-cells destroy initiation of metastasis.

T-cells are activated within a tumor site, and may circulate in blood. Circulating T-cells are preferably cancer specific. The nucleic acid is introduced into a tumor cell in vitro and the tumor cell expressing the nucleic acid is delivered into the individual in vivo. The T-cell generation may be CD8+ dependent.

A therapeutic vaccine includes a tumor cell expressing a mutant LIGHT molecule, wherein the mutant LIGHT is resistant to protease digestion. In the embodiments, the mutant LIGHT molecule does not contain a proteolytic site selected from EQLI (SEQ ID NO: 17) and EKLI (SEQ ID NO: 4). The tumor cell expresses a mutant LIGHT including the extracellular domain of native LIGHT that is resistant to protease digestion. The mutant LIGHT does not include the proteolytic site selected from EQLI (SEQ ID NO: 17) or EKLI (SEQ ID NO: 4) of native LIGHT protein. The proteolytic site may be mutated to render it resistant to protease digestion.

Tumor cells number about 10,000 to about 1,000,000 cells per vaccine dose.

An isolated tumor cell is described that expresses a protease digestion resistant form of mutant LIGHT. The mutant LIGHT may be expressed on the surface of the tumor cell.

A genetic construct includes a mutant LIGHT nucleotide sequence, wherein the nucleotide sequence encodes a mutant LIGHT that is resistant to protease digestion, and the mutant LIGHT is adequate to generate tumor-specific T-cells.

An isolated recombinant nucleic acid includes a nucleotide sequence encoding a protease digestion resistant mutant LIGHT. An embodiment of the nucleotide sequence is: (SEQ ID NO: 2) ATGGAGGAGAGTGTCGTACGGCCCT-CAGTGTTTGTGGTGGATGGACAGACCGACAT CCCATTCACGAGGCTGGGACGAAGCCAC-CGGAGACAGTCGTGCAGTGTGGCCCGGG TGGGTCTGGGTCTCTTGCTGTTGCT-GATGGGGGCTGGGCTGGCCGTCCAAGGCTGGT TCCTCCTGCAGCTGCACTGGCGTCTAG-GAGAGATGGTCACCCGCCTGCCTGACGGAC CTG-CAGGCTCCTGGGAGCAGCTGATACAA-GAGCGAAGGTCTCACGAGGTCAACCCA GCAGCGCATCTCACAGGGGCCAACTC-CAGCTTGACCGGCAGCGGGGGGCCGCTGTT ATGG-GAGACTCAGCTGGGCCTGGCCTTCCT-GAGGGGCCTCAGCTACCACGATGGGG CCCTTGTGGTCACCAAAGCTGGCTAC-TACTACATCTACTCCAAGGTGCAGCTGGGCG GTGTGGGCTGCCCGCTGGGCCTGGCCAG-CACCATCACCCACGGCCTCTACAAGCGC ACAC-CCCGCTACCCCGAGGAGCTGGAGCTGT-TGGTCAGCCAGCAGTCACCCTGCGG ACGGGCCACCAGCAGCTCCCGGGTCTG-GTGGGACAGCAGCTTCCTGGGTGGTGTGG TACAC-CTGGAGGCTGGGGAGAAGGTGGTCGTC-CGTGTGCTGGATGAACGCCTGGTT CGACTGCGTGATGGTACCCGGTCTTACT-TCGGGGCTTTCATGGTGTGA, wherein the sequence encoding the protease digestion site GAGCAGCTGATA (SEQ ID NO: 24) is mutated.

BRIEF DESCRIPTION OF THE DRAWINGS

FIG. 6 A. illustrates increased LTβR-associated chemokines and adhesion molecules in Ag104L$^d$-mutant LIGHT tumors. (1) $5 \times 10^6$ Ag104L$^d$, (2) Ag104L$^d$-B7.1 or (3) Ag104L$^d$-mutant LIGHT tumor cells were inoculated subcutaneously into C3B6F1 or B6/RAG-1$^{-/-}$ mice. Tumor tissues were collected 10-14 days post tumor challenge. B. The same amount of tumor tissue was thoroughly ground in the PBS containing protease inhibitors. SLC in the supernatant was measured by ELISA after centrifugation. Ag104L$^d$-mutant LIGHT tumors collected from both C3B6F1 mice and B6/RAG-1$^{-/-}$ mice, as indicated, contained higher level of SLC than the parental tumors. C. Tumor tissues from Ag104L$^d$, Ag104L$^d$-B7.1 or Ag 104L$^d$-mutant LIGHT were fixed in 10% neutral formalin, sectioned and stained with anti-murine SLC followed by second step antibody, color development (red) is shown by arrows; background was hemotoxilyn counter-stained (blue). D. Total RNA was isolated from the tumor tissue and real-time quantitative RT-PCR was performed to analyze the expression of adhesion molecule MAdCAM-1 and chemokine SLC. E. Gene array was performed to analyze the expression of other chemokines as indicated in the mutant LIGHT-expressing Ag104L$^d$ and parental tumor using total RNA purified from the tumor tissue. The increase of LTβR-associated chemokines and adhesion molecules was found in the Mutant LIGHT-expressing tumor tissues. Relative expression levels were shown in the left panel. Fold of increase of expression by Ag 104L$^d$-mutant LIGHT was shown in the right panel. Total RNA was isolated from the tumor tissue and gene array was performed to analyze the expression of chemokines as indicated in the mutant LIGHT-expressing Ag104L$^d$ and parental tumor.

FIG. 8 shows that intra-tumor injection of mutant LIGHT-expressing Ag104L$^d$ eradicates established parental tumors. 10$^5$ Ag104L$^d$ tumor cells were inoculated to C3B6F1 mice followed by intra-tumor injection of 10$^6$ mutant LIGHT-expressing tumor cells or PBS as control as indicated 14 days after challenge of parental tumor. Ag104L$^d$ tumors treated with Ag104L$^d$-mutant LIGHT were rejected while the ones treated with PBS grew progressively.

FIG. 9 shows a nucleic acid sequence (SEQ ID NO: 3) that encodes a LIGHT protein. The start codon ATG is indicated in bold and the region encoding a proteolytic site that has been deleted in mutant LIGHT is underlined.

FIG. 21 shows increased LTβR-regulated chemokines and adhesion molecules in Ag104L$^d$-LIGHT tumors. C3B6F1 and B6-Rag1$^{-/-}$ mice were inoculated subcutaneously with Ag104L$^d$, Ag104L$^d$-LIGHT and Ag104L$^d$-B7-1 tumor cells (C3B6F1 mice, $5\times10^6$ cells, B6-Rag1$^{-/-}$ mice, $1\times10^6$ cells), and tumor tissues were collected 10-14 d after challenge. (a) Expression of CCL 21 measured by quantitative RT-PCR on total RNA derived from three independent LIGHT-expressing Ag104L$^d$ tumors and three parental tumors (b) CCL 21 in homogenates from Ag104L$^d$-LIGHT tumors or parental tumors, collected from both C3B6F1 mice and B6 Rag1$^{-/-}$ mice and assayed by ELISA. (c) immunohistochemical staining of CCL21 and a hematoxylin counterstain in tissues from Ag104L$^d$, Ag104L$^d$-LIGHT and Ag104L$^d$-B7-1 tumors. (d) Relative expression of chemokines in LIGHT-expressing Ag104L$^d$ and parental tumors. Total RNA was isolated from tumor tissue and gene array analysis was done to assess chemokine expression. (e) Expression of MAdCAM-1 measured by quantitative RT- PCR on total RNA derived from three independent LIGHT-expressing Ag104L$^d$ tumors and three parental tumors.

DETAILED DESCRIPTION

Figure 1:
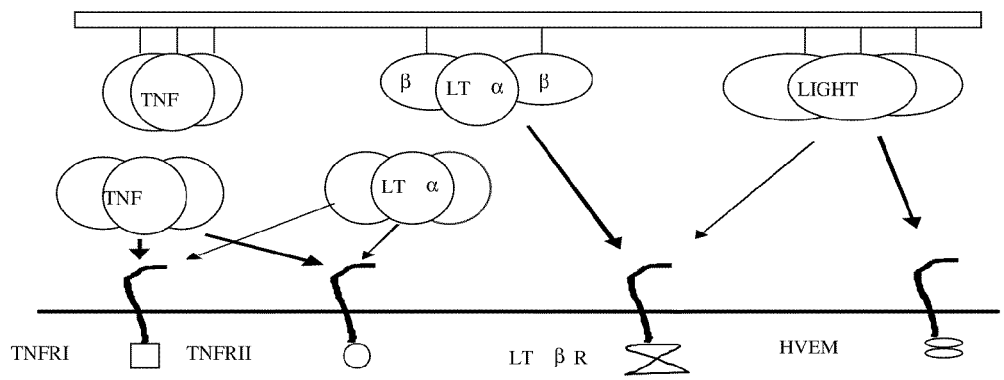
FIG. 1 illustrates a current model for the interactions between TNF/LT/LIGHT family members. LTβR binds to both membrane LT and LIGHT, while HVEM binds to LIGHT. Soluble TNF3 and LTα3 bind to TNFRI and TNFRII.

Expression of mutant LIGHT on tumor cells promotes tumor rejection. The tumor Ag104A and its derivatives were used as one of tumor models. Ag104A was originally derived from spontaneous osteosarcoma in C3H(H-2$^k$) mice and even very low dose of Ag104A (104) can grow aggressively in C3H or B6C3F1 mice with very little infiltrates. When strong antigen, L$^d$, was introduced into a tumor, the tumor remained resistant to immune recognition, suggesting a possible strong tumor barrier. Ag 104L$^d$ tumor transfected retrovirally with mutant LIGHT stably expresses mutant LIGHT on its surface.

Mutant LIGHT-Ag104L$^d$ tumor was first inoculated into B6C3F1 mice for 2 weeks, then 1×10$^6$ 2C T cells were transferred into the established tumor bearing mice. Impressively, all established Mutant LIGHT-AG104L$^d$ tumors (10/10) were rejected one week after the transfer of 2C T cells while no Ag104L$^d$ tumors (0/10) were rejected. Even though B7-1 is a strong costimulatory molecule for inducing T cell activation and expansion, in contrast to mutant LIGHT, expression of B7-1 on Ag 104L$^d$ was not sufficient for the rejection of a tumor. These data suggest that mutant LIGHT is more potent than B7-1 to break tumor tolerance. Considering the dual effect of mutant LIGHT, local expression of mutant LIGHT at the tumor site may attract dendritic cells and T cells across the tumor "barrier" by regulating the expression of lymphoid tissue chemokines and adhesion molecules. Furthermore, local expression of mutant LIGHT becomes a strong costimulatory molecule that enhances direct presentation of tumor antigens to antigen-specific T cells and prevent the anergy of infiltrated T cells within the tumor microenvironment. H-2b background tumors, MC57 tumors (fibrosarcoma), MC57-L$^d$ and MC57-SIY with or without mutant LIGHT expression have been generated and are used in B6 mouse models, including LTβR, mutant LIGHT, and HVEM KO mice to further characterize the role of mutant LIGHT and its receptors in tumor immunity. Mutant LIGHT appears to have multiple functions in mediating tumor immunity. Mutant LIGHT also may enhance tumor apoptosis in vivo. Interestingly, intratumoral injection of cDNA encoding mutant LIGHT induced an antigen-specific cytolytic T-cell response and therapeutic immunity against the established murine tumor P815.

Successful eradication of metastasis by currently available cancer treatments remains rare. Generating immune responses in primary tumor tissues prior to surgical resection produces tumor-specific effector T cells sufficient to eradicate distant metastases. Adenovirus expressing TNF superfamily 14 (Ad-TNFSF14, mutant LIGHT) was inoculated into primary 4T1 mammary carcinoma in mice subsequent to its systemic dissemination. Metastases were eradicated in a CD8-dependent fashion. Local treatment with Ad-TNFSF14 initiated priming of tumor-specific CD8$^+$ T cells directly in the primary tumor, with subsequent exit of cytotoxic T lymphocytes (CTL) that homed to distal tumors. Targeting primary tumor with Ad-TNFSF14 prior to surgical excision elicits immune-mediated eradication of spontaneous metastasis.

Metastasis is often a fatal step in the progression of solid malignancies. Disseminated metastatic tumor cells can remain dormant and clinically undetectable for months or even years following surgical resection of the primary tumor, leading to subsequent clinical disease recurrence. Immunotherapeutic strategies are suitable to eliminate this micrometastatic disease. Local delivery of mutant LIGHT into the primary tumor prevented the formation of metastasis and rejected the established metastasis in peripheral tissues. Local delivery of mutant LIGHT inside tumor using adenoviral gene transfer generated sufficient number of effector/memory T cells from the tumor tissues that move to a distal site, leading to an overall increase in the intensity of the immune response, greater inflammatory cytokine production, and the eradication of spontaneous metastasis. Immunotherapy using primary tumor tissues aimed to provoke and sustain a tumor specific immune response in the presence of endogenous tumor antigens generates the necessary CTL to clear already disseminated tumor cells.

In an aspect, adenoviral vectors form a suitable delivery system for gene therapy against tumors. For example, adenoviral vectors have a favorable safety profile; higher transduction efficiency; expression in non-dividing cells; and direct stimulation of innate immunity that contributes to stronger adaptive immunity. Although the adenoviral backbone may stimulate an immune response due to its strong antigenicity, this does not appear to impede repeated injections by the intratumoral route. As disclosed herein, local administration demonstrate that the adenovirus delivers LIGHT into tumor cells, leading to a strong antigen specific immune response sufficient to reject metastactic cells. Other viral gene delivery systems such as lentivirus, vaccinia virus, adeno-associated virus (AAV), moloney murine leukemia virus (MoMuLV); VSV-G type retroviruses, papovaviruses such as JC, SV40, polyoma, Epstein-Barr Virus (EBV); papilloma viruses, and bovine papilloma virus type I, and other human and animal viruses are also suitable.

Figure 14:
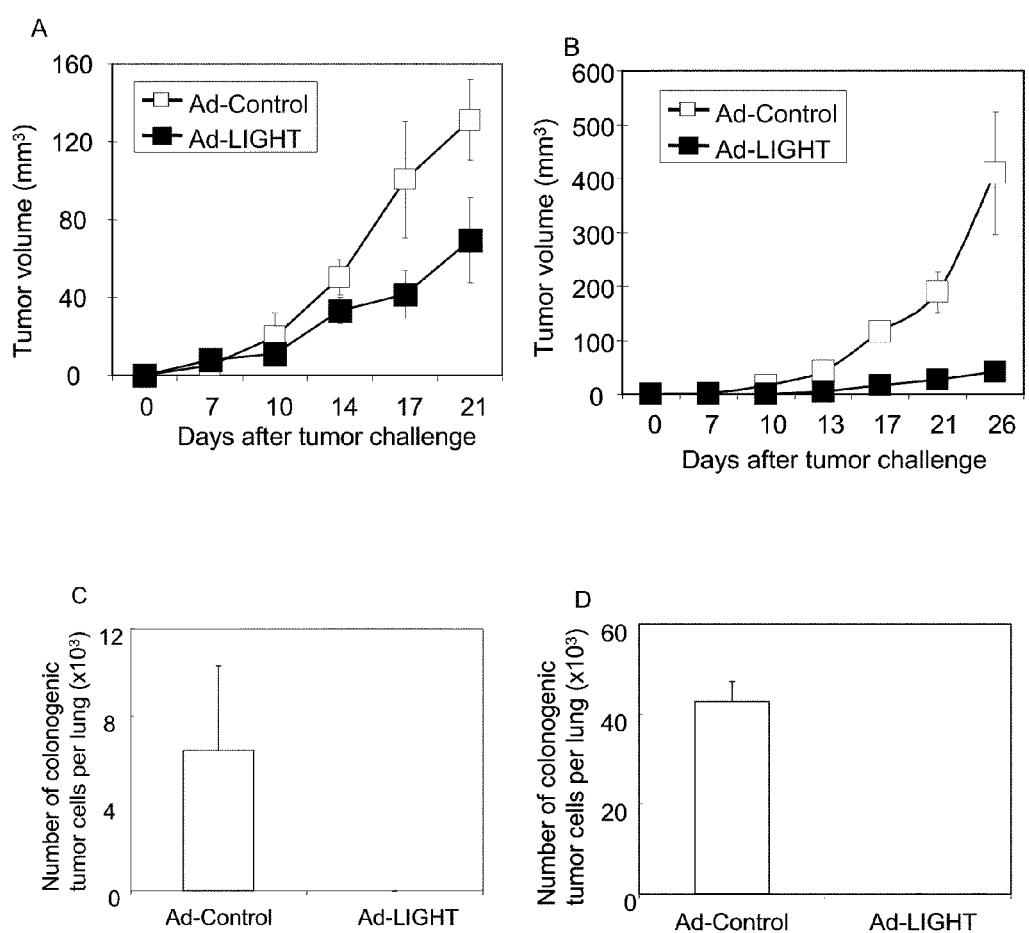
FIG. 14 demonstrates that Ad-mutant LIGHT treatment controls spontaneous metastasis. A. Tumor growth curve by the effects of Ad-mutant LIGHT on the primary 4T1 mammary carcinoma. 1×10$^5$ cells of 4T1 cells were injected subcutaneously into the flank of Balb/C mice on day 0.7 days later, 5×10$^9$ PFU of Ad-mutant LIGHT (black square) or Ad-control (white square) was intratumorally administered and tumor growth was continually monitored. Data is given as tumor volume (mean±SD). The data is representative of two independent experiments with similar results. B-C. Local expression of mutant LIGHT on 4T1 tumor cells prevents the development of spontaneous metastasis. In vitro cultured 4T 1 mammary carcinoma (1×10$^6$ cells) were infected with Ad-mutant LIGHT or Ad-Control (4×10$^8$ PFU/ml) for 24 hours then injected with 1×10$^5$ cells subcutaneously in the flank of Balb/c mice. Tumor growth was monitored (B) until mice were sacrificed on day 35 post tumor inoculation for lung colonogenic assay (C). Data is a representative of two experiments. D. Intratumoral injection of Ad-mutant LIGHT into 4T1 cells prevents the spread of metastasis. $1\times10^5$ cells of 4T1 mammary carcinoma cells were injected subcutaneously into the flank of Balb/c mice. On Day 7 post tumor inoculation, Ad-mutant LIGHT or Ad-Control ($5\times10^9$ PFU) was injected intratumorally. Primary tumor was surgically removed on Day 18 and mice were sacrificed on Day 35 post tumor inoculation for lung colonogenic assay. Data is representative of two independent experiments.
Figure 15:
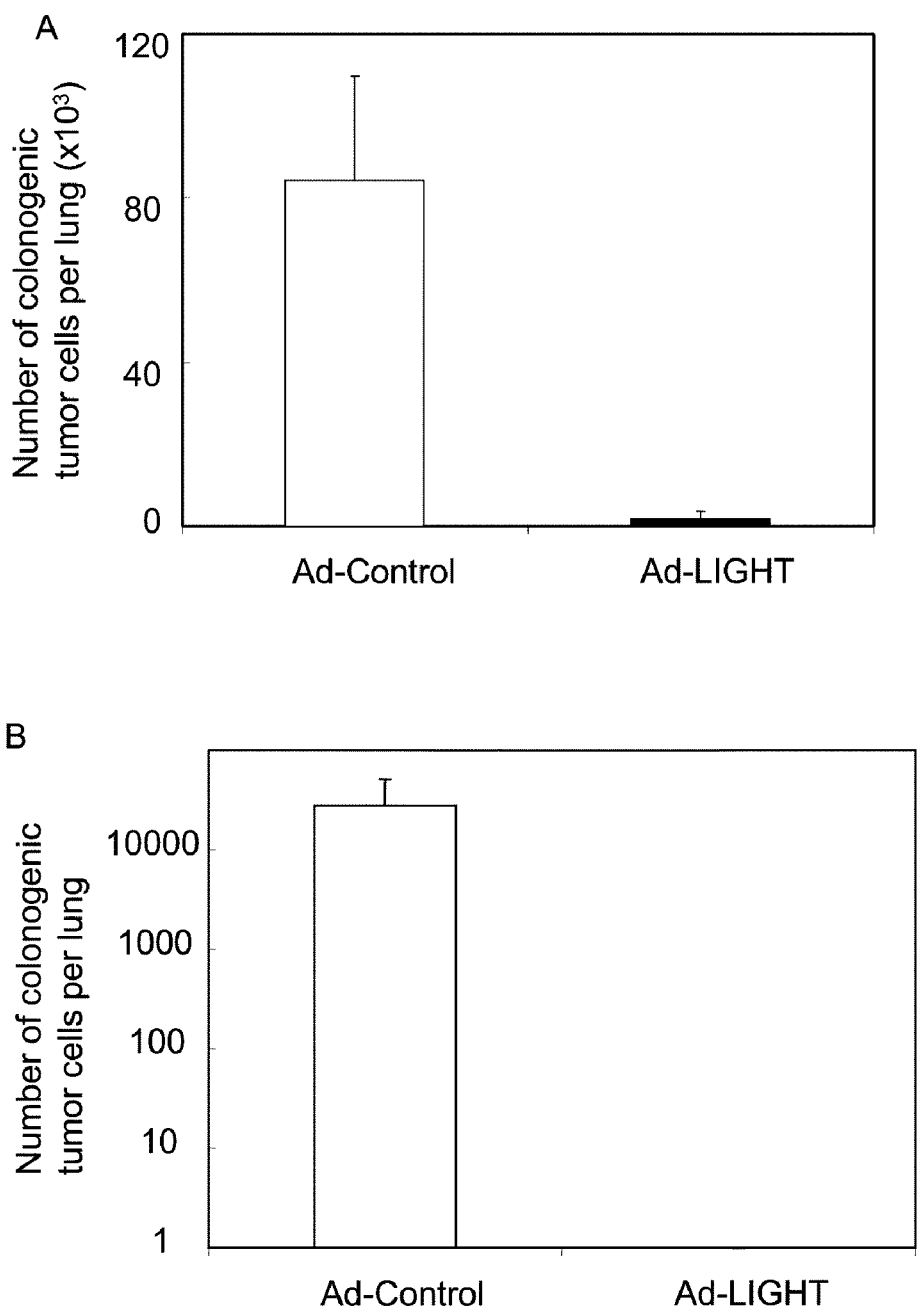
FIG. 15 shows that Ad-mutant LIGHT treatment eradicates established metastasis. A. 4T1 mammary carcinoma cells injected subcutaneously in the flank of Balb/c mice were treated with Ad-mutant LIGHT or Ad-control ($2\times10^9$ PFU) intratumorally on days 14 and 17 post tumor inoculation. Primary tumors (~150 mm$^3$) were surgically resected on Day 28 and mice were sacrificed for colonogenic lung assay on day 35. Data is a representative of three experiments. B. Vaccination with irradiated autologous tumor cells eradicates established metastasis. $6\times10^4$ cells of 4T1 tumor cells were inoculated subcutaneously in the flank of Balb/c mice on day 0. Primary tumors were surgically removed on day 18 followed by subcutaneous injection with Ad-mutant LIGHT or Ad-Control ($4\times10^9$ pfu) infected and irradiated 4T1 cells ($1\times10^6$ cells) in the mammary fat pad. On day 21, a second vaccination of freshly prepared cells were injected in the mammary pad of mice. Mice were sacrificed on day 45 post tumor inoculation and analyzed by the lung colonogenic assay. Data is representative of two independent experiments.

Clearance of distal metastases are attributable to the effects of mutant LIGHT in the primary tumor, rather than a general systemic immune stimulation by the adenovirus expressing mutant LIGHT. For example, 4T1 tumor cells infected with Ad-mutant LIGHT in vitro resulted in no metastasis. In this model, any remaining viral excess was washed out prior to inoculation of mutant LIGHT infected 4T1 tumor cells, thus rendering systemic stimulation by Ad-mutant LIGHT impossible (FIG. 14). 4T1 tumor cells infected with Ad-mutant LIGHT as therapeutic vaccine led to the eradication of metastasis (FIG. 15). Highly progressive tumor cells stably transfected with mutant LIGHT mediated rejection of distal tumors completely (FIG. 17). Inoculation of Ad-mutant LIGHT outside of the primary tumor failed to prevent lung metastasis. Targeting the primary tumor with Ad-mutant LIGHT effectively breaks tolerance of T cells, and promotes antigen specific CTLs to exit the primary tumor to clear metastasis or distal tumors.

4T1 mouse mammary carcinoma is a poorly immunogenic, BALB/c-derived transplantable tumor model that shares many characteristics with human cancers including breast cancers, and is an established model for metastatic cancers. When 10$^5$ tumor cells are inoculated subcutaneously, the tumor begins to metastases to draining lymph nodes (LN), lung, liver, and other organs only 11 days post inoculation. Mice succumb to lung metastases within 5-7 weeks. Local treatment of 4T1 with Ad-mutant LIGHT on day 14, eradicated established metastatic cells in the peripheral tissues. With surgical excision of the primary tumor a week subsequent to dissemination of cancer cells, tumor vaccination with Ad-mutant LIGHT eliminates metastases. Ad-mutant LIGHT either alone or in combination with other treatments may augment the immune response to elicit complete eradication of the more established metastases in the periphery.

It had not been clearly demonstrated whether tumor specific CTLs that infiltrate the tumor site can survive to vacate the tumor and enter the draining lymphoid organs for systemic circulation. A unique tumor model, the 2C-Ag104$L^d$ system was used to trace antigen-specific T cells inside the primary tumor, the draining LN, and secondary tumor sites. The uniqueness of the model system is that the antigen $L^d$ expressed by the tumor cells can only be seen by 2C T cells directly since the $L^d$ processed and presented by the antigen presenting cells (APC) from a H-2b host can not be recognized by 2C T cells. Ag104$L^d$ tumor cells inside draining LN that directly prime 2C T cells in the lymphoid tissues were not identified. Therefore, few naïve 2C T cells are activated in the draining lymph nodes in this setting. Rather, 2C T cells must move into the tumor site for direct encounter with the $L^d$-expressing tumor cells for initial activation, and antigen-experienced T cells present in the lymphoid organs come from the tumor microenvironment in this model system. In the presence of LIGHT inside the tumor, CTLs are efficiently primed and subsequently circulate to infiltrate LIGHT-negative distal tumors. Without the benefits of LIGHT expression in the primary tumor, few activated T cells were detected in draining LNs or at a secondary tumor site. It is likely that these effector/memory T cells generated in the local tumor site in the presence of LIGHT are able to exit the tumor and patrol the periphery and identify metastatic tumor cells. Chemokine receptor (CCR7) has been recently shown to be a key molecule for T cells to exit the peripheral tissues, including the inflammatory site, and traffic to the draining LN. The 2C T cells exiting LIGHT-expressing tumors may be controlled by CCR7.

The model system disclosed herein allows to distinguish the tumor antigen-specific T cells activated in the lymphoid tissues before going to the tumor versus those activated directly within the tumor microenvironment and also examines the trafficking of the tumor antigen-specific CD8$^+$ T cells in the primary tumor after local immunotherapy.

"Mutant LIGHT" also designated as "LIGHT$^m$" relates to a LIGHT protein or LIGHT protein derived peptides or fragments that are resistant to protease digestion or otherwise are capable of being stably expressed on the surface of cells including tumor cells, so that increased tumor-specific T-cells are generated, as compared to a native LIGHT protein. There are several ways to generate mutant LIGHT. For example, the protease site (e.g., EQLI (SEQ ID NO: 17) or EKLI (SEQ ID NO: 4)) can be mutated either to remove the protease site in toto or to render the site resistant to protease digestion by changing (e.g., insertion, deletion, substitution) one or more amino acids at the protease site. Mutant LIGHT also includes fragments/derivatives of LIGHT protein that are resistant to protease digestion thereby exhibiting the ability to be present on the cell surface for an extended period of time compared to native LIGHT protein.

For example, an extracellular domain of LIGHT molecule can be recombinantly expressed such that either the recombinant form does not have the proteolytic site all together or has one or more amino acid changes that renders the recombinant form protease digestion resistant (mutant LIGHT). In addition, the extracellular domain or a functional equivalent derivative of the extracellular domain of LIGHT can be linked to a tether or linker or spacer sequence to anchor the extracellular domain in the membrane of tumor cells.

"Ad-mutant LIGHT" refers to recombinant adenoviral vector system that contains mutant LIGHT encoding nucleic acids and is suitable for delivering the nucleic acid sequences to a tumor site or capable of infecting tumor cells.

"Metastasis or metastases" refers to the process by which cancer spreads from the location at which the cancer initiated as a tumor to one or more distant locations in the body by migration of one or more cancerous cells. These terms also include micro-metastasis wherein the formation of tumors at distal locations correspond to small aggregates of cancer cells that are visible microscopically. These terms also refer to the secondary cancerous growth resulting from the spread of the primary tumor from the original location.

"Reducing or controlling metastasis" refers to a reduction in the number of metastatic tumor sites as compared to a control.

"Adoptive transfer" refers to the transfer of T cells into recipients.

"Tumor" refers to an abnormal mass of tissue. Tumors can be benign or malignant. Malignant tumors are cancerous.

"Cancer or cancerous" refers to an abnormal growth of cells that tend to proliferate in an uncontrolled way and, in some cases, metastasize (spread).

"Tumor site" means a location in vivo or ex vivo that contains or is suspected of containing tumor cells. Tumor site includes solid tumors and also the locations that are adjacent or immediately near a tumor growth.

As used herein, the term "administration" refers to systemic and/or local administration. The term "systemic administration" refers to non-localized administration such that an administered substance may affect several organs or tissues throughout the body or such that an administered substance may traverse several organs or tissues throughout the body in reaching a target site. For example, administration into a subject's circulation may result in expression of a therapeutic product from an administered vector in more than one tissue or organ, or may result in expression of a therapeutic product from an administered vector at a specific site, e.g., due to natural tropism or operable linkage of tissue-specific promoter elements. One of skill in the art would understand that various forms of administration are encompassed by systemic administration, including those forms of administration encompassed by parenteral administration such as intravenous, intramuscular, intraperitoneal, and subcutaneous administration. In some embodiments, systemic administration can be used to elicit a systemic effect associated with treatment of a local or systemic disease or condition. A systemic effect may be desirable for a local disease or condition, for example, to prevent spread of said disease or condition. The term "local administration" refers to administration at or near a specific site. One of skill in the art would understand that various forms of administration are encompassed by local administration, such as direct injection into or near a specific site. In some embodiments, local administration is associated with treatment of a disease or condition where a local effect is desired (e.g. administration to the lung for the treatment of lung cancer). A local effect may be desired in association with either local or systemic diseases or conditions. A local effect may be desired in association with a systemic disease or condition to treat a local aspect of a systemic disease or condition.

Specific viral vectors for use in gene transfer systems are now well established and include adenoviral vectors, adeno-associated viral vectors, lentiviral vectors, baculoviral vectors, Epstein Barr viral vectors, papovaviral vectors, vaccinia viral vectors, and herpes simplex viral vectors. See for example: Madzak et al. (1992): papovavirus SV40; Moss et al. (1992): vaccinia virus; Margulskee (1992): herpes simplex virus (HSV) and Epstein-Barr virus (EBV); Miller, (1992): retrovirus; Brandyopadhyay et al., (1984): retrovirus; Miller et al. (1992): retrovirus; Anderson, (1992): retrovirus; herpes viruses (for example, herpes simplex virus based vectors); and parvoviruses (for example, "defective" or non-autonomous parvovirus based vectors); Hofmann, et al. (1995): baculovirus; Boyce, et al. (1996): baculovirus; all of which are herein incorporated by reference. In various embodiments, recombinant viral vectors designed for use in gene therapy are used in the invention. See, e.g., Hu and Pathak, (2000); Somia and Verma (2000); van Beusechem et al. (2000); Glorioso et al. (2001). Additionally, viral vectors may be administered in combination with transient immunosuppressive or immunomodulatory therapies. See, e.g., Jooss et al. (1996); Kay et al. (1994).

In other embodiments, viral serotypes, e.g., the general adenovirus types 2 and 5 (Ad2 and Ad5, respectively) may be administered, possibly on an alternating dosage schedule where multiple treatments will be administered. Specific dosage regimens may be administered: over the course of several days, when an immune response against the viral vector is anticipated, or both. In non-limiting examples of specific embodiments, Ad5-based viral vectors may be used on day 1, Ad2-based viral vectors may be used on day 2, or vice versa.

In some embodiments, nucleic acids are additionally provided in replication-defective recombinant viruses or viral vectors. These can be generated in packaging cell lines that produce only replication-defective viruses. In certain embodiments, the nucleic acid encoding a therapeutic gene product is not part of a viral vector.

Adenoviral vectors: In some embodiments, a vector for delivering a nucleic acid is an adenovirus-based vector. See, e.g., Berkner et al. (1992). In some embodiments, the adenovirus-based vector is an Ad-2 or Ad-5 based vector. See, e.g., Muzyczka (1992); Ali et al. (1994); and U.S. Pat. Nos. 4,797,368 and 5,399,346.

Adenoviruses can be modified to efficiently deliver a therapeutic or reporter transgene to a variety of cell types. For example, the general adenoviruses types 2 and 5 (Ad2 and Ad5, respectively), which cause respiratory disease in humans, are currently being developed for clinical trials, including treatment of cancer or other cell proliferation diseases and disorders, and for gene therapy of Duchenne Muscular Dystrophy (DMD) and Cystic Fibrosis (CF). Both Ad2 and Ad5 belong to a subclass of adenovirus that are not associated with human malignancies. Adenovirus vectors are capable of providing high levels of transgene delivery to diverse cell types, regardless of the mitotic state of the cell. High titers ($10^{13}$ plaque forming units/ml) of recombinant virus can be easily generated in 293 cells (an adenovirus-transformed, complementation human embryonic kidney cell line: ATCC No. CRL1573) and cryo-stored for extended periods without appreciable losses. The efficacy of this system in delivering a therapeutic transgene in vivo that complements a genetic imbalance has been demonstrated in animal models of various disorders. See, e.g., Watanabe (1986); Tanzawa et al. (1980); Golasten et al. (1983); Ishibashi et al. (1993); Ishibashi et al. (1994), all of which are herein incorporated by reference. Recombinant replication defective adenovirus encoding a cDNA for the cystic fibrosis transmembrane regulator (CFTR) gene product has been approved for use in at least two human CF clinical trials. See, e.g., Wilson (1993).

Some replication-deficient adenoviruses which have been developed for clinical trials contain deletions of the entire E1a region and part of the E1b region. These replication-defective viruses are grown in 293 cells containing a functional adenovirus E1a gene which provides a trans-acting E1a protein. E1-deleted viruses are capable of replicating and producing infectious virus in certain cells (e.g., 293 cells), which provide E1a and E1b region gene products in trans. The resulting virus is capable of infecting many cell types and can express the introduced gene (providing it carries its own promoter). However, the virus cannot replicate in a cell that does not carry the E1 region DNA unless the cell is infected at a very high multiplicity of infection. Other adenoviral vectors developed for clinical trials may be used in the invention. Examples include Ad vectors with recombinant fiber proteins for modified tropism (e.g., van Beusechem et al. (2000)), protease pre-treated viral vectors (e.g., Kuriyama et al. (2000)), E2a temperature sensitive mutant Ad vectors (e.g., Engelhardt et al. (1994)), and "gutless" Ad vectors (e.g., Armentano et al. (1997); Chen et al. (1997); Schieder et al. (1998)).

Adenoviruses have a broad host range, can infect quiescent or terminally differentiated cells such as neurons, and appear to be essentially non-oncogenic. Adenoviruses additionally do not appear to integrate into the host genome. Because they exist extrachromosomally, the risk of insertional mutagenesis is greatly reduced. See, e.g., Ali et al. 1994, supra, at 373. Recombinant adenoviruses (rAdV) produce very high titers, the viral particles are moderately stable, expression levels are high, and a wide range of cells can be infected.

Adeno-associated viruses (AAV) have also been used as vectors for somatic gene therapy. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep 62 and rep 40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene. See, e.g., Carter (1990). It has been shown that the ITRs represent the minimal sequence required for replication, rescue, packaging, and integration of the AAV genome.

Administration of the viral particles comprising viral vectors described herein can be via any of the accepted modes of administration for such viral particles well known by a person of ordinary skill in the art. For example, the viral particles may be administered by systemic or local administration, including oral, nasal, parenteral, transdermal, topical, intraocular, intrabronchial, intraperitoneal, intravenous, subcutaneous, and intramuscular administration, or by direct injection into cells, tissues, organs, or tumors. The adenoviral particles/vectors may be formulated in any art-accepted formulation well known to a person of ordinary skill in the art.

EXAMPLES

The following examples are for illustrative purposes only and are not intended to limit the scope of the disclosure.

Example 1

Figure 2:
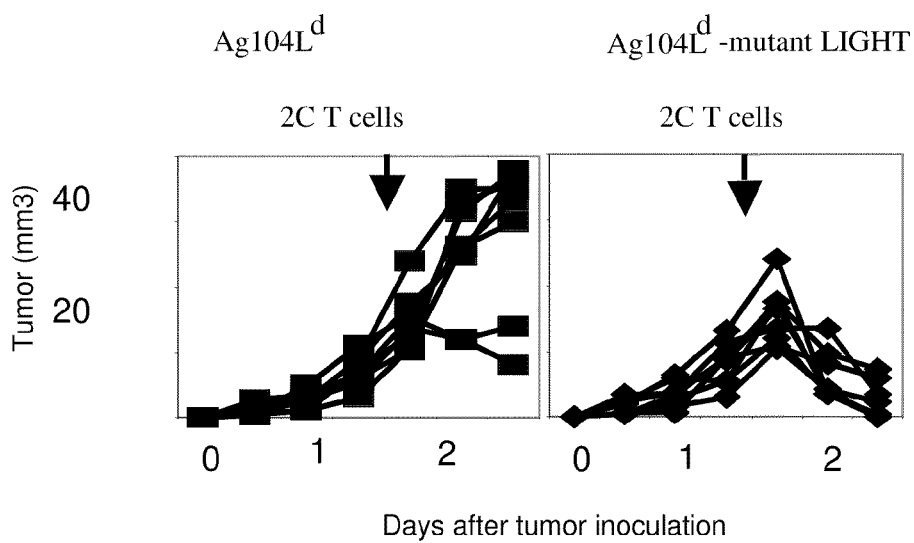
FIG. 2 shows that both mutant LIGHT and antigen specific T cells are required for optimal tumor rejection. Tumor cells ($5 \times 10^5$) were inoculated into CB6F1: Tumor transfected with mutant LIGHT on the left side and control tumor on the right side. Fourteen days later, 2C T cells ($10 \times 10^5$) were transferred into the mice and tumor growth was monitored. Tumor growth curves are shown.
Figure 3:
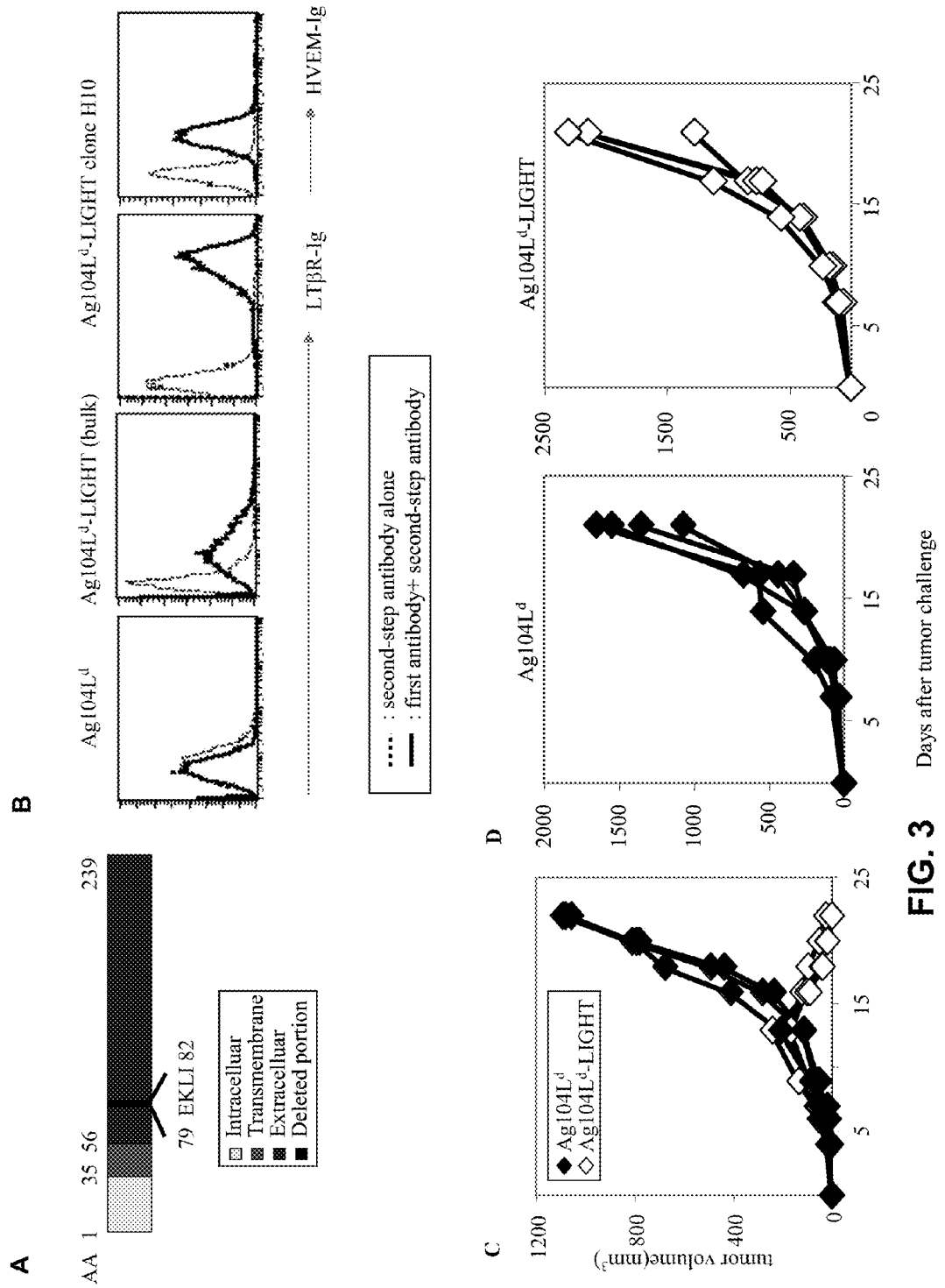
FIG. 3 shows the growth kinetics of mutant LIGHT-expressing Ag104L$^d$ and parental tumor in C3B6F1 and B6/RAG-1$^{-/-}$ mice. A. Four amino acids (SEQ ID NO: 4) corresponding to a proteolytic site were deleted from the extracellular domain of LIGHT to ensure stable expression on the surface of tumor cells. B. Ag104L$^d$ parental tumor cells, Ag104L$^d$ tumor cells transfected with mutant LIGHT, as bulk or cloned, were stained with LTβR-human Ig, HVEM-murine Ig, followed by FITC-conjugated donkey antibody against human IgG or goat antibody against murine IgG, respectively (solid lines). Tumor cells stained with second-step antibody alone were shown in dotted lines. C. C3B6F1 mice were inoculated subcutaneously with $5 \times 10^6$ Ag104L$^d$ parental tumor cells (solid diamonds) or mutant LIGHT-expressing Ag104L$^d$ tumor cells (open diamonds). Ag104L$^d$ grew progressively while Ag104L$^d$-mutant LIGHT was rejected in C3B6F1 mice. D. B6/RAG-1$^{-/-}$ mice were challenged with subcutaneous injection of $10^6$ Ag104L$^d$ tumor cells (solid diamonds) or mutant LIGHT-expressing Ag104L$^d$ tumor cells (open diamonds). Both tumors grew progressively in the B6/RAG-1$^{-/-}$ mice.

Mutant LIGHT Expressed Inside the Tumor Augmented Host Resistance More than 500 Times Fibrosarcoma Ag104L$^d$ was highly tumorigenic and grew out 100% (enlarged tumor growth) when $10^4$ cells were injected into recipient mice C3B6F1 subcutaneously (TABLE 1). It has been reported that 2C T cell receptor (TCR) transgenic mice, which were filled with T cells against antigen L$^d$ expressed on the tumor, failed to eradicate it even after rejection of skin graft containing the same antigen. How to direct tumor-specific T cells into the tumor and activate them at the tumor sites seems to be one critical hurdle for rejection, as well as immunotherapy of cancer clinically. Mutant LIGHT expressed in the tumor environment may break the tolerance by attracting and activating T cells inside the tumor via LTβR and HVEM, respectively, leading to tumor rejection (FIG. 2). To demonstrate this, mutant LIGHT was expressed on this tumor cell line by retroviral transduction utilizing retroviral vector MFG. Initially, native LIGHT expression was not detected on the tumor cell surface after transduction. Because native LIGHT has proteolytic sites in its sequence, which may prevent its stable presence on the surface of a tumor cell line, a mutant version of LIGHT (mutant LIGHT), which reduces proteolysis of LIGHT on the membrane was used. (FIG. 3A). After retroviral transduction of mutant LIGHT/MFG to AG104L$^d$, Mutant LIGHT expression was detected on the surface of transduced tumor cells by LTβR-Ig. (FIG. 3B). These cells were defined as Ag 104L$^d$-mutant LIGHT bulk. Mutant LIGHT-expressing Ag 104L$^d$ tumor cells were further cloned by limiting dilution. One of the clones, H10 was used in most of the experiments unless specified otherwise. Mutant LIGHT was able to bind both of its receptors, LTβR and HVEM. Ag104L$^d$-mutant LIGHT bulk and all the clones tested bound receptors of mutant LIGHT, LTβR and HVEM, shown by their ability to be stained by soluble LTβR and HVEM. The typical staining profile of Ag104L$^d$-Mutant LIGHT bulk and clone H10 by LTβR-Ig and HVEM-Ig was shown (FIG. 3B). The growth of parental tumor cells and mutant LIGHT-transfectants was the same in both tissue culture and RAG-1-/- mice (FIG. 3D). Different number of mutant LIGHT-expressing tumor cells, bulk or clone H10, were inoculated subcutaneously to C3B6F1 mice. The recipients rejected the highest dose of mutant LIGHT-expressing tumor cells injected, 5×10$^6$, which was 500 times of the dose at which the parental tumors grew progressively 100% (Table 1). The typical growth kinetics of the mutant LIGHT-expressing tumor, bulk or clone H10, and the parental one when 5×10$^6$ cells were inoculated was shown in FIG. 3C. Ag104L$^d$-mutant LIGHT grew in the first two weeks after inoculation followed by subsequent regression when parental tumor continues to progress and kill the host in 3-4 weeks (FIG. 3C). The tumor rejection is likely to be mutant LIGHT-dependent since the mutant LIGHT-expressing tumors grew if mutant LIGHT function was blocked with soluble LTβR (Table 1). The tumor rejection is dependent on lymphocytes. Mutant LIGHT-expressing Ag104L$^d$ grew equally progressive as the parental tumor in RAG-1$^{-/-}$ mice, which lacked lymphocytes (FIG. 3D). CD8$^+$ T cells but not CD4$^+$ T cells were essential to mediate the rejection of the mutant LIGHT-expressing Ag104L$^d$ because C3B6F1 mice, which were depleted of CD8$^+$ T cells with anti-CD8 antibody, failed to reject these tumors (TABLE 1). However, CD4$^+$ T cells are not required for the tumor rejection.

Example 2

Mutant LIGHT-Mediated Tumor Environment has More Infiltrating CD8+ T Cells

Figure 5:
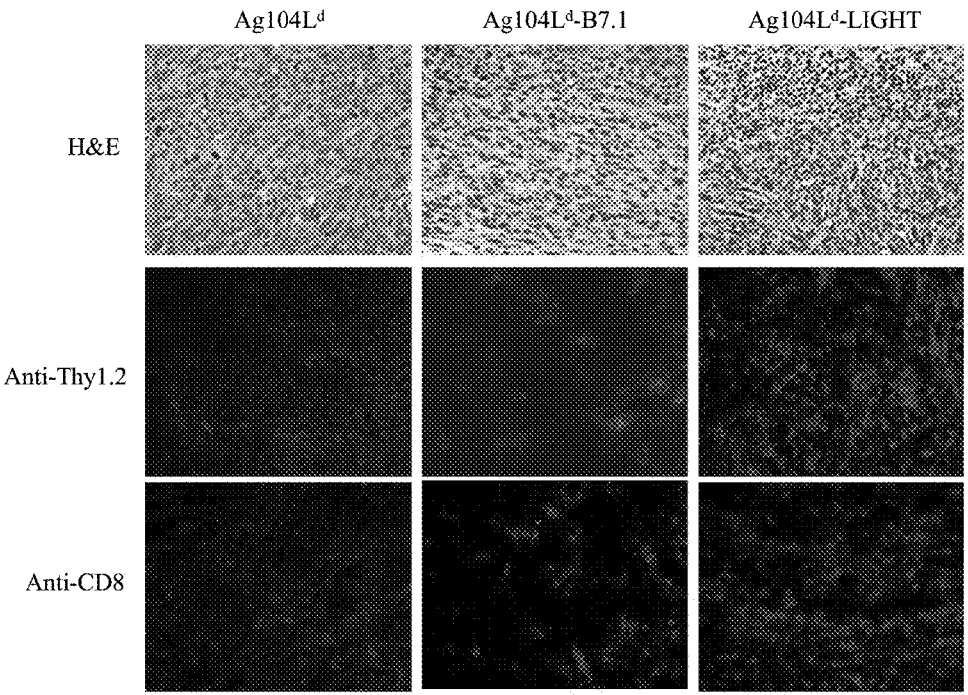
FIG. 5 shows photographic illustrations of increased infiltration of CD8$^+$ T cells in mutant LIGHT-expressing Ag104L$^d$ tumor tissues. $5 \times 10^6$ Ag104L$^d$, Ag104L$^d$-B7.1 or Ag104L$^d$-mutant LIGHT tumor cells were injected subcutaneously to C3B6F1 mice. Tumor tissues were collected 10-14 days after tumor inoculation. Frozen sections of tumor tissues were stained with HE (upper panel) or anti-Th1.2-PE (middle panel), anti-CD8-PE, as indicated (lower panel).

To investigate the possible mechanisms underlying mutant LIGHT-mediated tumor rejection, 5×10$^6$ mutant LIGHT-expressing Ag104L$^d$ or the same number of parental tumor cells were injected subcutaneously to the C3B6F1 mice. Ten to fourteen days after tumor inoculation, before mutant LIGHT-expressing tumors were rejected, tumor tissues were collected. HE-staining of the tumor tissues showed large amount of infiltrating lymphocytes (FIG. 5) while the parental tumors showed very little infiltration (FIG. 5). Immunofluorescent staining confirmed that among the infiltrating lymphocytes, large amount of Thy1.2$^+$ T cells (FIG. 5), especially CD8$^+$ T cells were present inside Mutant LIGHT-expressing tumors (FIG. 5).

Example 3

Modified Extracellular Domain of LIGHT is Sufficient to Co-Stimulate T Cells

Figure 4:
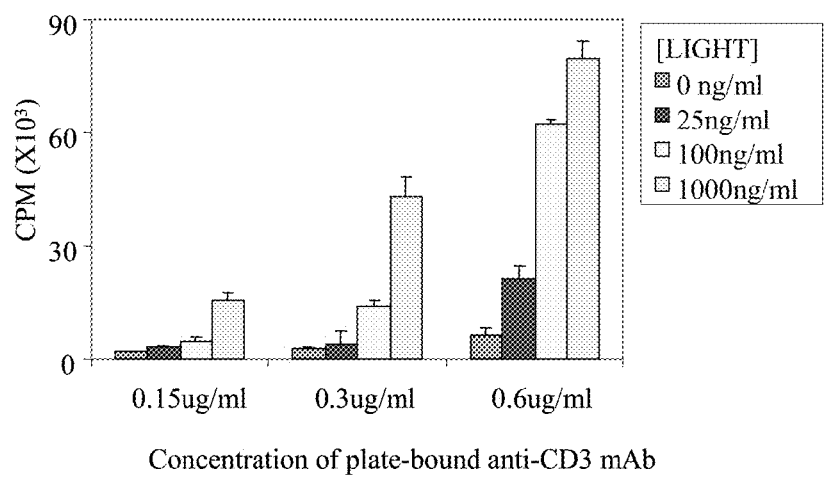
FIG. 4 shows that a modified extracellular domain of mutant LIGHT is sufficient to co-stimulate purified T cell responses. A. Recombinant protein containing an extracellular domain of mutant LIGHT (85-239 amino acids) and a flag sequence to facilitate purification of recombinant protein. B. Purified T cells were stimulated with immobilized extracellular domain of mutant LIGHT in the presence of antibody against CD3 (anti-CD3).

In mutant LIGHT, four amino acids corresponding to a proteolytic site in the extracellular domain, very close to transmembrane domain of the molecule were deleted (FIG. 3A). The mutation in the mutant LIGHT molecule affects its co-stimulatory effect. Recombinant mutant LIGHT protein was made that only contains amino acids 85 to 239, a shortened form of extracellular domain, with a flag peptide to facilitate purification (recombinant mutant LIGHT) (FIG. 4A). The modified extracellular domain of mutant LIGHT was sufficient to co-stimulate T cells. For this test, an in vitro co-stimulation assay with plate-bound recombinant mutant LIGHT was used to stimulate purified mouse T cells in the presence of an immobilized monoclonal antibody against CD3 at a sub-optimal dose. Immobilized recombinant mutant LIGHT strongly stimulated a proliferation of purified mouse T cells in a dose-dependent manner in the presence of sub-optimal amounts of antibody against CD3 (FIG. 4B). The modified extracellular domain of LIGHT, which is amino acid 85 to 239 excluding the proteolytic site deleted from the mutant LIGHT molecule, is sufficient to co-stimulate T-cell growth when engagement of the T-cell receptor occurs.

Example 4

Tumor Expressing B7.1 Molecule Contains Comparable Infiltrating T Cells to Parental Tumor Infiltrating CD8$^+$ T cells correlated with tumor rejection by mutant LIGHT-mediated tumor environment. Because mutant LIGHT has potent co-stimulatory effect on T cells, a question was whether B7.1, another potent co-stimulatory molecule is sufficient to mediate tumor rejection associated with large number of infiltrating T cells. 5×10$^6$ Ag104L$^d$-B7.1 tumor cells, which were transduced the same way as Ag104L$^d$-mutant LIGHT, were inoculated to C3B6F1 mice subcutaneously. These tumors grew progressively in the recipients. HE-staining on the tumor tissues showed little lymphocyte infiltration (FIG. 5). Immunofluoresent staining with anti-Thy1.2 and anti-CD8 revealed that Ag104L$^d$-B7.1 tumor tissues contained comparable level of T cells including CD8$^+$ T cells infiltration with parental tumor Ag104L$^d$ (FIG. 5), which was substantially less comparing with mutant LIGHT-expressing Ag104L$^d$ (FIG. 5). This data was consistent with previous findings that Ag104L$^d$ expressing two co-stimulatory molecules, B7.1 and CD48, failed to be rejected by 2C TCR transgenic mice. These lines of evidence suggested that strong co-stimulation alone is not sufficient to mediate tumor rejection in these tumor models.

Example 5

Mutant LIGHT-Mediated Tumor Environment Contains High Level of Chemokine SLC and Up-Regulated Adhesion Molecule MAdCAM-1

Although mutant LIGHT binds to HVEM, the receptor expressed on T cells, via which mutant LIGHT likely mediates its co-stimulation of T cells, LTβR is another receptor interacting with mutant LIGHT. LTβR signaling is an important regulator for chemokine SLC and adhesion molecule MAdCAM-1, which controls the homing of naïve T cells to the secondary lymphoid tissues. Mutant LIGHT in the tumor environment could interact with LTβR on these tumor stromal cells to up-regulate SLC and MAdCAM-1 in the tumor environment. Tumor tissue was collected from either parental Ag104L$^d$ or Mutant LIGHT-expressing Ag104L$^d$ 10-14 days after inoculation. Real time RT-PCR, showed that Mutant LIGHT-positive tumor mass expressed higher level of SLC than parental tumor (FIG. 6A). This result was independently confirmed by ELISA detecting abundance of SLC in Ag104L$^d$-Mutant LIGHT (FIG. 6B). SLC was barely detectable in the parental tumors (FIG. 6B). To exclude the possibility that the higher SLC detected in the Mutant LIGHT-expressing tumor was solely due to more vigorous ongoing immune responses with more T cells in the tumor environment, tumor tissues from RAG-1$^{-/-}$ tumor bearers. Ag104L d-Mutant LIGHT tumors growing in the lymphocyte deficient mice contained higher level of SLC than parental tumors (FIG. 6B). Furthermore, equal growth of both Mutant LIGHT-positive and negative tumors in RAG-1$^{-/-}$ mice suggested that chemokine SLC alone is not sufficient to mediate tumor rejection. These data were consistent with the immunohistochemical staining of tissue sections from other 5 pairs of Mutant LIGHT-positive and negative tumor samples collected from C3B6F1 tumor bearing animals (TBA). Very strong staining of SLC was detected near stroma-rich area in the LIGHT-expressing tumors surrounded by high density of infiltrating lymphocytes, as clearly shown by SLC and hemotoxylin double-stained tumor tissues (FIG. 6C). However, SLC was not detected in the stroma-rich area on the tumor tissues that are negative for Mutant LIGHT (FIG. 6C). The tissues from B7.1-expressing tumors also had no SLC staining and very few lymphocytes infiltration, similar to those of control tumors (FIG. 6C).

Adhesion molecules are critical for the migration of lymphocytes into the peripheral tissues and LTβR signaling is important for the expression of one of the adhesion molecules MAdCAM-1 (Kang, 2002). The expression level of MAdCAM-1 in the Mutant LIGHT-expressing tumor mass or the parental tumor was checked by real-time RT-PCR. Increased expression for adhesion molecule MAdCAM-1 in the Mutant LIGHT-expressing tumor mass compared to parental ones (FIG. 6D). These experiments strongly suggested that LIGHT in the tumor environment interacts with LTβR derived from tumor stroma to up-regulate chemokine SLC and adhesion molecule MAdCAM-1 to attract lymphocytes into the tumor environment.

In addition to lymphoid tissue chemokines, LTβR signaling also regulates a set of INF-γ-induced chemokines IP-10 and Mig. A gene array to compare the expression level of other chemokines revealed that IP-10 and Mig, which can potentially attract activated T cells, also were specifically up-regulated in the Mutant LIGHT-mediated tumor environment compared with parental one while other chemokines tested were comparable between Mutant LIGHT-positive or negative tumors. Therefore, Mutant LIGHT plays an important role in the formation of lymphoid microenvironment for recruiting naïve and possibly activated, T cells.

Example 6

Naïve T Cells Can be Recruited into Mutant LIGHT-Mediated Tumor Environment where they Proliferate and Reject Tumors Mutant LIGHT-mediated tumor environment contains high level of chemokine SLC and adhesion molecule MAdCAM-1, which potentially allow entry of naïve T cells. Three questions addressed directly were: 1) whether such environment is able to recruit naïve T cells; 2) whether naïve T cells can be activated inside the tumor, in vivo, in the presence of Mutant LIGHT; and 3) whether tumor bearing the antigen can be rejected by these T cells. The antigen L$^d$ expressed by Ag104, is an allogeneic MHC class 1 molecule that presents peptides derived from the house-keeping gene α-ketoglutarate dehydrogenase, on the surface of the tumor cells. In C3B6F1 (H-2$^{kXb}$) or B6 (H-2$^k$) hosts, adoptively transferred 2C TCR transgenic T cells only recognize Ag104 tumor cells directly presenting L$^d$ because 2C T cell responses required L$^d$ in its naïve form, which is lost when the antigen is processed and cross-presented by antigen presenting cells (APCs) from the hosts. Subcutaneously growing tumors are very inefficient to prime T cells via direct pathway in the lymphoid tissues. Ag104L$^d$ inoculated subcutaneously 24 hours after 3-5×10$^5$ CFSE-labeled 2C T cells were adoptively transferred into the C3B6F1 hosts. Proliferation of 2C T cells was not detected or measured by fluorescent dye CFSE dilution in the tumor draining lymph nodes, other non-draining lymph nodes or spleen up to 7 days after Ag104L$^d$ tumor challenge. 2C T cells in the secondary lymphoid organs maintained their naïve phenotype as indicated by low CD25, CD69 or CD44 on their surface during the 7-day observation. These indicated that T cells specific for antigens expressed on the tumor cells could not be activated if the antigens could not be cross-presented efficiently for many reasons. Consequently, 10$^6$ Ag104L$^d$ tumor cells were not rejected by C3B6 µl mice even when as many as 5×10$^6$ tumor antigen specific 2C T cells were transferred into the hosts.

Figure 7A:
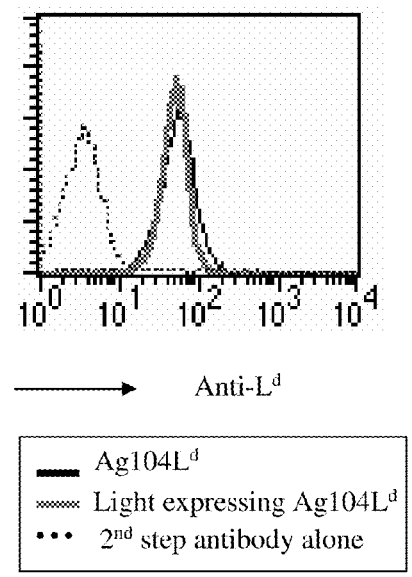
FIG. 7 shows that Mutant LIGHT-mediated Ag104Ld tumor environment recruits naïve 2C T cells, activates them and causes tumor rejection. A. Ag104Ld and Ag104Ld-mutant LIGHT expressed the same level of antigen Ld. Ag104Ld (black solid line) or Ag104Ld-mutant LIGHT (gray solid line) tumor cells were stained with anti-Ld followed by second step staining of FITC-conjugated goat antibody against murine IgG. Tumor cells stained with second-step antibody alone were shown in dotted lines. B. OT-1/RAG-1-/- mice were injected with 10$^6$ Ag104Ld or Ag104Ld-mutant LIGHT tumor cells subcutaneously. 3×10$^6$ CFSE-labeled 2C TCR transgenic T cells were transferred to these mice 10-14 days after tumor challenge. Tumor draining lymph nodes, non-draining lymph nodes, spleen and tumor tissue were collected 48, 132, 168 and 336 hours, as indicated, after 2C T cell transfer. T cells infiltrating tumors were isolated by a positive-selecting magnetic column. Cells from lymph nodes, spleen and tumor were subjected to FACS analysis after stained with anti-CD8 and 2C TCR clonotypic antibody 1B2. Proliferation of CD8 and 1B2 double positive 2C T cells was shown. OT-1/RAG-1-/- mice were injected with 10$^6$ Ag104Ld or Ag104Ld-mutant LIGHT tumor cells subcutaneously. 3×10$^6$ CFSE-labeled 2C TCR transgenic T cells were transferred to these mice 10-14 days after tumor challenge. Tumor draining lymph nodes, non-draining lymph nodes, spleen and tumor tissue were collected 48, and 336 hours, after 2C T cell transfer. T cells infiltrating tumors were isolated by a positive-selecting magnetic column. Cells from lymph nodes, spleen and tumor were subjected to FACS analysis after stained with antibody 1B2 and antibodies against activation markers CD62L or CD44. CD62L or CD44 expression by 1B2 positive 2C T cells was shown. C. OT-1/RAG-1-/- mice were injected with 10$^6$ Ag104Ld or Ag104Ld-LIGHT tumor cells subcutaneously. 3×10$^6$ 2C TCR transgenic T cells were transferred to these mice 10-14 days after tumor challenge. Adoptively transferred 2C T cells were able to suppress the growth of mutant LIGHT-expressing Ag104Ld in the OT-1/RAG-1-/- hosts but not the parental tumors.
Figure 7D:
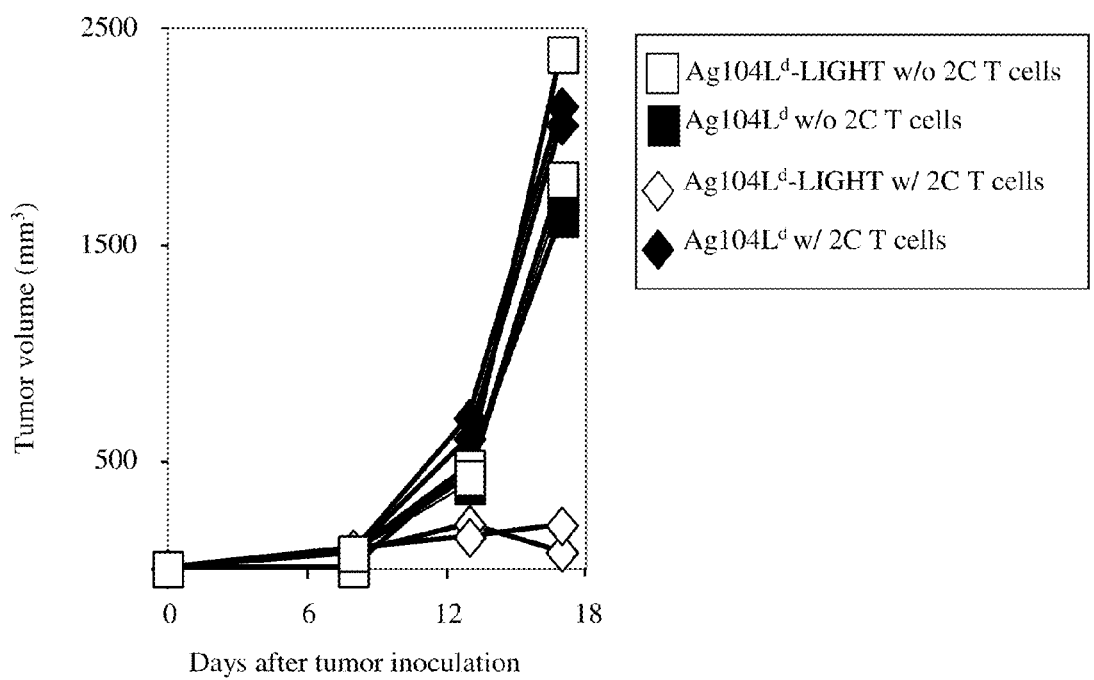
Figure 7B:
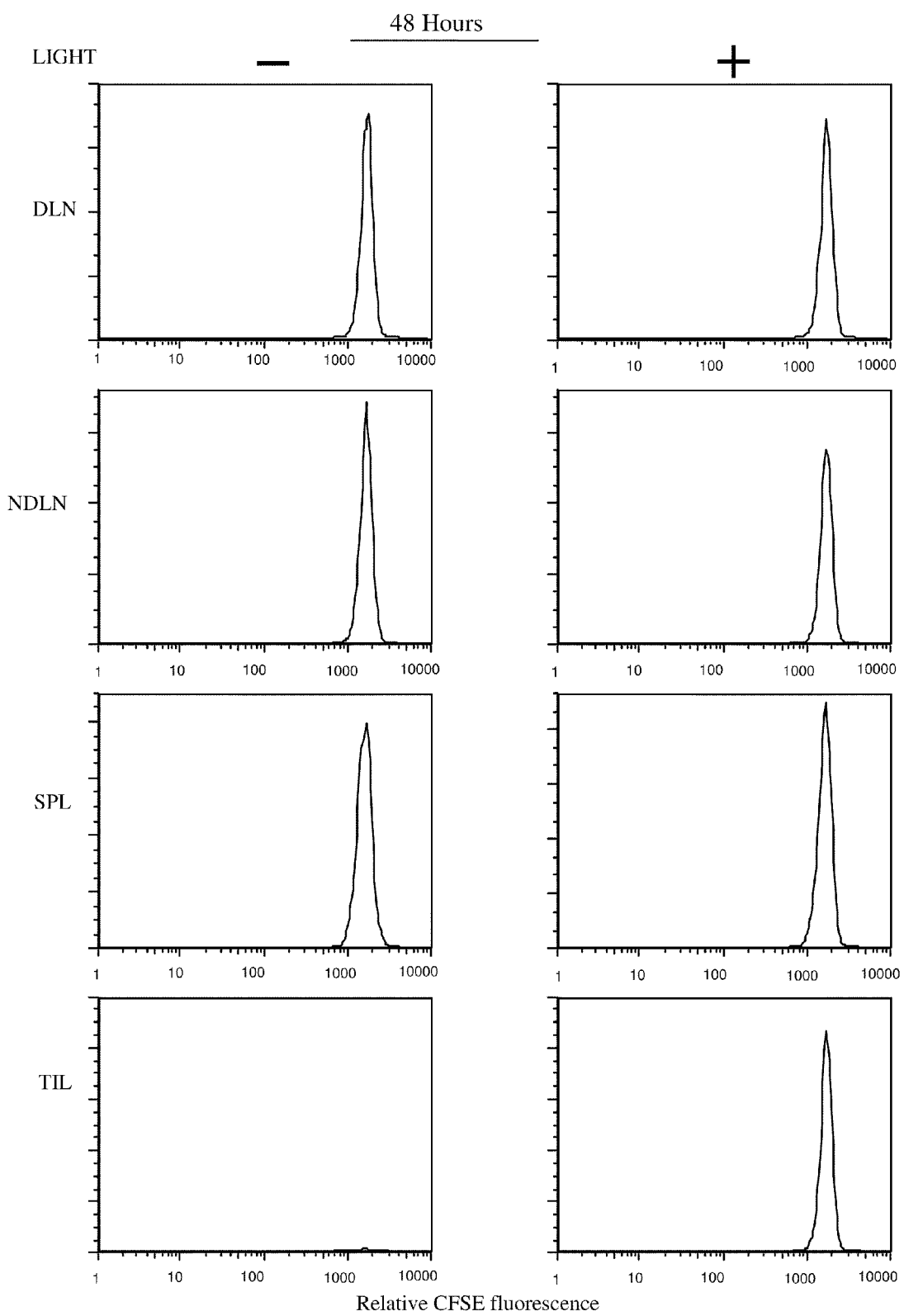
Figure 7B:
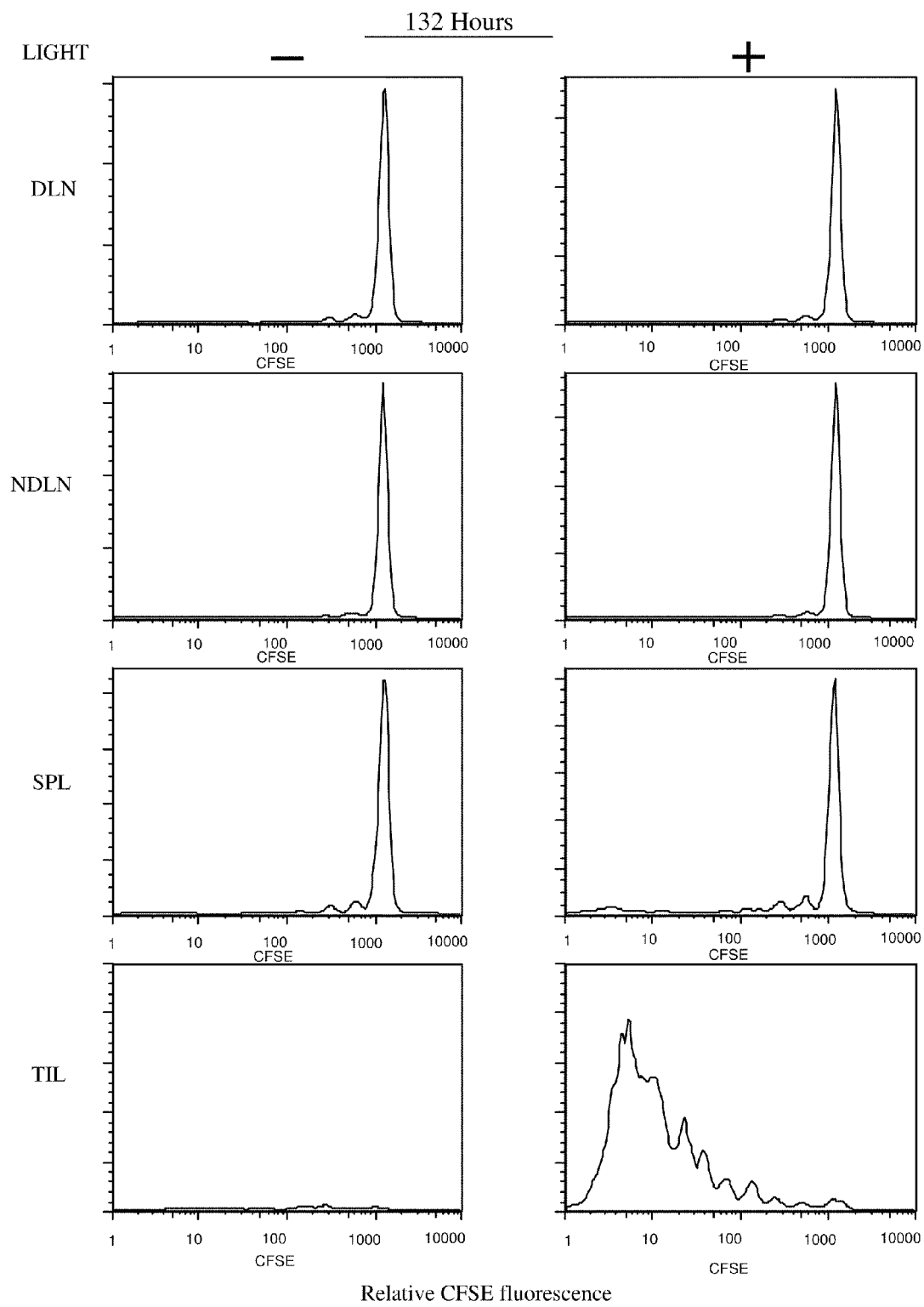
Figure 7B:
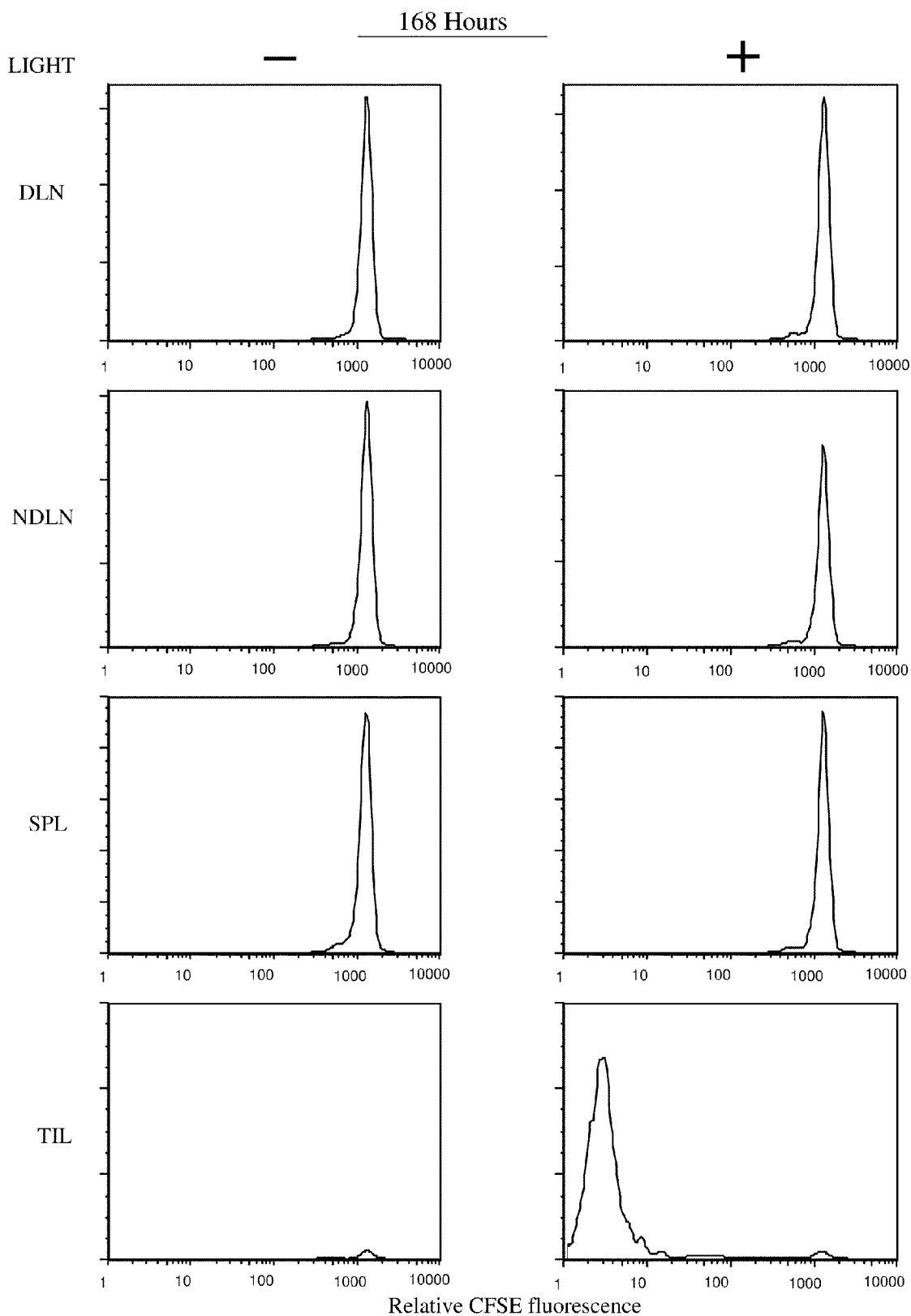
Figure 7B:
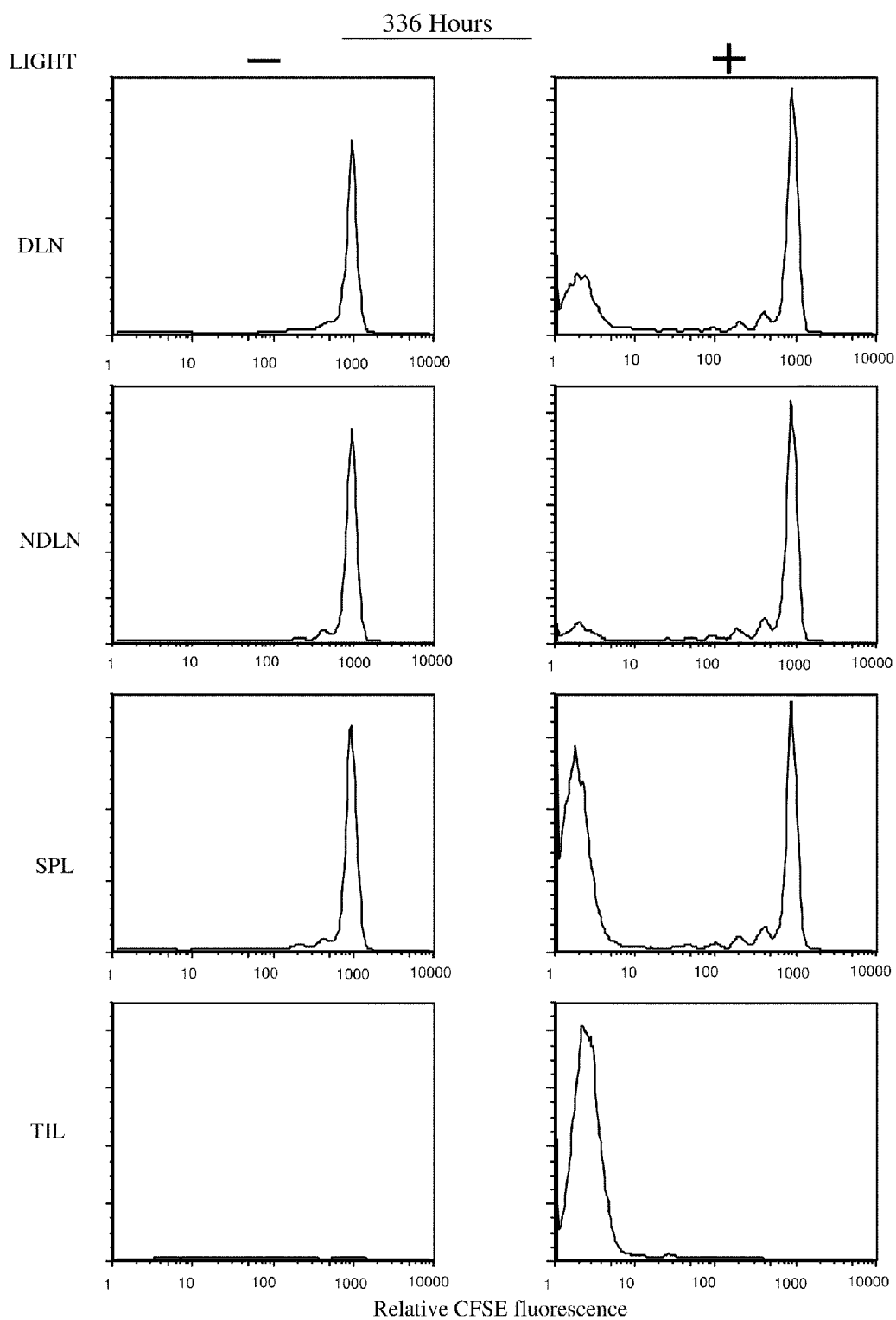
Figure 7C:
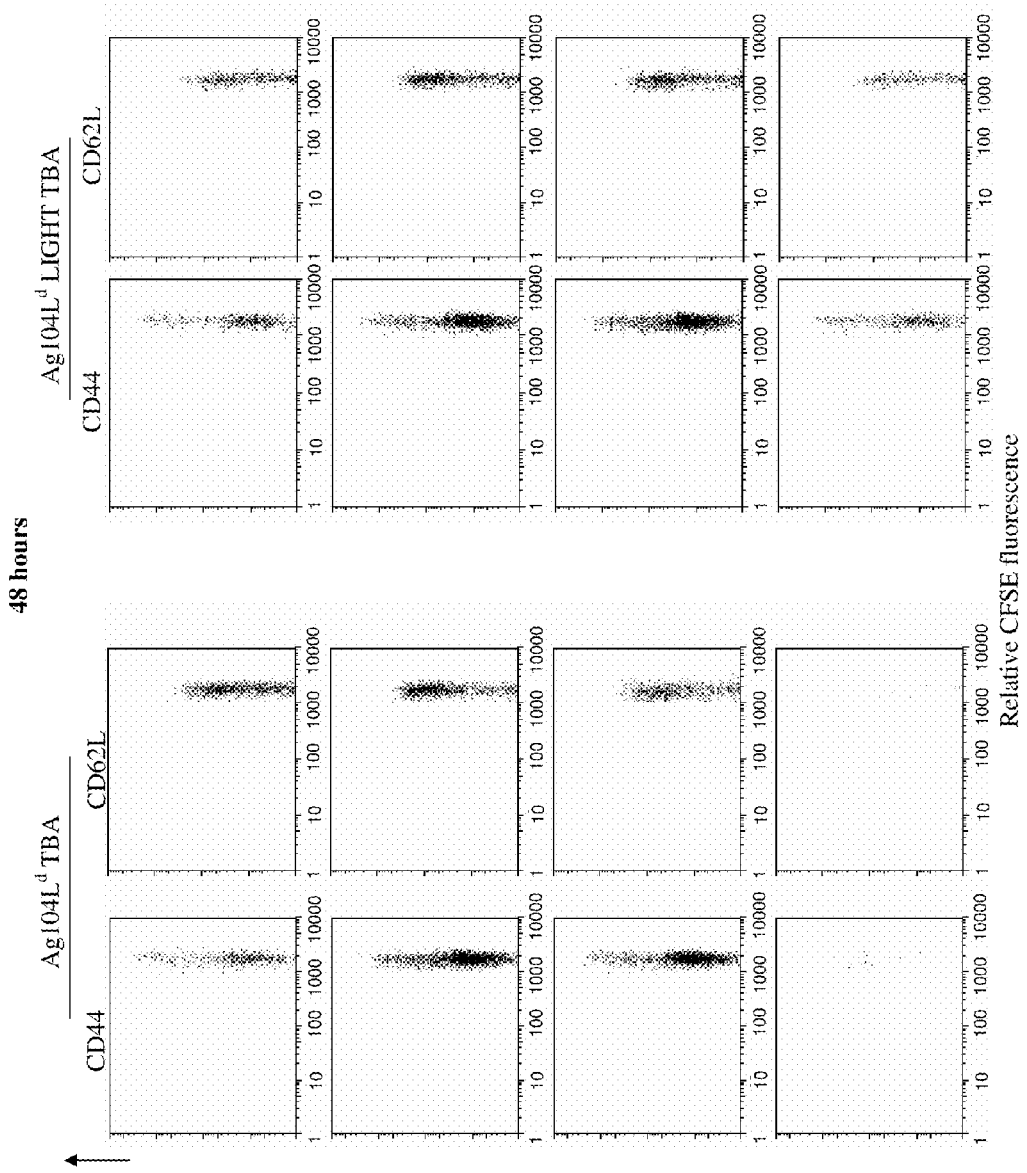
Figure 7C:
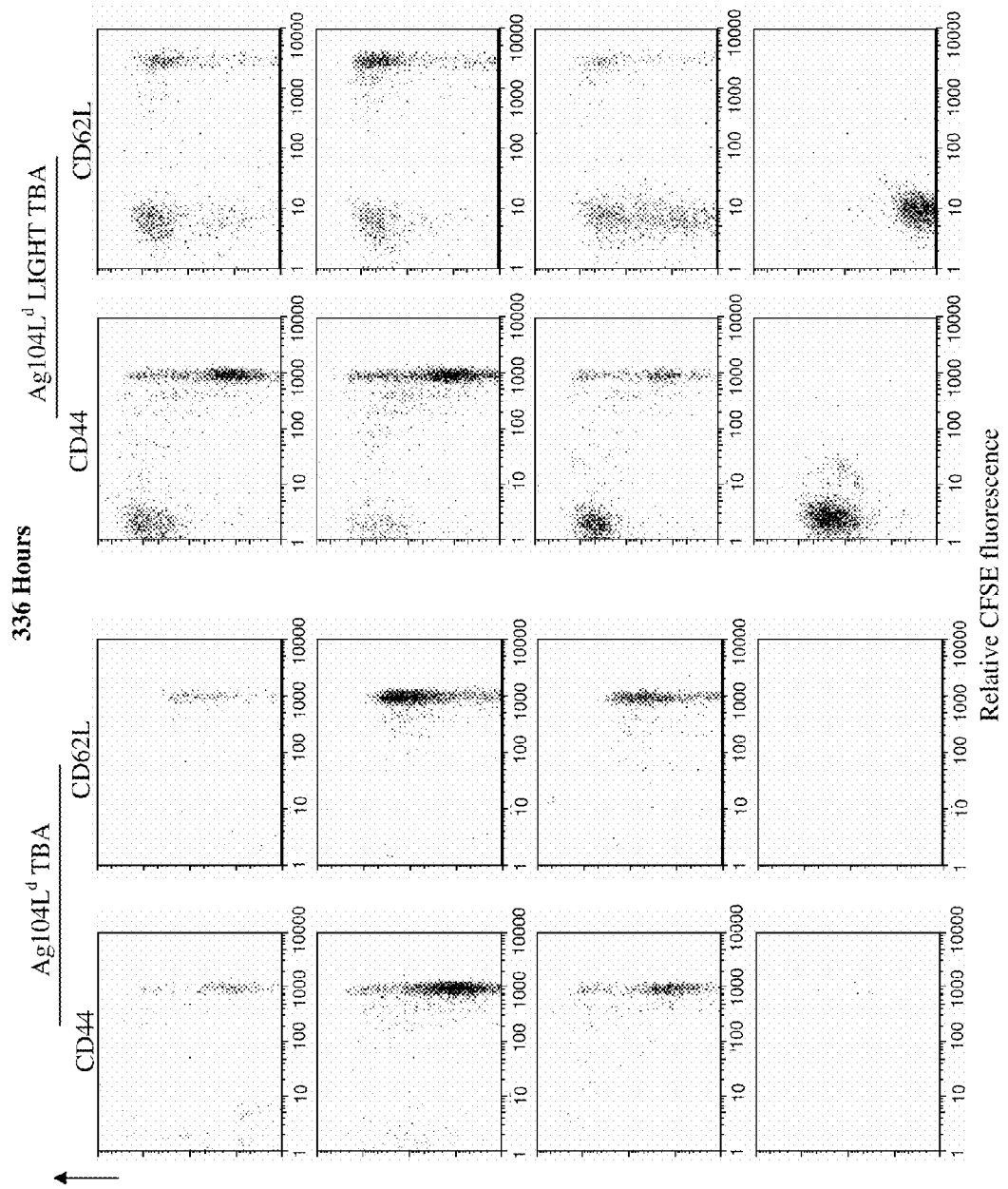

To investigate what happens when adoptively transferred 2C T cells when Mutant LIGHT is present inside the tumor environment. Mutant LIGHT-expressing Ag104L$^d$ tumors were rejected by endogenous CD8$^+$T cells without 2C T cell transfer in C3B6F1 hosts. In order to trace antigen-specific T cells and monitor their trafficking, priming and ability to reject tumors, H-Y or OT-1 TCR transgenic mice in B6 (H-2$^b$)/RAG-1$^{-/-}$background were used as recipients for tumor challenges. These mice harbor monoclonal CD8$^+$T cells that do not respond to Ag104L$^d$ tumor. Thus, Ag104L$^d$ or Mutant LIGHT expressing Ag104L$^d$ both grew aggressively in these mice similarly as in the RAG-1$^{-/-}$mice (FIG. 7C). However, adoptively transferred 2C T cells do not undergo vigorous homeostatic proliferation up to 14 days under constant observation due to the presence of these CD8$^+$H-Y or OT-1 transgenic T cells in these mice (FIG. 7B). Thus, the vigorous proliferation of 2C T cells in these hosts was antigen L$^d$ driven within 14 days after adoptive transfer. 10$^6$ Ag104L$^d$ or Ag104L$^d$-Mutant LIGHT, which expressed the same level of antigen L$^d$ on their surface (FIG. 7A), was subcutaneously inoculated into these mice. Then adoptively transferred 3×10$^6$ CFSE labeled 2C T cells to the mice 10-14 days after tumor challenge. Mice were sacrificed 48,132,168 and 336 hours after T cell transfer and tumor draining lymph nodes (DLN), other non-draining lymph nodes (NDLN), spleen (SPL) and tumor mass were collected. Single-cell suspension of tumor mass was obtained by collagenase digestion. If necessary, T cells infiltrating tumors (TIL) were purified with a positively selective magnetic system from tumor cells. 2C T cell trafficking and proliferation was evaluated. Naïve 2C T cells with high CFSE staining, high CD62L and low CD44 were present similarly in the secondary lymphoid organs in both Ag104L$^d$ or Ag104L$^d$-Mutant LIGHT bearing mice 48 hours after T cell transfer (FIG. 7B). However, a significant number of naïve 2C T cells, which are CD62L$^{high}$ and CD44$^{low}$, were detected inside Mutant LIGHT-expressing tumors but not in the parental tumors (FIG. 7B). This population of 2C T cells proliferated inside Mutant LIGHT-expressing tumor indicated by the dilution of CFSE 132 hours after T cell transfer (FIG. 7B). At this time point, no 2C T cells, naïve or proliferated, could be detected in the parental tumors (FIG. 7B). At 168 h after 2C T cell transfer, large amounts of proliferated 2C T cells were present solely in the Mutant LIGHT-expressing tumors. Up to 7 days (168 h) after 2C T cell transfer, no significant CFSE-labeled 2C T cell proliferation or proliferated 2C T cells could be detected in the secondary lymphoid tissues of the mice bearing Mutant LIGHT-positive or negative tumors (FIG. 5B). Activation of 2C T cells by antigen L$^d$ did not happen in the tumor draining nodes, other lymph nodes or spleen, but only inside Mutant LIGHT-positive tumor. 14 days after 2C T cell transfer, CFSE-low, fully proliferated 2C T cells were detected in the secondary lymphoid organs of the mice bearing Mutant LIGHT-expressing tumors. The 2C T cells present in the lymph nodes expressed high level of CD44 and CD62L. However, the 2C T cells trafficking to the spleen were mixtures of CD44$^{high}$CD62L$^{low}$ and CD44$^{high}$CD62L$^{high}$ populations (FIG. 5C). In the mice bearing parental tumors, 2C T cells present in the secondary lymphoid organs maintained a naïve phenotype (CD62L$^{high}$ and CD44$^{low}$) without significant proliferation after 14 days (FIG. 7B). Furthermore, no detectable 2C T cells, naïve or activated, present inside the parental tumors (FIG. 7B).

2C T cell proliferation correlated with tumor rejection. Ag104L d-Mutant LIGHT tumors established for 10 days in these H—Y transgenic mice were completely suppressed while the parental tumors grew comparably to those in mice without 2C T cell transfer (FIG. 7D).

C3B6F1 mice were used as tumor recipients. 5×10$^6$ Ag104L$^d$ or Ag104L$^d$-LIGHT was inoculated subcutaneously to C3B6F1 mice. 10-14 days later, 3×10$^6$ CFSE labeled 2C T cells were adoptively transferred into the hosts and trafficking and proliferation of the T cells in the tumor draining lymph nodes, other non-draining lymph nodes, spleen or tumor mass were checked after 48 hours and 168 hours. It yielded similar results as in H-Y or OT-1 TCR transgenic mice.

Naïve tumor antigen-specific T cells can be recruited to the tumor site and they proliferated there effectively and killed the tumor cells in the mutant LIGHT-mediated environment even when the antigens are not well cross-presented. More significantly, these T cells were able to suppress tumor grow in situ. Interestingly, mutant LIGHT-mediated tumor environment generated large amount of tumor antigen-specific T cells that were able to leave tumor site, re-circulate and potentially reject other tumors in the distal sites bearing the same antigen without mutant LIGHT (TABLE 3).

Example 7

Therapeutic Vaccination with Mutant LIGHT-Expressing Ag104L$^d$ Eradicates Established Parental Tumor Mutant LIGHT-mediated tumor environment was able to recruit naïve T cells and activate them inside the tumor and cause tumor rejection. The potential therapeutic efficacy of the finding was shown by injecting mutant LIGHT-expressing tumor cells into the established parental tumor. Such treatment could create a lymphoid environment to attract naïve T cells and then activate tumor specific ones via co-stimulation in the presence of antigen leading to the rejection of these established tumors. 10$^5$ Ag104L$^d$ was inoculated subcutaneously to C3B6F1 recipients and the tumors were allowed to establish for 14 days. Then 10$^6$ mutant LIGHT-expressing Ag104L$^d$ tumor cells were injected inside the established parental tumors. As control, the same volume of PBS was injected into the tumors in the same way. The established parental tumors treated with mutant LIGHT-expressing tumor cells continued to grow for 10-15 days before they started to regress and disappeared (FIG. 8). Ag104L$^d$ tumors treated with PBS grew aggressively.

Mutant LIGHT-mediated tumor environment generated many tumor antigen-specific central and effector memory T cells going back to circulation. The generation of such a pool of lymphocytes may be important to eradicate metastasis after surgical removal of primary tumors. Tumor antigen-specific memory T cells with high quantity from mutant LIGHT-mediated environment may be able to reject established parental tumor in the distal site. To set up a clinically relevant model, 10$^4$ Ag104L$^d$ tumor cells was injected to the left flank of C3B6 μl hosts and the tumors were established for 20 days. 10$^6$ Ag104L$^d$-mutant LIGHT tumor cells were injected 20 days later to the right flank of the mice. Alternatively, the same volume of PBS was injected to the Ag104L$^d$-tumor bearing mice in the control group. 100% of the mice treated with Mutant LIGHT-bearing tumor cells rejected the established parental tumors. Ag104L$^d$ tumors grew progressively on the mice in the control group 100% (Table 2).

The therapeutic efficacy of mutant LIGHT-expressing tumor cells was demonstrated in another model more closely simulated clinical metastasized tumors. 10$^6$ (primary tumor) and 5×10$^4$ (distal tumor) Ag104L$^d$ tumor cells were inoculated into the left and right flank of the recipient mice, respectively. The primary tumor was surgically removed 14 days after tumor inoculation and 10$^6$ Mutant LIGHT-expressing Ag 104L$^d$ tumor cells were injected into the upper back of the mouse. Growth of the established distal tumors was observed. All the mice in the treated group rejected the distal tumors. However, without treatment with mutant LIGHT-expressing tumor, the distal tumor killed all the hosts in the control group (TABLE 2).

Mutant LIGHT-mediated tumor environment is able to recruit naïve T cells and activated and expanded tumor antigen-specific T cells and reject tumor cells bearing the antigen in situ. Moreover, large amount of tumor antigen-specific central and effector memory-type T cells were generated inside the environment and able to traffick to distal sites to reject tumors bearing the same antigen (Table 3).

Figure 10:
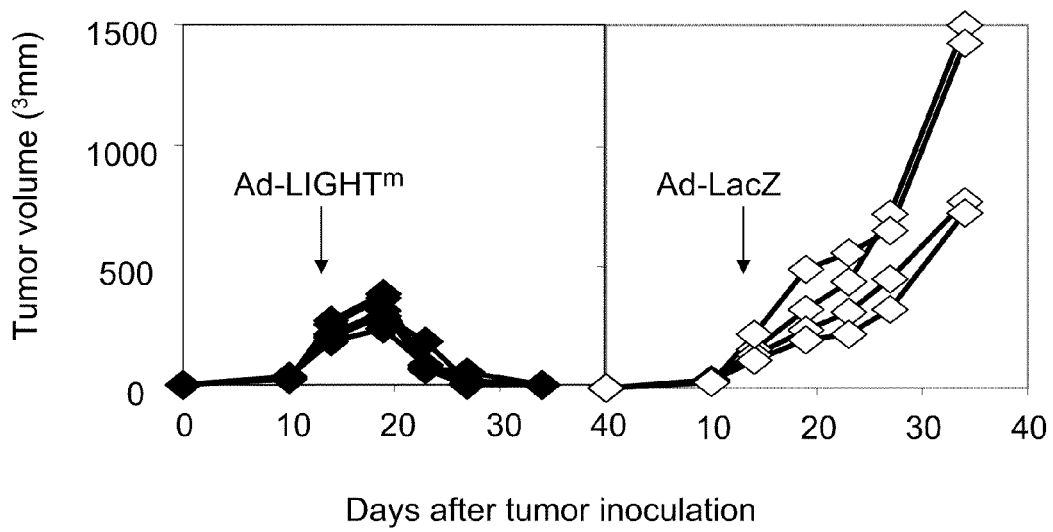
FIG. 10 shows that delivery of mutant LIGHT by adenovirus into tumor tissues allows effective immune response and tumor rejection. C3B6F1 mice were inoculated with 2×10$^5$ d tumor cells, followed by an intratumoral injection of 5×10$^{10}$ mutant LIGHT-expressing adenovirus (left) or LacZ-expressing adenovirus as indicated (right) 14 d after parental tumor challenge. Tumor volume was calculated by formula (length× width×height)/2.
Figure 11:
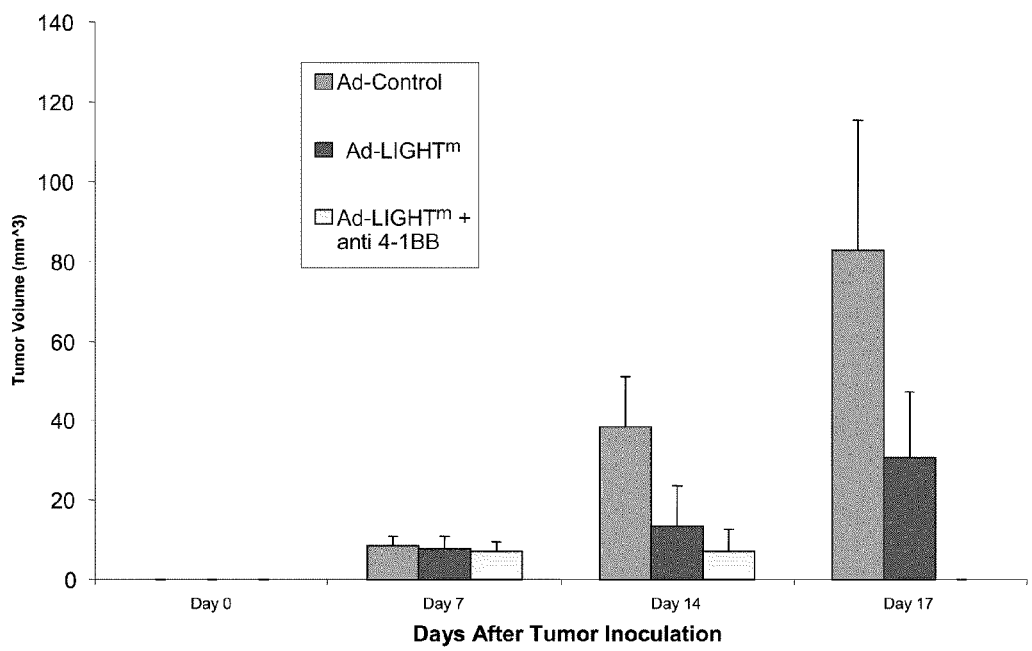
FIG. 11 shows inhibition of 4T1 tumor growth and reduction in spontaneous metastatic tumors. At Day 0 4T1 mice were inoculated with control, mutant LIGHT or Mutant LIGHT and anti 4-1 BB. At Day 7 Ad-mutant LIGHT (or D10 2A) showed some reduction, at Days 14 and 17 this volume reduction was more pronounced. At Day 19 tumors are removed. At Day 34 tissues were checked for lung metastasis.
Figure 12:
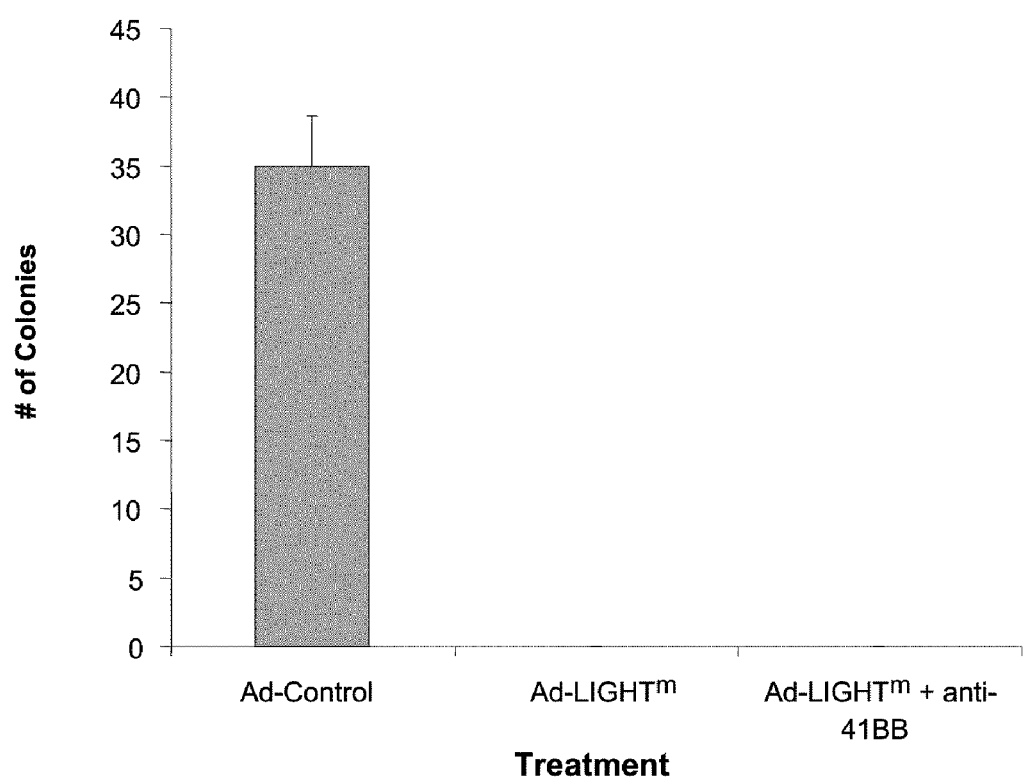
FIG. 12 shows results of a clonogenic assay of the treatment groups' of FIG. 11. Metastases in mice treated with Ad-mutant LIGHT with and without 41 BB were prevented.

Delivery of mutant LIGHT by adenovirus into tumor tissues allows effective immune response and tumor rejection. FIG. 10 illustrates the reductions of tumor volume correlated with the presence in vivo of mutant LIGHT expression in tumor cells. FIG. 11 illustrates reduction in spontaneous metastasis in mice at days 14, 17 and until day 34 after inoculation. There is a synergistic effect of anti-41 BB, an antibody that stimulate T cells, on tumor reductions. FIG. 12 illustrates that the clonogenic assay shows no evidence of metastasis after mutant LIGHT treatment.

Example 8

LIGHT Delivered by Adenovirus Mediates Host Resistance to Tumor

Figure 13A:
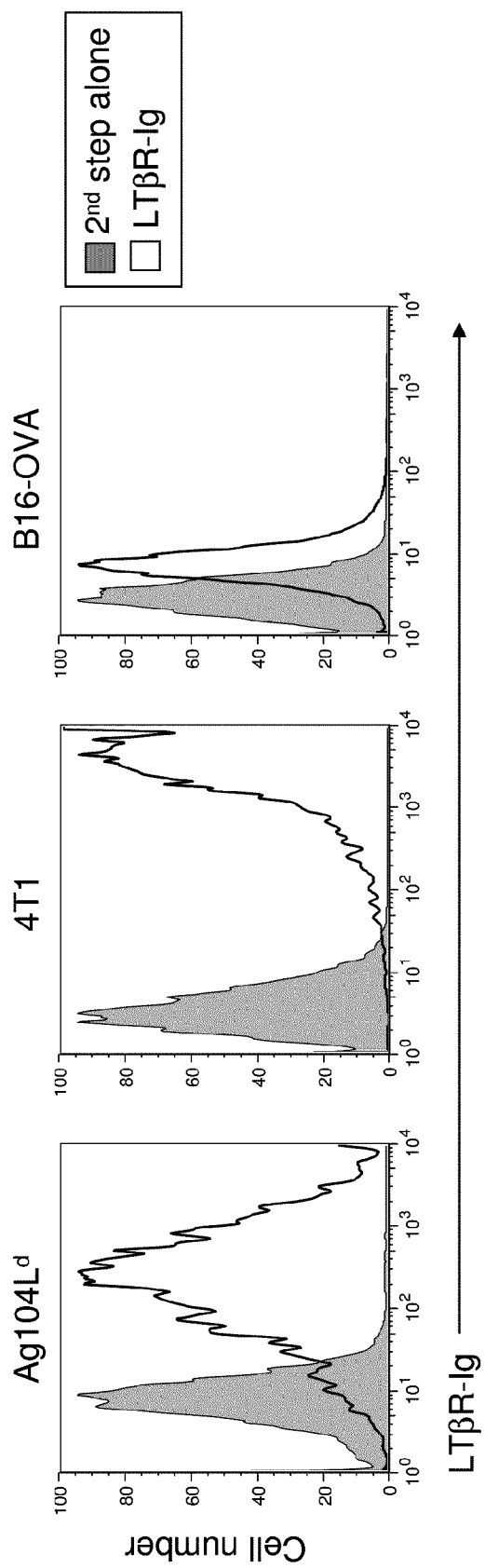
FIG. 13 shows that intratumoral Ad-mutant LIGHT treatment inhibits the growth of the primary tumors. A. 1×10$^6$ tumor cells were plated in 100 mm cell culture dish for 24 hours then infected with Ad-mutant LIGHT at 4×10$^8$ pfu/ml for 24 hours. Cells were harvested and checked for mutant LIGHT expression by FACS staining with LTβR-Ig at 0.02 mg/mL followed by 2$^{nd}$ step antibody PE-coupled donkey anti-human IgG (white), or with 2$^{nd}$ step antibody alone as control (grey). B. Antitumor effects of Ad-mutant LIGHT on Ag104L$^d$ tumors. 10$^6$ Ag104L$^d$ tumor cells were injected subcutaneously to the C3B6F1 mice. 5×10$^9$ pfu Ad-mutant LIGHT (black diamond) or control virus expressing LacZ (Ad-control) (white diamond) were injected intra-tumorally 14 days after tumor challenge. Tumor growth was recorded. Tumor volume was calculated as length×width×height/2. One representative of three experiments was shown. Arrow indicates the time of injection C. Antitumor effects of Ad-mutant LIGHT on B16-SIY tumors. B6 WT mice were injected subcutaneously with 1×10$^6$ cells near the base of the tail. 10 days later, 2×10$^9$ PFU of either Ad-mutant LIGHT (black diamond) or Ad-Control (white diamond) was injected intratumorally. The treatment was repeated 4 days later followed by continued monitoring for tumor growth. One representative of two experiments was shown. Arrows indicate the time of injection. D. Antitumor effects of Ad-mutant LIGHT on MC38 tumors. B6 WT mice were injected subcutaneously with 1×10$^5$ cells near the base of the tail. 10 days later, 2×10$^9$ PFU of either Ad-mutant LIGHT (black diamond) or Ad-Control (white diamond) was injected intratumorally. The treatment was repeated twice with 3 days apart followed by continued monitoring for tumor growth. Arrows indicate the time of injection.
Figure 13B:
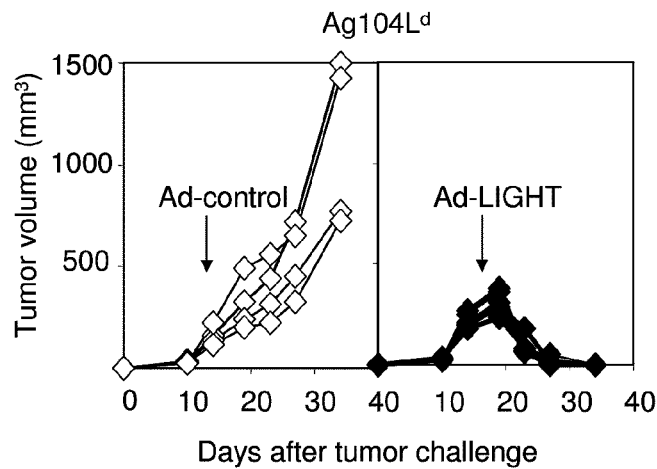
Figure 13C:
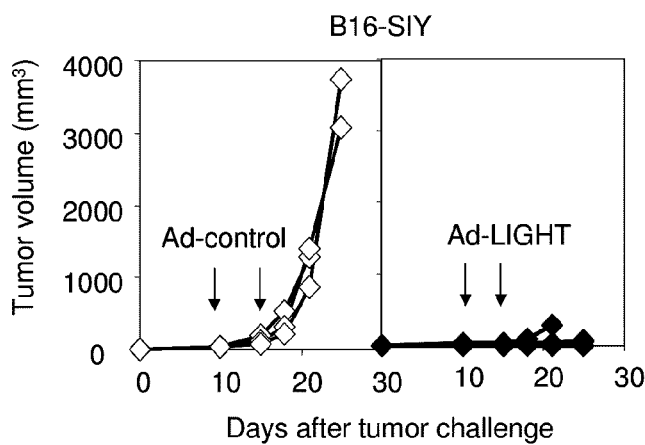
Figure 13D:
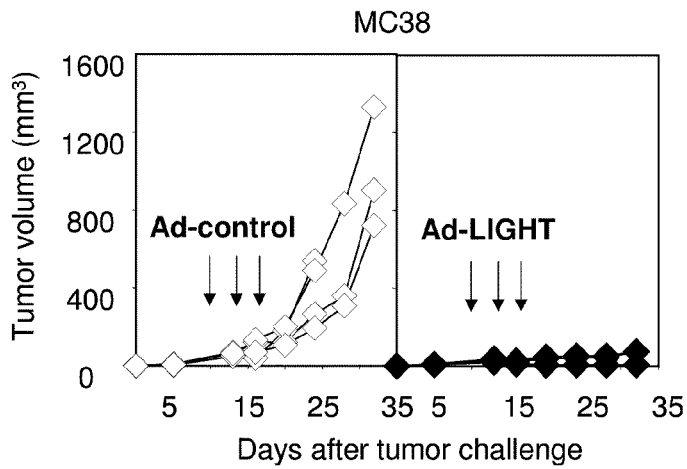

To develop a clinically relevant therapeutic strategy to deliver mutant LIGHT into tumor tissue, a recombinant replication-deficient adenovirus expressing mutant LIGHT (Ad-mutant LIGHT) was generated. To determine whether Ad-mutant LIGHT transferred expression of LIGHT in tumor cells, three tumor cell lines (fibrosarcoma Ag104L$^d$, melanoma B16-OVA, and mammary carcinoma 4T1) were infected in vitro for 24 hours. Detection of LIGHT expression was evaluated using a soluble lymphotoxin β receptor (LTβR), one of the receptors for LIGHT. Ad-mutant LIGHT was able to confer LIGHT expression on all three tumor cell lines (FIG. 13A). It was tested whether mutant LIGHT delivered by adenovirus could mediate the rejection of an established tumor. Ag104L$^d$ tumor cells were injected subcutaneously to the C3B6F1 mice. Ad-mutant LIGHT ($5 \times 10^9$ p.f.u.) or control virus expressing LacZ (Ad-control) were injected intratumorally 14 days after tumor challenge when the mass was well-established. The Ag104L$^d$ tumors persisted for a few days before being completely rejected after Ad-mutant LIGHT treatment while those treated with Ad-control continued grew progressively (FIG. 13B). Tumor rejection mediated by Ad-mutant LIGHT was CD8$^+$ T cell-dependent and led to strong memory protection against the re-challenge of Ag104L$^d$ at dose as high as $10^7$ tumor cells. Ag104L$^d$ tumor was able to completely regress by the Ad-mutant LIGHT treatment. In addition, some tumors, such as a colon cancer MC38, melanoma B16-SIY and mammary cancer 4T1, which are thought to be more aggressive and/or display lower immunogenicity, were significantly inhibited in their growth (FIGS. 13C-D and FIG. 14A). These results demonstrate that Ad-mutant LIGHT injected intratumorally can mediate partial or complete control of large established tumors.

Example 9

Ad-Mutant LIGHT Controls Spontaneous Tumor Metastases

It was determined whether Ad-mutant LIGHT treatment of the primary tumor could induce a sufficient immune response to control disseminated metastases. 4T1 breast carcinoma closely mimics human breast cancer in its anatomical site, immunogenicity, growth characteristics, and metastatic properties. It is poorly immunogenic as the surgical removal of a growing 4T1 tumor will not confer protection against re-challenge. When $10^5$ 4T1 tumor cells was injected subcutaneously into wild-type (WT) Balb/c mice, either at the mammary fat pad, or around the tail base, metastases was consistently detected in various organs and draining lymph nodes (LN) 11 days after tumor inoculation.

To determine whether the anti-tumor response generated at the primary tumor site by Ad-mutant LIGHT might be sufficient to eliminate or control micro-disseminated tumor cells, the 4T1 tumor cells were first infected in vitro with Ad-mutant LIGHT or Ad-control. The 4T1 tumor cells infected with Ad-mutant LIGHT expressed high level of LIGHT 24 hours after infection while the ones infected with Ad-control did not express LIGHT at a detectable level (FIG. 13A). The tumor cells were then harvested from the culture 24 hours after Ad-mutant LIGHT infection and 105 of mutant LIGHT-expressing or Ad-control-infected 4T1 tumor cells were inoculated subcutaneously into Balb/c mice. Primary tumor growing subcutaneously was monitored for 35 days before the mice were sacrificed for the evaluation of metastasis in the lung using a colony assay. The growth of the primary tumor was hindered yet continued to progress without being completely rejected (FIG. 14B). However, no colonies of metastatic cells were detected in the lungs of mice inoculated with LIGHT-expressing 4T1 tumor cells while a high number of metastases was detected in the lungs of mice bearing control tumors (FIG. 14C). Depletion of CD8$^+$ T cells abrogated this effect. The control of metastasis may be attributed to the mutant LIGHT expressed locally in the primary tumor since the distal metastatic tumor cells were not possible to be infected to express mutant LIGHT in this model. These results indicated that mutant LIGHT expression by the 4T1 tumor during the initial stage of tumor growth was sufficient to control metastases in the presence of a growing primary tumor.

The therapeutic effects of Ad-mutant LIGHT were tested. Whether Ad-mutant LIGHT delivered directly into an established tumor would control cancer metastasis was tested. The subcutaneous growth of $10^5$ 4T1 tumor cells in Balb/c mice was established for 7 days, followed by the intra-tumor injection of $5 \times 10^9$ p.f.u. of Ad-mutant LIGHT or Ad-control. The growth of the primary tumor was suppressed after Ad-mutant LIGHT treatment but continued to grow. In order to mimic the clinical therapeutic setting, the primary tumor was surgically removed 18 days after the tumor inoculation. Mice were then sacrificed to evaluate the metastasis in the lung using the colonogenic assay 35 days post-primary tumor injection. Interestingly, no metastasis was detected in the lung of the mice that had been given Ad-mutant LIGHT treatment while large numbers of metastatic cancer cells were found in the lung of the control mice (FIG. 14D). These results demonstrated that mutant LIGHT delivered by adenoviral gene transfer into an established primary tumor induced significant tumor-specific CTL to control the occurrence of spontaneous metastasis.

Example 10

Ad-Mutant LIGHT Mediates the Rejection of Established Spontaneous Lung Metastasis Without being bound by a particular mode or theory, there are two possible general mechanisms by which Ad-mutant LIGHT treatment could inhibit the number of metastatic cancer cells present in the lung. One is that Ad-mutant LIGHT-induced anti-tumor immunity suppresses the growth of the primary tumor which then prevents the exit of tumor cells to other sites. The other is that Ad-mutant LIGHT triggers a potent anti-tumor immunity to cause rejection of already seeded distal metastatic tumors. Given the potent anti-metastatic activity of Ad-mutant LIGHT treatment, it was examined whether Ad-mutant LIGHT treatment would possibly be effective to treat the hosts already bearing detectable metastasis. Since subcutaneous injection of $10^5$ 4T1 tumor cells consistently resulted in detectable metastasis in the lung 11 days post-tumor inoculation, Ad-mutant LIGHT treatment after the 11 day-time point would indicate the effectiveness of the treatment on already seeded metastatic cancer cells. About $10^5$ 4T1 tumor cells were inoculated subcutaneously to Balb/c mice, provided intra-tumoral injection of $2 \times 10^9$ p.f.u.

of Ad-mutant LIGHT or Ad-control 14 and 17 days later, then surgically removed the primary tumor 29 days after initial tumor inoculation. The mice were sacrificed and the metastasis in the lung was analyzed 35 days post inoculation of primary tumor. While a large number of metastatic colonies were found in the lung of the Ad-control-treated mice, a dramatic decrease in the number of metastatic cancer cells was detected in Ad-mutant LIGHT-treated mice (FIG. 15A). Local treatment of cancer with Ad-mutant LIGHT is effective at eradicating preexisting metastases.

In an aspect, for clinical application, surgical removal of the tumor may be necessary immediately, precluding the possibility of intratumoral injection prior to resection. In addition, effective intratumoral delivery of Ad-mutant LIGHT in tumors that are not readily accessible can be performed by introducing mutant LIGHT expressing tumor cells. An alternative strategy to deliver Ad-mutant LIGHT by vaccinating with transduced tumor cells following surgical excision was analyzed. 4T1 tumor cells were inoculated subcutaneously in Balb/c mice, followed by surgical removal 18 days later, which is one week after the initiation of metastasis. Evidence of metastatic spread at this time point was verified by the colonogenic assay. 4T1 cells grown in culture were then infected with either Ad-mutant LIGHT or Ad-control for 24 hours, irradiated, and injected subcutaneously into the mammary fat pad the following day. The treatment was given on days 18 and 25. Mice were sacrificed and the metastasis in the lung was examined 35 days post inoculation of primary tumor. As expected, a large number of metastasis were present in the lung of the control mice. Surprisingly, no metastatic cancer cells were detected in mice treated with irradiated Ad-mutant LIGHT-transduced tumor cells (FIG. 15B). These results suggest that Ad-mutant LIGHT-transduced tumor cells are part of a potent therapeutic vaccine that is capable of mediating the rejection of seeded metastatic tumors.

Example 11

Activated Tumor Antigen-Specific T Cells Leave the Mutant LIGHT-Mediated Tumor Environment and Subsequently Appear in the Lymphoid Tissues Delivery of mutant LIGHT by adenovirus intratumorally induced strong anti-tumor immunity and caused rejection of spontaneous metastasis. Ad-mutant LIGHT stimulates tumor-specific CD8$^+$ T cells from within the tumor and generate effector/memory T cells that subsequently circulate systemically and reject the disseminated tumor cells. However, it is difficult to confirm that the activated tumor-specific T cells detected in draining LN come from tumor or are generated in draining LN because cross-presentation of tumor antigens can occur in both compartments. To clearly distinguish whether the tumor antigen-specific T cells are activated first in the tumor or in lymphoid tissues, a system in which reactive T cells recognize antigen only through direct presentation on tumor cells was used. In B6/OT-1/Rag-1$^{-/-}$ hosts (H-2$^b$) (OT-1 mice), adoptively transferred 2C TCR transgenic T cells recognizing Ag 104L$^d$ tumors, a fibrosarcoma transfected to express H-2L$^d$, cannot be activated by indirect presentation, but can only be activated by direct presentation of the aberrant MHC class I molecule. These host mice lack endogenous T cells reactive to the Ag 104L$^d$ tumor, and 2C T cells are the only T cells mediating the anti-tumor responses. In addition, 2C T cells cannot undergo homeostatic expansion on transfer into these mice in the presence of CD8$^+$ OT-1 T cells. Thus, the priming by the Ag104L$^d$ tumors is dependent on the direct presentation to 2C T cells in the tumor in this model. In addition, to focus on studying the local effects of mutant LIGHT and avoid the potential for systemic spreading of Ad-mutant LIGHT that could reach lymphoid organs, Ag104L$^d$ or mutant LIGHT-expressing Ag104L$^d$ tumor lines were used.

Figure 16A:
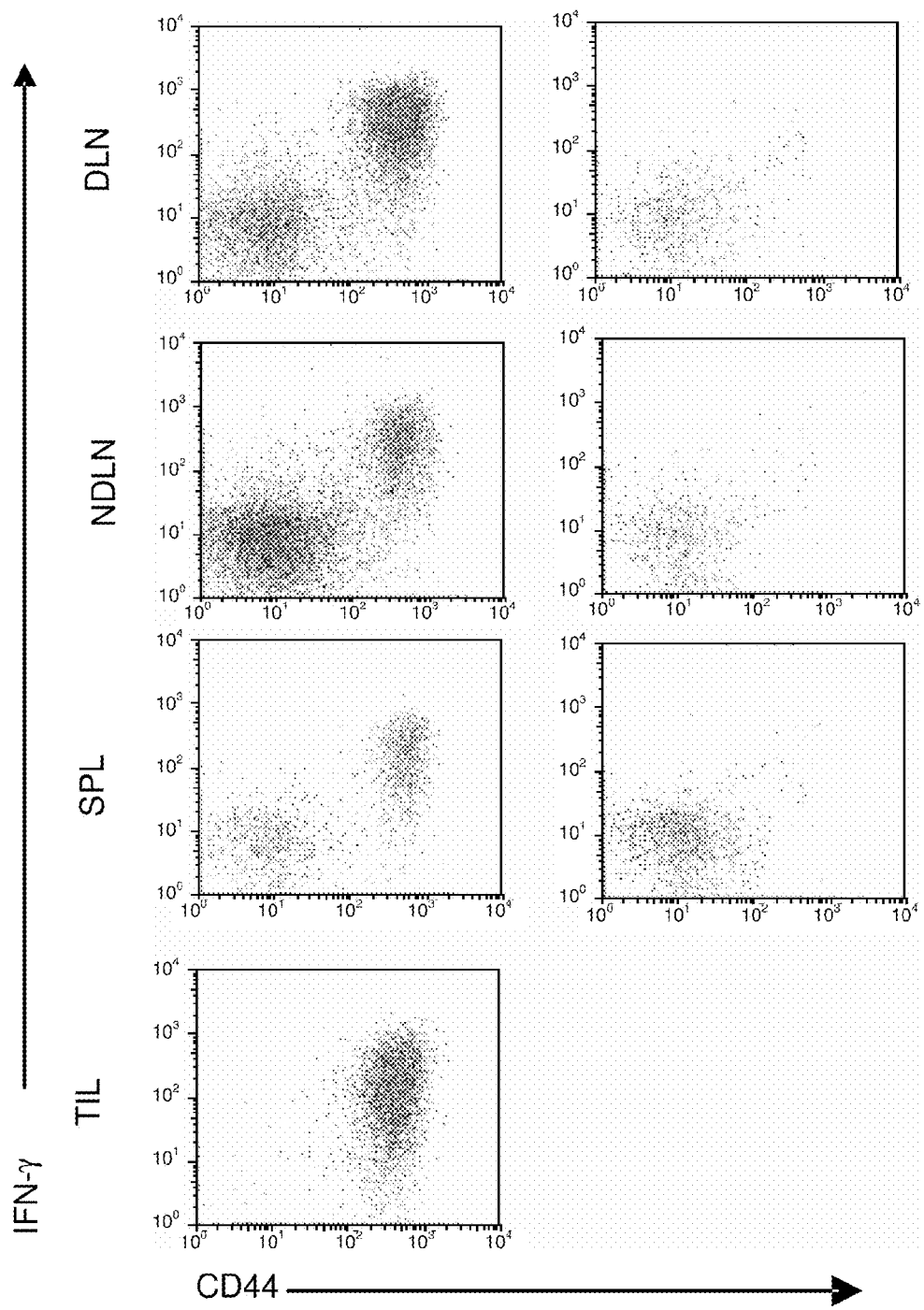
FIG. 16 demonstrates that antigen-specific T cells stimulated by mutant LIGHT inside the tumor traffic to the distal sites. A. $10^6$ Ag 104L$^d$ or Ag 104L$^d$-mutant LIGHT cells expressing the same amount of L antigen were inoculated subcutaneously to OT-1 mice. After 10-14 days, $3\times10^6$ CFSE-labeled 2C T cells were infused to these OT-1 mice. The expression of CD44 and secretion of IFN-γ by 2C T cells were evaluated 14-20 days after adoptive transfer in the draining lymph nodes (DLNs), non-DLNs and spleen, and in the tumor itself. B-C. Each of the OT-1 mice was inoculated with two tumors. The primary tumor was either $10^6$ Ag104L$^d$ or Ag104L$^d$-mutant LIGHT, while the secondary one was $10^5$ Ag104L$^d$ tumor cells. 10-14 days post tumor challenge $3\times10^6$ CFSE-labeled 2C T cells were infused into mice. Presence and CFSE dilution of the 2C T cells were evaluated at days 3, 5 and 10 after adoptive transfer inside the primary and the secondary tumors (B). The percentage of 2C T cells in the secondary tumors in the hosts bearing a mutant LIGHT-expressing Ag104L$^d$ or parental Ag104L$^d$ was compared (C). D. T cells from the lymphoid organs of Ad-mutant LIGHT-treated mice mediate the rejection of established tumors upon adoptive transfer. $10^5$ Ag104L$^d$ tumor cells were inoculated to the C3B6F1 mice. The mice were then treated with $5\times10^{10}$ virus particles of Ad-mutant LIGHT or Ad-control 14 days post tumor challenge. 7 days after the treatment, we collected the spleen and lymph nodes from the treated mice and purified the T cells and adoptively transferred $10^7$ of these T cells to C3B6F1 mice bearing an Ag104L$^d$ tumor that has been established for 7 days. The tumor growth on these mice was monitored.

The subcutaneous inoculation of 10$^6$ Ag104L$^d$ or Ag104L$^d$-mutant LIGHT cells in OT-1 mice was followed after 10-14 days by the infusion of 3×10$^6$ CFSE-labeled 2C T cells. The presence of activated 2C T cells was evaluated 14-20 days after adoptive transfer in the draining lymph nodes (DLNs), non-DLNs and spleen, and in the tumor itself. A large number of activated 2C T cells were observed displaying high surface expression of CD44 and production of IFN-γ were present inside the mutant LIGHT-expressing Ag104L$^d$ tumors (FIG. 16A). In contrast, activated 2C T cells were barely detectable in the parental Ag 104L$^d$ tumors. At this time point, a higher percentage of activated 2C T cells in the lymphoid tissues including DLN, non-DLN and spleen was found (FIG. 16A). These activated 2C T cells all expressed high level of CD44 and IFN-γ (FIG. 16A). Some activated antigen-specific T cells are capable of migrating out of the tumor and into systemic circulation following local expression of mutant LIGHT inside the tumor.

Example 12

Figure 16B:
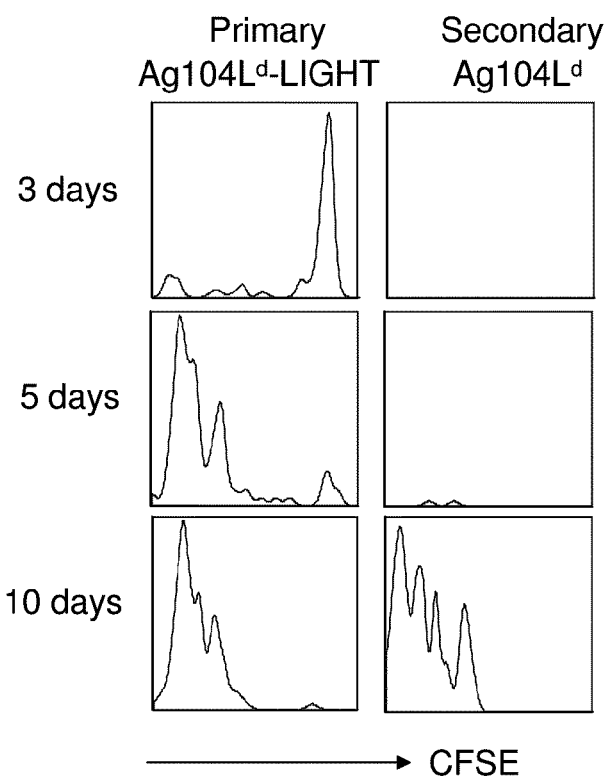
Figure 16C:
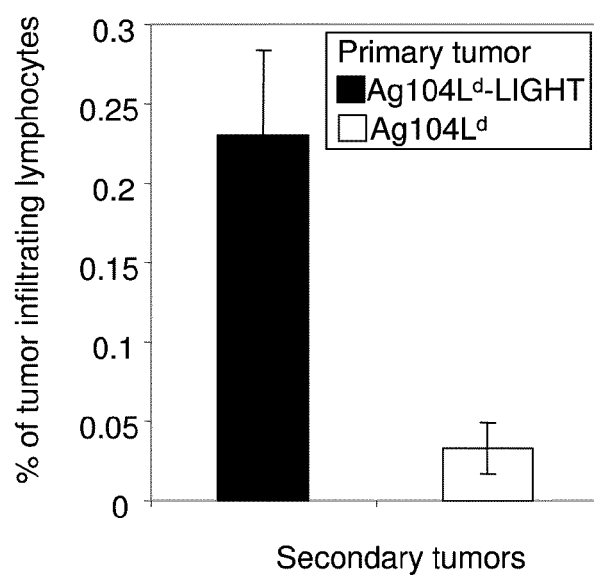

Activated Tumor Antigen-Specific T Cells Generated from the Primary Tumor Move to the Distal Tumor It was determined whether the exiting tumor antigen-specific T cells could then patrol peripheral tissues to infiltrate a distal secondary tumor mass which does not express mutant LIGHT. To avoid the potential for systemic spreading of Ad-mutant LIGHT that could reach the distal tumor, Ag104L$^d$ or mutant LIGHT-expressing Ag104L$^d$ tumor lines were used to address whether local presence of mutant LIGHT in primary tumor can evoke an anti-tumor immunity on the distal tumors. The same model system described herein, in which 2C T cells were adoptively transferred to Ag104L$^d$ tumor-bearing OT-1 mice was used, but this time inoculated each of the OT-1 mice with two tumors. The primary tumor was either 10$^6$ Ag104L$^d$ or Ag104L$^d$-mutant LIGHT, while the secondary tumor was 10$^5$ Ag104L$^d$. 10-14 days post tumor challenge, CFSE-labeled 2C T cells were transferred. Proliferation of the 2C T cells was evaluated at days 3, 5 and 10 after adoptive transfer inside the tumors. Three days after transfer, CFSE$^{hi}$ non-proliferating 2C cells were present in the mutant LIGHT-expressing Ag104L$^d$ primary tumor. Subsequent proliferation of these 2C T cells was observed 5 days after transfer, as indicated by the in situ dilution of CFSE. By day 10, a larger number of proliferated 2C T cells was found in Ag104L$^d$-mutant LIGHT tumors (FIG. 16B). In the secondary Ag104L$^d$ tumor, the presence of diluted CFSE labeled 2C T cells was detected at a higher frequency in mice bearing Ag104L$^d$-mutant LIGHT tumor compared to those bearing Ag104L$^d$ (FIGS. 16 B and C). Only a small population of tumor infiltrating 2C T cells was detected in both the primary and the secondary tumor of the mice bearing two Ag104L$^d$ tumors (FIG. 16C). These data support the notion that some activated antigen-specific T cells are able to migrate out of the primary tumor after mutant LIGHT treatment and traffic to the secondary tumor.

Example 13

Ad-Mutant LIGHT at the Primary Tumor Generates more CTLs

Figure 16D:
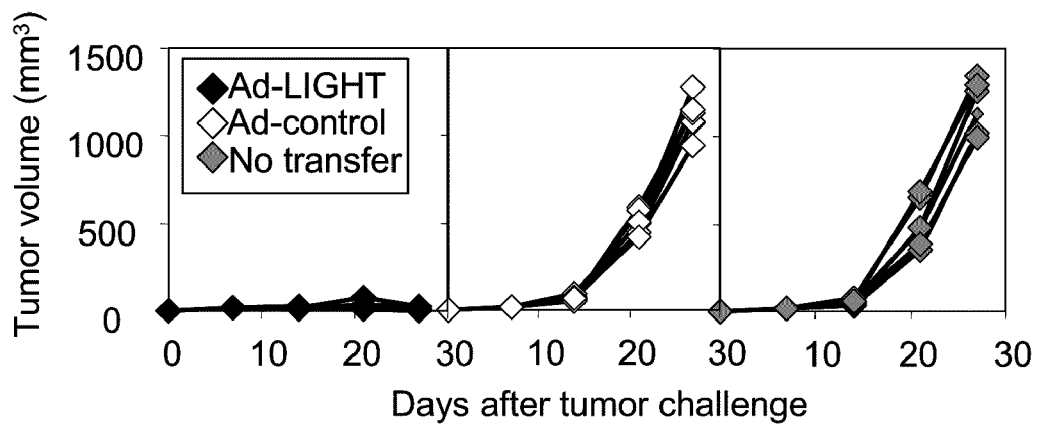

Antigen-specific T cells activated in the mutant LIGHT-mediated environment were capable of migrating to a distal tumor that did not express mutant LIGHT. To test whether Ad-mutant LIGHT can generate more CTL against tumor from primary tumor, which then circulate systemically for the rejection of distal tumor, adoptive transfer experiments were performed to investigate whether the T cells from lymphoid organs of treated mice are capable of mediating the rejection of established tumors. 4T1 model cannot be used for these experiments since the secondary lymphoid tissues are often contaminated with metastatic 4T1 tumor cells 2 weeks after tumor challenge. About $10^5$ Ag104L$^d$ tumor cells were inoculated to the C3B6F1 mice, then treated with $5\times10^9$ p.f.u. of Ad-mutant LIGHT or Ad-control 14 days post tumor inoculation. At 21 days the spleen and lymph nodes were collected from the treated mice and the T cells were purified and adoptively transferred $10^7$ of these T cells to C3B6F1 mice bearing an Ag104L$^d$ tumor that has been established for 7 days. The mice that received T cells from Ad-mutant LIGHT-treated mice all rejected their tumors while the ones that received T cells from Ad-control-treated mice died of tumor burdens (FIG. 16D). This result suggested that activated antigen-specific T cells present in circulation after Ad-mutant Mutant LIGHT treatment, but not control virus, are sufficient to reject established distal tumors. These results demonstrate that local treatment of tumor with Ad-mutant LIGHT can generate more CTL entering the draining LN, which then attack established distal tumors.

Example 14

Figure 17A:
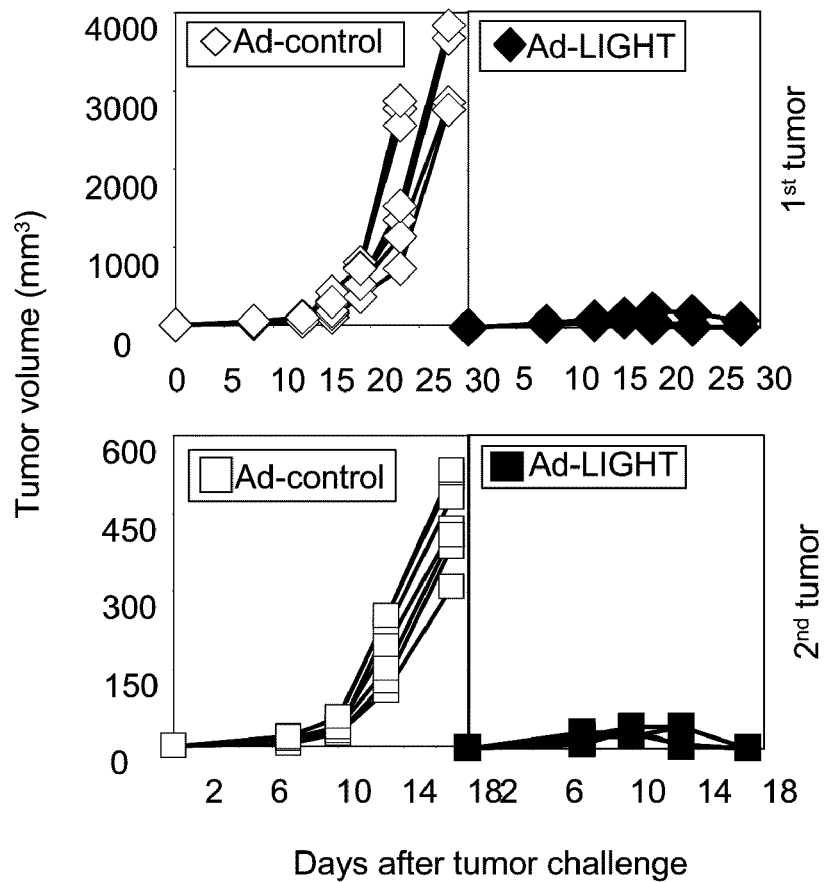
FIG. 17 shows that Ad-mutant LIGHT treatment on the primary tumor induces strong anti-tumor immune responses in the secondary tumor. Each of the C3B6F1 mice was inoculated with $10^5$ Ag104L$^d$ and $10^5$ Ag104L$^d$ tumor cells 6 days after primary tumor challenge. The intra-tumor Ad-mutant LIGHT treatment with $5\times10^{10}$ adenovirus particles on the primary tumor inoculation was given 5 days after the secondary tumor inoculation. The growth of both of the primary and secondary tumors was monitored (A). The percentage of CD8$^+$ T cells among Ly5.2$^+$ cells, and IFN-γ-producing CD8+ T cells among CD8+ T cells in the DLN, spleen, primary and secondary tumors were examined (B) and the statistics was calculated (C). The spleen and tumor tissues were harvested 7 days after Ad-mutant LIGHT or Ad-control treatment, ground the tissues and collected the supernatant for cytokine measurement (D).
Figure 17B:
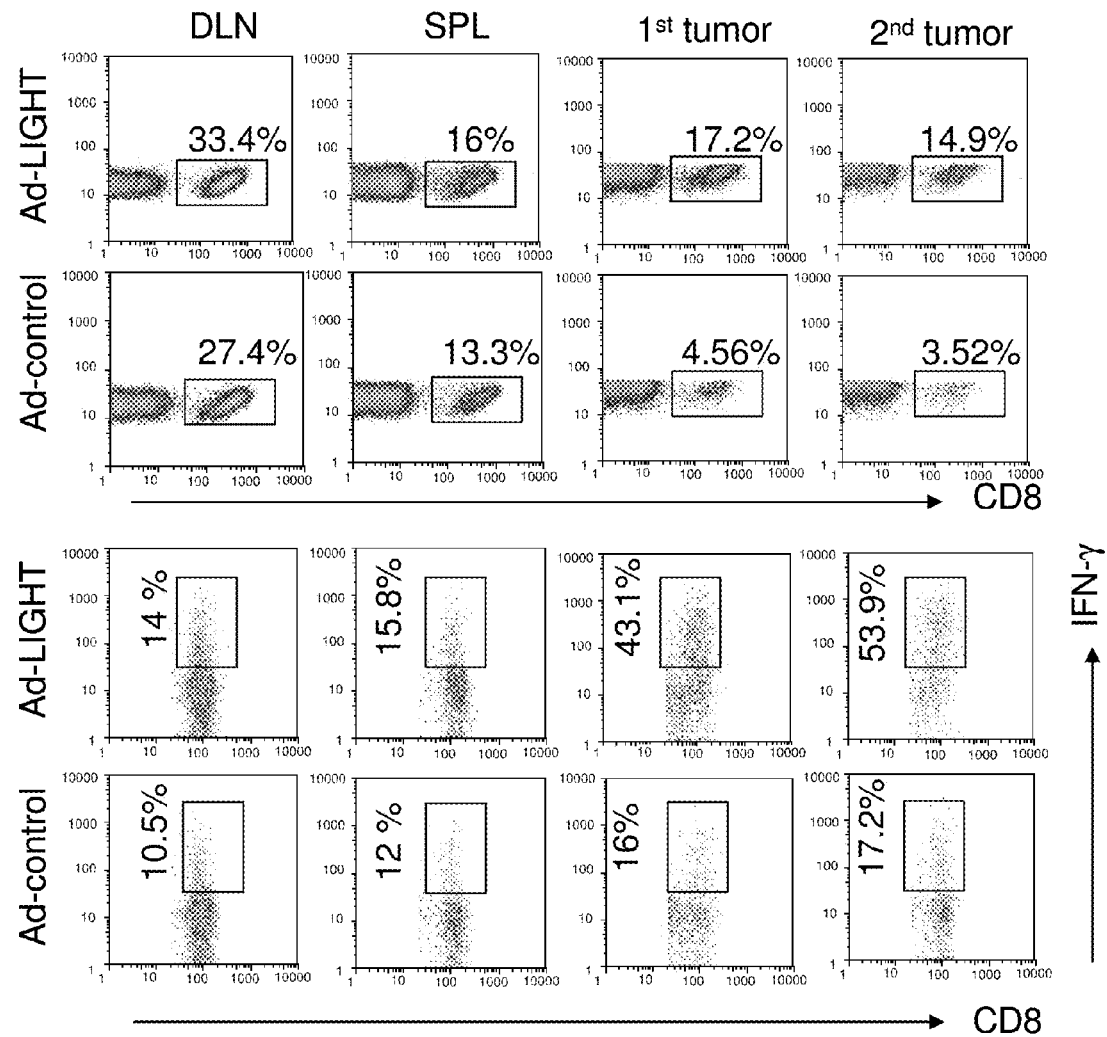

Ad-Mutant LIGHT Treatment at Local Site Enhances T Cell-Mediated Responses at Local and Distal Sites To assess whether Ad-mutant LIGHT treatment directly alters tumor environment at the primary tumor and the distal site, C3B6F1 mice were inoculated with two subcutaneous Ag104L$^d$ tumors 6 days apart, to mimic development of a new subcutaneous metastasis. The intra-tumoral Ad-mutant LIGHT treatment of the primary tumor was given 5 days after the secondary tumor inoculation. Both the primary and secondary tumors were rejected in the mice treated with Ad-mutant LIGHT while the mice treated with Ad-control developed tumor progression (FIG. 17A). Because the effect of Ad-mutant LIGHT is CD8-mediated, the percentage of CD8$^+$ T cells among the Ly5.2$^+$ leukocytes, and IFN-$\gamma$-producing effectors among all the CD8$^+$ T cells in the DLNs, spleen, primary and secondary tumors were examined. The number of CD8$^+$ T cells and IFN-$\gamma$-producing effector CD8$^+$ T cells increased dramatically in both the primary and the secondary tumors after Ad-mutant LIGHT treatment (FIGS. 17B and C). The development of anti-tumor immunity leading to tumor regression is generally associated with a change of the cytokine environment. To examine the cytokine millieu in the lymphoid organs, and inside the tumor itself, the spleen and tumor tissues 7 days after Ad-mutant LIGHT or Ad-control treatment were harvested, the tissues were ground and the supernatant was collected for cytokine measurement. None of the cytokines that was tested, TNF-$\alpha$, IFN-$\gamma$, IL-2, IL-4, IL-5, IL-6, significantly changed in the spleen of mice treated with Ad-mutant LIGHT comparing to the ones treated with Ad-control. However, TNF-$\alpha$ and IFN-$\gamma$ increased considerably in both of the primary and the secondary tumors with Ad-mutant LIGHT treatment (FIG. 17D). Thus, tumor rejection was accompanied by an increase of CD8$^+$ T cells, enhancement of the IFN-$\gamma$ production by the effector CD8$^+$ T cells, and augmentation of inflammatory cytokines TNF-$\alpha$ and IFN-$\gamma$ inside both the primary and secondary tumors. These results demonstrated that Ad-mutant LIGHT treatment on the primary tumor can generate large numbers of effector cells from the tumor and these cells can efficiently survey peripheral tissues and respond to distal tumors, leading to the regression of a secondary tumor burden.

Example 15

Gene Modification of Light Enhances its Expression in "293 Cells"

Figure 18:
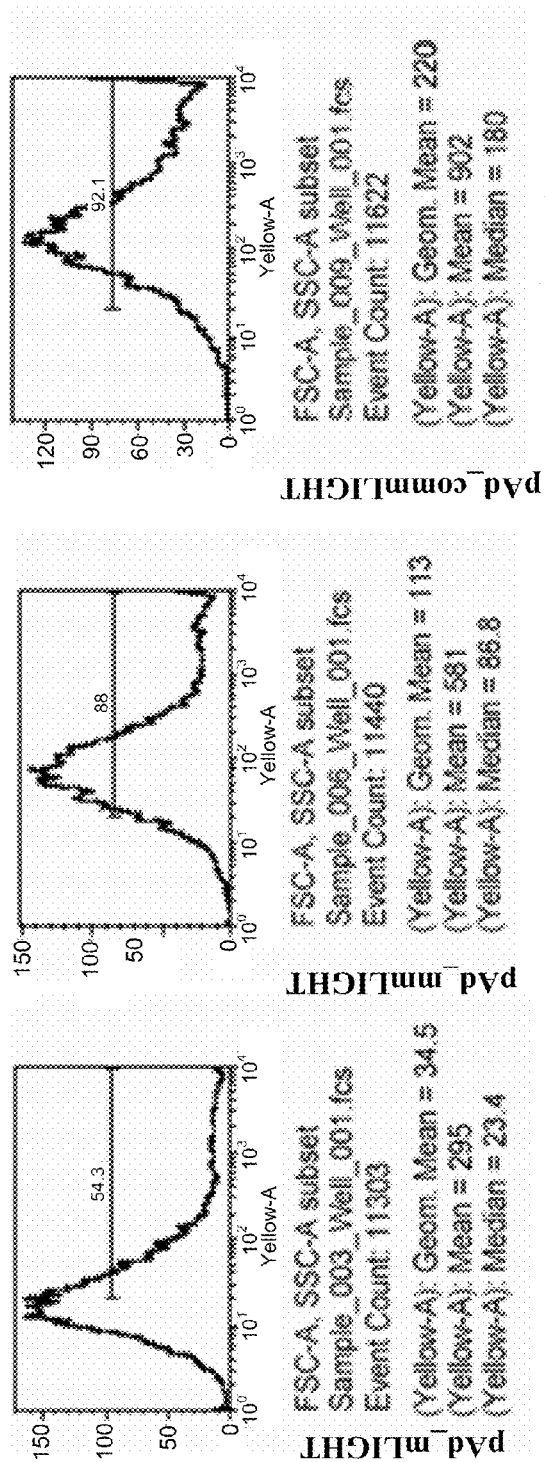
FIG. 18 shows LIGHT and mutant LIGHT expression in "293 cells". 293 cell line, which is commonly used for transient expression of the gene, was infected with murine ad-wt LIGHT or ad-mutant LIGHT, ad-mutant LIGHT with further codon modification that enhances RNA expression. After 48 hours, $5\times10e5$ of the cell line was stained for 1 ung of murine LTbR-Ig (followed by anti-Ig FITC for its surface expression of LIGHT. Upper panel shows the histogram of flowcytometry. Cells were also examined visually by fluorescent microscopy. Representative results are shown in lower panel. Wt LIGHT is poorly expressed on 293 cell line while mutant LIGHT expression was enhanced. Codon modification of mutant LIGHT expressed its highest level (see example 15). Therefore, the data confirms that gene modification and mutation leads to higher expression of LIGHT on cell surface for its biological activity.
Figure 19:
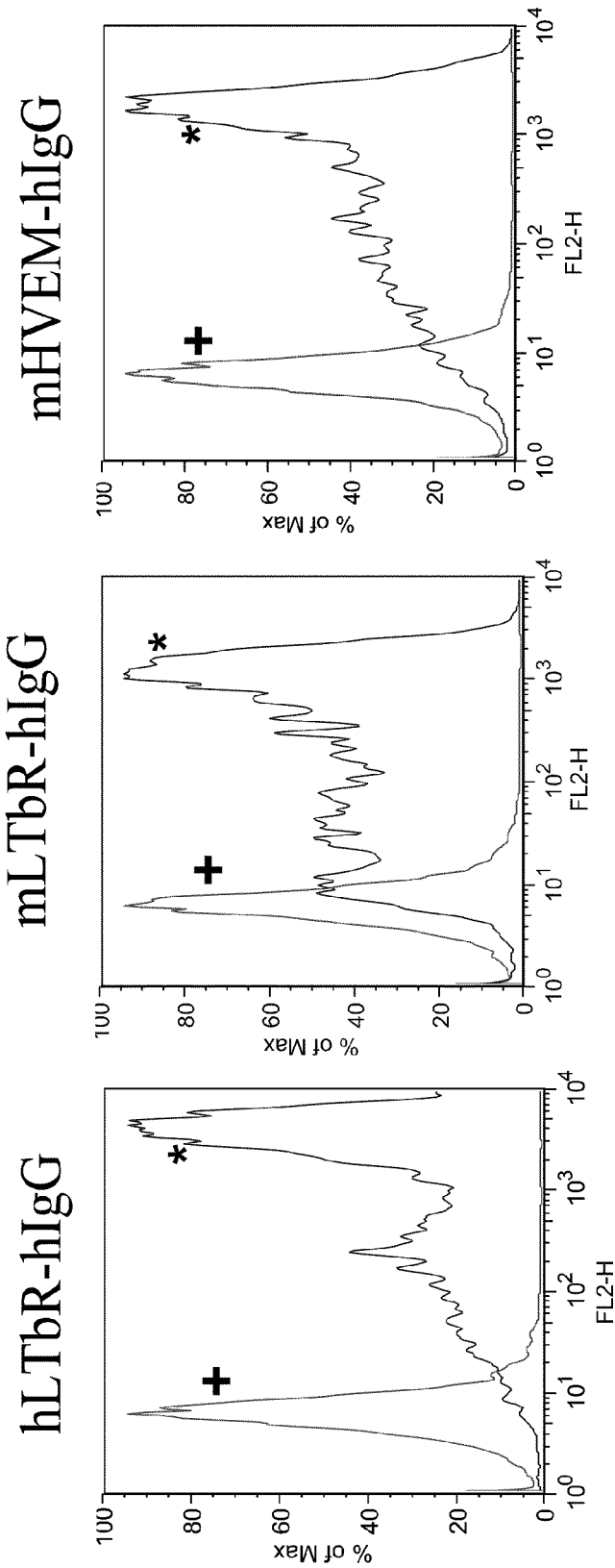
FIG. 19 shows expression of human mutant LIGHT in AD293 cells/adv-cmv-null (+) and AD293 cells/adv-cmv-mutant hLIGHT#7 (*). AD293 cell line was infected with control adenovirus with CMV promoter alone (+) or adenovirus-LIGHT (*). The ratio of cell v. viral units is 1:100. After 48 hours, the cell line was stained with human LTbR-Ig, or mouse LTbR-Ig, and mouse HVEM-Ig. Mutant human LIGHT can bind to human LTbR, mouse LTbR, and mouse HVEM, suggesting the mutant LIGHT does not lose its capacity to bind its two known receptors.
Figure 20:
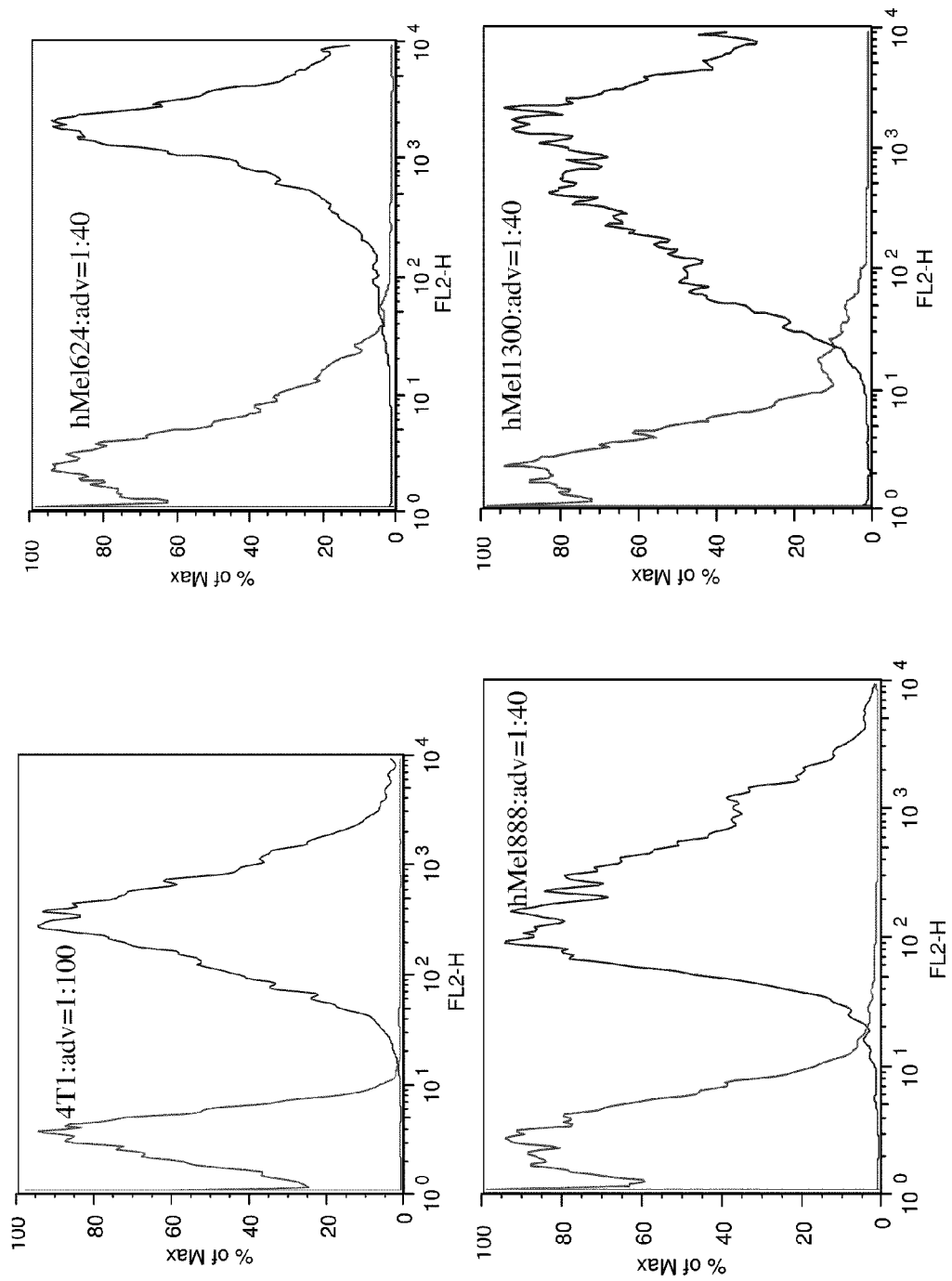
FIG. 20 illustrates human mutant LIGHT expression on mouse and human tumor cell lines. hMe: human melanoma. Three human lines are included. 1:40 means one tumor: 40 adenovirus infected unit. 4T1 is a mouse line to express mutant LIGHT, used here as a positive control. The staining was done 24 hours after infection. Red line is ad-LIGHT infected cells while blue is parent tumor (with control ad-Laz).

This example demonstrates mutant LIGHT expression in 293 cells (FIG. 18). 293 cells, a human kidney cell line, are commonly and easily used for transient expression of gene at relative high level of gene. 293 cells were seeded in 6 well plate and transfected with 2 µg DNA of pAdCMVmLIGHT (wild type murine LIGHT), pAdCMVmmLIGHT (mutant murine LIGHT) or pAdCMVcommLIGHT (codon optimized mutant murine LIGHT by GNENART, Berlin, Germany). Codon modification is to optimize gene codon to allow higher expression of protein without changing protein sequences. Transfection was performed using Lipofectmin 2000 reagent. 48 hours after transfection, cells were detached and incubated with recombinant mLTbR-huFc protein (10 µg/ml) followed by staining with PE conjugated Donkey anti-human IgG antisera. Cells were washed and analyzed by flowcytometry (BD FACSArray Bioanalyzer). Transfection were carried out in triplicates and only one representative result is shown. Upper panel shows the histogram of flowcytometry. Cells were also examined visually by fluorescent microscopy. Representative results are shown in lower panel. (see FIG. 18). High expression of LIGHT is required to have stronger response. However, protease digestion of LIGHT often reduces its stability on cell surface. This example showed that our gene modification and mutation greatly enhances LIGHT expression on cell surface.

Example 16

Coupling or Conjugating Mutant LIGHT Expression to a Tumor Targeting Agent

In an aspect, to enable delivery of mutant LIGHT expressing delivery system or an equivalent delivery system, mutant LIGHT can be coupled or conjugated to a tumor targeting agent such as a tumor specific antibody. For example, a tumor specific antibody can be conjugated to LIGHT can be used to selectively deliver fusion protein to tumor site. In addition, a tumor specific antibody can be designed to be expressed in the surface of a viral delivery system or a liposome vehicle can be coated with a tumor specific antibody. The delivery vehicle expressing the mutant LIGHT and harboring the tumor targeting agent will first target the specific tumor cell and then transform the tumor cell to express mutant LIGHT on the surface of tumor cells. This targeted mutant LIGHT expression on the surface of the tumor cells will induce chemokines on stromal cells surrounding tumor to attract and initiate priming of T-cells. Such treatments are suitable to all tumors, especially solid tumor. 4T1, MC38, B16, and mastocytoma were treated with ad-LIGHT and showed reduction of primary and/or secondary tumor. Therefore, LIGHT-antibody can be used to target various tumors, especially their metastasis. For example, through systemic injection, anti-her2/neu antibody with LIGHT can carry LIGHT to metastatic tumor that expresses her2/neu and then can generate local immune response to clear tumor. Therefore, the fusion protein can be delivered through any systemic and local route and the fusion protein will be more localized to tumor due to the specificity of antibody or another agent to tumor antigens.

TABLE 1

Mutant LIGHT augments host's resistance to Ag104L$^d$ tumor challenges

| Tumor cells injected[a] | | Incidence of tumor growth[b] | (Percentage) |
|---|---|---|---|
| Ag104L$^d$ | $5 \times 10^6$ | 10/10 | (100) |
| | $1 \times 10^6$ | 11/11 | (100) |
| | $5 \times 10^5$ | 10/10 | (100) |
| | $1 \times 10^5$ | 5/5 | (100) |
| | 5/10$^4$ | 4/4 | (100) |
| | $1 \times 10^4$ | 4/4 | (100) |
| Ag104L$^d$-mutant LIGHT | $5 \times 10^5$ clone H10 | 0/10 | (0) |
| | $1 \times 10^6$ clone H10 | 0/11 | (0) |
| | 5/10$^6$ clone H10 | 0/10 | (0) |
| | 5/10$^6$ bulk | 0/10 | (0) |

[a]Number of tumor cells as indicated were injected subcutaneously to C3B6F1 mice.
[b]The results were pooled from 1 to 3 independent experiments.

TABLE 2

Incidence of Ag104Ld tumors in C3B6F1 mice

| Tumor cells injected | Treatment | Incidence of tumor growth[a] | (Percentage) |
|---|---|---|---|
| $10^6$ Ag104L$^d$ | no treatment | 16/16 | (100) |
| $10^6$ Ag104L$^d$ | CD8-depletion[b] | 6/6 | (100) |
| $10^6$ Ag104L$^d$-LIGHT$^m$ | No treatment | 0/6 | (0) |
| $10^6$ Ag104L$^d$-LIGHT$^m$ | CD8-depletion[b] | 6/6 | (100) |
| $10^6$ Ag104L$^d$-LIGHT$^m$ | LTβR-Ig[c] | 6/6 | (100) |
| $10^7$ Ag104L$^d$ | $10^6$ Ag 104L$^d$-LIGHT 40 days ago | 0/5 | (0) |
| $10^7$ Ag104L$^d$ | $10^6$ Ag 104L$^d$-LIGHT 60 days ago | 0/5 | (0) |

[a]The results were pooled from 1 to 4 independent experiments.
[b]CD8+ cells were depleted by anti-CD8 antibody. Depletion was confirmed by checking peripheral blood samples.
[c]100 μg of LTβR-Ig was injected on the day of tumor challenge to each recipient.

The introduction of mutant LIGHT, a ligand for stroma expressed lymphotoxin receptor and T cell expressed HVEM, inside the tumor environment elicited high level of chemokines and adhesion molecules, accompanied by massive infiltration of naïve T lymphocytes. In an aspect, mutant LIGHT, has a proteolytic site EKLI (SEQ ID NO: 4) from positions 79-82 deleted from the amino acid sequence of normal murine LIGHT (FIG. 3A) (Tamada et al., 2000). Mutant LIGHT enhances rejection of an established, highly progressive parental tumor at local and distal sites. Mutant LIGHT-expressing tumor cells are the basis for a clinically relevant therapeutic and prophylactic vaccines to eradicate well-established parental tumors and prevent new tumors forming through metastasis.

Materials and Methods

Mice, Cell Lines, and Reagents. Female C3HXC57BL/6 F1 (C3B6F1) mice, 4-8 weeks old were purchased from the National Cancer Institute, Frederick Cancer Research Facility, (Frederick, Md.). C57BL/6-RAG-1-deficient (RAG-1$^{-/-}$) mice were purchased from the Jackson Laboratory (Bar Harbor, Me.). H-Y TCR transgenic mice (H-Y mice) on the RAG-2-deficient/B6 background were purchased from Taconic Farms (Germantown, N.Y.). 2C TCR transgenic mice on RAG-1-deficient background bred into B6 for 10 generations (2C mice) were provided by J. Chen (Massachusetts Institute of Technology, Boston, Mass.). OT-1 TCR transgenic mice (OT-1 mice) were provided by A. Ma (The University of Chicago). RAG-1$^{-/-}$, H—Y, 2C, OT-1 mice were bred and maintained in the specific pathogen-free facility at the University of Chicago. Animal care and use were in accord with institutional guidelines.

The AG 104A fibrosarcoma grew out spontaneously in an aging C3H mouse and was adapted to culture as described (Ward 1989 JEM). The AG104A expressing murine H-2L$^d$ (AG104-L$^d$), the transfectant of AG104A cells, has been described previously (Wick M, 1997, JEM). These tumor cell lines were maintained in DMEM (Mediatech) supplemented with 10% FCS (Sigma-Aldrich), 100 U/ml penicillin, and 100 μg/ml streptomycin (BioWhittaker). The hybridoma cell lines producing anti-L$^d$ (clone 30-5-7) and anti-2C TCR (1B2)

TABLE 3

Treatment with Ag104L$^d$-mutant LIGHT eradicates established tumors at distal sites.

| Ag104L$^d$ tumor cells injected | Days of tumor establishment[a] | Treatment | Incidence of tumor growth | (Percentage) |
|---|---|---|---|---|
| $10^4$ | 20 days | No treatment | 4/4 | (100) |
| $10^4$ | 20 days | 105 Ag104L$^d$-mutant LIGHT[b] | 0/4 | (0) |
| $5 \times 10^4$ | 20 days | No treatment | 4/4 | (100) |
| $5 \times 10^4$ | 20 days | 106 Ag104L$^d$-mutant LIGHT[b] | 2/4 | (50) |
| $10^6$ (primary) + $5 \times 10^4$(distal) | 14 days | Surgical removal of primary tumor | 4/4 | (100) |
| $10^6$ (primary) + $5 \times 10^4$(distal) | 14 days | Surgical removal of primary tumor & $10^6$ Ag104L$^d$-mutant LIGHT[b] | 0/4 | (0) |
| $5 \times 10^6$ (Primary) + $10^6$(distal) | 20 days | Surgical removal of primary tumor | 4/4 | (100) |
| $5 \times 10^6$ (primary) + $10^6$(distal) | 20 days | Surgical removal of primary tumor & $10^6$ Ag104L$^d$-mutant LIGHT[b] | 2/4 | (50) |

[a]Days of growth of subcutaneously injected Ag104L$^d$ in the hosts before treatment started
[b]$10^6$ Ag104L$^d$- mutant LIGHT tumor cells were injected subcutaneously at other site than where Ag104L grew.

antibodies were obtained from D. Sachs (National Institutes of Health, Bethesda, Md.) and T. Gajweski (The University of Chicago), respectively.

Monoclonal antibodies produced by hybridomas were purified from the culture supernatant with protein G column by standard procedure. The 1B2 antibody was conjugated to FITC or biotin by the Monoclonal Antibody Facility of The University of Chicago. PE-coupled anti-CD8 antibody, Cychrome (CyC)-coupled streptavidin, CyC-coupled anti-CD44 antibody, PE-coupled anti-CD62L antibody and PE-coupled Th1.2 antibody were purchased from BD Biosciences. FITC-conjugated-goat-anti-mouse IgG was purchased from Caltag. PE-coupled streptavidin was purchased from Immunotech. PE-coupled donkey anti-human IgG was purchased from Jackson Immunological Research Lab (West grove, Pa.). Biotinylated goat anti-SLC antibody was purchased from R&D systems Inc. (Minneapolis, Minn.). AP conjugated rabbit anti-goat Ig antibody was purchased from Vector Laboratories Inc. (Burlingame, Calif.). Purified goat anti-SLC antibody was purchased from Pepro-Tech (Rock hill, NJ). Collagenase (type 4) was purchased from Sigma-Aldrich. CFSE was purchased from Molecular Probes. HVEM-Ig and LTβR-Ig fusion proteins used in this study have been described previously.

Generation of B7.1 or mutant LIGHT Expression Vectors and Clones To generate pMFG-S-mutant LIGHT, pcDNA3.1-mutant LIGHT was digested with NcoI and BamHI and ligated to a NcoI and BamHI-digested the pMFG-S-TPA plasmid (Dr. Mulligan R C, Massachusetts Institute of Technology, Boston, Mass.). ϕNxEco packaging cells producing the viruses containing mutant LIGHT was generated by transient transfection with MFG-S-mutant LIGHT by calcium precipitation method. The expression of mutant LIGHT by infected AG104L$^d$ tumor cells (AG104L$^d$-mutant LIGHT bulk) was assayed by staining the cells with a rabbit antiserum recognizing mutant LIGHT. Subsequently, the infected mutant LIGHT-expressing AG104L$^d$ tumor cells were cloned by limiting dilution method. AG104L$^d$-mutant LIGHT clone H10 was one of these clones used in the experiments.

Tumor Growth In Vivo. Tumor cells were injected subcutaneously into the lower back, that is, 0.5-1 cm above the tail base of the mice. Tumor growth was measured every 3 to 4 days with a caliper. Size in cubic centimeters was calculated by the formula $V=\pi abc/6$, where a, b, and c are three orthogonal diameters.

Histology. Tumor tissues for histology examination were collected at time indicated and fixed in 10% neutral buffered formalin, processed to paraffin embedment, and stained with hematoxylin and eosin. For immunohistochemical staining of SLC, tumor tissues were harvested, embedded in OCT compound (Miles-Yeda, Rehovot, Israel) and frozen at −70° C. Frozen sections (5-10 μm thick) were fixed in cold 2% formalin in PBS and permeablized with 0.1% saponin/PBS. The sections were preblocked with 5% goat serum in 0.1% saponin/PBS for half an hour at room temperature in a humidified chamber. Staining for SLC was done by first incubating with biotinylated goat anti-SLC antibody (R&D systems Inc. Minneapolis, Minn.) at a 1/25 dilution in blocking buffer. Alkaline phosphatase conjugated rabbit anti-goat Ig antibody (Vector Laboratories Inc. Burlingame, Calif.) was added 2 h later. For immunofluorescence staining, sections were blocked with 2% normal mouse serum, rabbit serum, and goat serum in PBS for half an hour at room temperature in a humidified chamber. Blocking solution was replaced with 50 μl of primary Abs, PE-conjugated anti-Th1.2 (BD PharMingen), or PE-conjugated anti-CD8 (BD PharMingen), diluted 1/100 in blocking solution, and sections were incubated for 1 h at room temperature in a humid chamber. Specimens were mounted in Mowiol 4-88 (BD Biosciences, La Jolla, Calif.) containing 10% 1,4-diazobicyclo [2.2.2]octane. Samples were analyzed within 48 h using a Zeiss Axioplan microscope (Zeiss, Oberkochen, Germany) and a Photometrics PXL CCD camera (Photometrics, Tucson, Ariz.). No-neighbor deconvolution was performed using Openlab v2.0.6 (Improvision, Lexington, Mass.).

ELISA for CCL21. Tumor homogenates were prepared and assayed for CCL21. Comparable amount of tumor tissues from tumor-bearing mice were collected and weighed, homogenized in PBS that contained protease inhibitors, and the supernatants were collected by centrifugation. Polystyrene 96-well microtiter plates (Immulon 4, Dynatech Laboratories, Chantilly, Va.) were coated with goat anti-mouse CCL21 at 2 μg/ml in PBS and were then blocked with 0.1% bovine serum albumin (BSA) in PBS for 30 min at room temperature. After washing, serial dilutions of standards of known concentrations (Recombinant CCL21, 50 ng/ml, R&D) and samples were added and incubated for 2 h at room temperature. After 3 washes, biotinylated rabbit anti-SLC Ab was added to the wells. After 2 h incubation and washing, 50 μl of a 1/1000 diluted alkaline phosphatase-conjugated avidin (Dako) was added for 1 h and then developed. Color development was measured at 405 nm on an automated plate reader (Spectra-Max 340, Molecular Devices, Sunnyvale, Calif.) and The amount of CCL21 was determined by ELISA from the standard curve, and normalized according to tissue weight. Data are mean±s.d.

Real-time quantitative RT-PCR assay. Real-time PCR was performed. Total RNA from tumors was isolated with Absolute RNA miniprep Kit (Stratagene, La Jolla, CA) and digested with DNaseI (Life Technologies, Grand Island, NY) to remove chromosomal DNA. The remaining DNaseI was inactivated at 75° C. for 20 min and integrity of RNA was assessed by visualization of ethidium bromide-stained gels. 5 μg of total RNA was reverse transcribed into cDNA with the First Strand cDNA Synthesis kit (Amersham Pharmacia, Piscataway, NJ). The real-time quantitative PCR analysis was done on the ABI Prism 7700-sequence detection system (PE Applied Biosystems). The primer sequences for CCL21 were 5'-AGACTCAGGAGCCCAAAGCA-3' (SEQ ID NO: 5) (forward primer) 5'-GTTGAAGCAGGGCA AGGGT-3' (SEQ ID NO: 6) (reverse primer), and the probe for CCL21 was 5'-CCACCTCATGCTGGCCTCCGTC-3' (SEQ ID NO: 7). The primers for MAdCAM-1 were 5'-GACACCAGCT-TGGGCAGTGT-3' (SEQ ID NO: 8) (forward primer) and 5'-CAGCATGCCCCGTACAGAG-3' (SEQ ID NO: 9) (reverse primer), and the probe for MAdCAM-1 was 5'-CA-GACCCTCCCAGGCAGCAGTATCC-3' (SEQ ID NO: 10). The primers for GAPDH were 5'-TTCACCACCATG-GAGAAGGC-3' (SEQ ID NO: 11) (forward primer) and 5'-GGCATGGACT GTGGTCATGA-3' (SEQ ID NO: 12) (reverse primer), and the probe for GAPDH was 5'-TGCATC-CTG CACCACCAACTGCTTAG-3' (SEQ ID NO: 13). The CCL21 and MAdCAM-1 probes were labeled with 6-carboxy-fluorescein (FAM). The GAPDH probe was labeled with tetrachloro-6-carboxy-fluorescein (TET). Each cDNA sample was amplified in duplex for CCL21 and GAPDH or MAdCAM-1 and GAPDH with the TaqMan Universal PCR master mixture containing AmpliTaq Gold DNA Polymerase according to the manufacturer's instructions (PE Applied Biosystems). PCR conditions were 2 min at 50° C., 10 min at 95° C., 15 s at 95° C. and 1 min at 60° C. for 40 cycles. The concentration of target gene was determined using the comparative $C_T$ (threshold cycle number at cross-point between amplification plot and threshold) method and normalized to the internal GAPDH control.

Tumor tissue chemokine microarray For these experiments, GEArray Q series Mouse Chemokines and Receptors Gene Array membrane (SuperArray, Bethesda, Md.) were used. Total RNA from tumors was isolated with Absolute RNA miniprep Kit (Stratagene, La Jolla, Calif.) and digested with DNaseI (Life Technologies, Grand Island, N.Y.) to remove chromosomal DNA. The remaining DNaseI was inactivated at 75° C. for 20 min. Integrity of RNA was assessed by visualization of ethidium bromide-stained gels. The microarrays were employed according to the manufacturer's instructions. In brief, using reagents provided, cDNA was prepared from total RNA by reverse transcription with MMLV reverse transcriptase, radiolabeled using [−32P] dCTP (3,000 Ci/mM), then hybridized under precisely specified conditions to a positively charged nylon membrane containing the arrayed DNA. After washing, the arrays were visualized by phosphorimager. Loading was adjusted based on intensity of hybridization signals to the housekeeping genes, PUC18, actin and GAPDH, then gene expression was quantitated after the digital image recorded by phosphorimager was converted to digital data by using ImageQuant software. The raw data was analyzed using the GEArrayAnalyzer software according to manufacturer's instructions.

T-cell co-stimulation assay. T cells were purified by a negative selection method in the magnetic field as instructed by the manufacture (Miltenyi Biotec, Auburn, Calif.). The purity of isolated T cells was greater than 95%, as assessed by flow cytometry using monoclonal antibody against CD3. Plates coated with 0.2 g/ml monoclonal antibody against CD3 were further coated at 37° C. for 4 h with Mutant LIGHT-flag. After being washed, purified T cells ($1 \times 10^6$ cells/ml) were cultured in the wells. Monoclonal antibody against CD28 (1 μg/ml) was used in soluble form. In all assays, the proliferation of T cells was assessed by the addition of 1 Ci/well $^3$H-thymidine during the last 15 h of the 3-day culture. 3H-thymidine incorporation was measured in a TopCount microplate scintillation counter (Packard instrument, Meriden, Conn.).

Analysis of Cells by FACS. In order to confirm that mutant LIGHT binds to LTβR and HVEM, AG104L$^d$ tumor cells transfected with mutant LIGHT (AG104Ld-mutant LIGHT) were incubated with LTβR-Ig or HVEM-Ig (0.02 mg/mL), washed, and stained with PE-coupled donkey anti-human IgG or FITC-coupled goat anti-mouse IgG, respectively. For analysis of L$^d$ expression, tumor cells were incubated with the anti-L$^d$ antibody, washed, and incubated with FITC-coupled anti-mouse IgG antibody. For detection of proliferation of CFSE-labeled 2C T cells, isolated lymph node (LN) cells, splenocytes, and tumor-infiltrating T cells (TIL) were stained with biotinylated 1B2 antibody, washed, and stained with CyC-coupled streptavidin and PE-coupled anti-CD8. For analysis of CFSE-labeled 2C T cells and CD44 expression, isolated LN cells, splenocytes or TIL were stained with biotinylated 1B2 antibody, washed, and stained with a mixture of PE-coupled streptavidin and CyC-coupled anti-CD44. For analysis of CFSE-labeled 2C T cells and CD62L expression, isolated LN cells, splenocytes or TIL were stained with biotinylated 1B2 antibody, washed, and stained with CyC-coupled streptavidin and PE-coupled anti-CD62L. Samples were analyzed on a FACScan and data was analyzed with CELLQuest or FlowJo softwares.

Adoptive Transfer of 2C T Cells. LN cells and splenocytes were isolated from 2C mice and CD8$^+$ T cells were negatively selected with a CD8$^+$ T cell enrichment kit (Miltenyi Biotec, Auburn, Calif.). When analyzed, >90% of the enriched CD8$^+$ cells expressed the 2C receptor. Approximately $3 \times 10^6$ 2C T cells were transferred into H-Y or OT-1 mice for assays of tumor growth. The same number of 2C T cells was transferred to each mouse in each experiment. To transfer CFSE-labeled T cells, T cells at a concentration of $2 \times 10^7$/ml were labeled with 10 μM CFSE in PBS at 37° C. for 30 min. The cells were quenched with equal volume of FCS for 1 min and washed three times, and $3 \times 10^6$ CFSE-labeled T cells were injected intravenously into the retro-orbital plexus in a 0.2-ml volume to the tumor-bearing mice. Cells were isolated from the inguinal lymph nodes (DLNs), the other lymph nodes (non-draining lymph nodes [NDLN]), spleen or tumors at the time indicated.

Cell depletions and in vivo blockage of Mutant LIGHT activity with LTβR-Ig Mice were depleted of lymphocyte subsets by standard procedures (current protocol for immunology) using monoclonal antibody (mAb) GK1.5 (Dialynas DM JI 1983) for CD4+ cells, and mAb 2,34 for CD8+ cells (Sarmiento M 1980 JI). Examination of splenocytes and lymph node cells by FACS revealed that the depleted subset represented <0.5% of the total lymphocytes, with normal levels of other subsets. To block Mutant LIGHT in mice, the LTβR-Ig (100 μg/injection) were given the same day and a week after tumor challenge, intra-peritoneally.

Cell Isolation from tumor tissue. The mice were first bled to decrease the blood contamination of tumor tissue. The tumor tissues were collected, washed in the PBS, cut into pieces, and resuspended in DMEM supplemented with 2% FCS and 1.25 mg/ml collagenase D (collagenase D solution) for 40 min in a 37° C. shaking incubator. The single cell suspension was collected after 40 min, and the cell clumps were digested for another 40 min in the collagenase D solution until all tumor tissue had resolved into a single cell suspension.

Delivery of LIGHT and Mutant LIGHT expressing cells. Delivery of a nucleic acid encoding mMutant LIGHT into a patient may be either direct, in which case the patient is directly exposed to the nucleic acid or nucleic acid-carrying vectors, or indirect, in which case, tumor cells obtained from a biopsy are first transformed with the nucleic acids in vitro, irradiated and then transplanted into the patient. These approaches are routinely practiced in gene therapies for suppressing tumors or treating other illness.

Delivery of nucleic acids. The nucleic acid sequences encoding mutant LIGHT are directly administered in vivo or can be introduced into tumor cells in vitro, where they are expressed to produce mutant LIGHT protein. This can be accomplished by any of numerous methods known in the art, e.g., by constructing them as part of a suitable nucleic acid expression vector and administering it so that they become intracellular, e.g., by infection using defective or attenuated retroviral or other viral vectors, or by direct injection of naked DNA, or by use of microparticle bombardment, or coating with lipids or cell-surface receptors or transfecting agents, encapsulation in liposomes, microparticles, or microcapsules, or by administering them in fusion with a peptide that enters the nucleus, by administering by coupling with a ligand subject to receptor-mediated endocytosis (which can be used to target cell types specifically expressing the receptors), etc. Alternatively, the nucleic acid can be introduced intracellularly and incorporated within host cell DNA for expression, by homologous recombination. Mode of delivery of mutant LIGHT into tumor cells or other cells is not limited to a particular delivery method.

Biodegradable microspheres have also been used in gene delivery systems that encapsulate the nucleic acid. Microspheres such as matrices, films, gels and hydrogels which include hyaluronic acid (HA) derivatized with a dihydrazide and crosslinked to a nucleic acid forming slow release microspheres have been used to deliver nucleic acids. Controlled release gene delivery system utilizing poly(lactide-co-glycolide) (PLGA), hydroxypropylmethyl cellulose phthalate, cellulose acetate phthalate, and copolymer microspheres to encapsulate the gene vector are also known.

Therapeutic compositions used herein can be formulated into pharmaceutical compositions comprising a carrier suitable for the desired delivery method. Suitable carriers include materials that when combined with the therapeutic composition retain the anti-tumor function of the therapeutic composition. Examples include, but are not limited to a number of standard pharmaceutical carriers such as sterile phosphate buffered saline solutions, bacteriostatic water, and the like. Therapeutic formulations can be solubilized and administered via any route suitable to deliver the therapeutic composition to the tumor site. Potentially effective routes of administration include, but are not limited to, intravenous, parenteral, intraperitoneal, intramuscular, intratumor, intradermal, intraorgan, orthotopic, and the like. A formulation for intravenous injection comprises the therapeutic composition in a solution of preserved bacteriostatic water, sterile unpreserved water, and/or diluted in polyvinylchloride or polyethylene bags containing sterile sodium chloride for injection. Therapeutic protein preparations can be lyophilized and stored as sterile powders, preferably under vacuum, and then reconstituted in bacteriostatic water (containing for example, benzyl alcohol preservative) or in sterile water prior to injection. Dosages and administration protocols for the treatment of cancers using the methods disclosed herein may vary with the method and the target cancer, and generally depend on a number of factors appreciated and understood in the art.

Delivery using viral vectors. Viral vectors that contain nucleic acid sequences encoding mutant LIGHT are used for delivering nucleic acids. For example, a retroviral vector can be used. These retroviral vectors contain the components necessary for the correct packaging of the viral genome and integration into the host cell DNA. The nucleic acid sequences encoding the mutant LIGHT protein are cloned into one or more vectors, which facilitates delivery of the gene. Adenoviruses are suitable vehicles for delivering genes to various tissue targets including respiratory epithelia and other targets for adenovirus-based delivery systems are liver, the central nervous system, endothelial cells, and muscle. Adenoviral vectors are also suitable for targeting nucleic acid delivery to tumor cells. Adenoviruses have the advantage of being capable of infecting non-dividing cells. Adeno-associated virus (AAV) has also been proposed for use in gene delivery. Lentiviruses are also suitable vehicles for use in gene delivery.

Transfecting cells in tissue culture followed by delivery to patients. Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this method, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. The technique should provide for the stable transfer of the nucleic acid to the cell, so that the nucleic acid is expressible by the cell and preferably heritable and expressible by its cell progeny.

The resulting recombinant cells may be irradiated and can be delivered to a patient by various methods known in the art. Recombinant cells (e.g., hematopoietic stem or progenitor cells) are preferably administered intravenously. The amount of cells envisioned for use depends on the desired effect, patient state, etc., and can be determined by one skilled in the art. Cells into which a nucleic acid can be introduced for purposes of gene therapy encompass any desired, available cell type, and include but are not limited to epithelial cells, endothelial cells, keratinocytes, fibroblasts, muscle cells, hepatocytes, blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

Vaccines. As used herein, the term "vaccine" refers to a composition (e.g., a Mutant LIGHT antigen and an adjuvant) that elicits a tumor-specific immune response. These vaccines include prophylactic (preventing new tumors) and therapeutic (eradicating parental tumors). A vaccine vector such as a DNA vaccine encoding mutant LIGHT can be used to elicit immune response against tumors. The response is elicited from the subject's own immune system by administering the vaccine composition at a site (e.g., a site distant from the tumor). The immune response may result in the eradication of tumor cells in the body (e.g., both primary and metastatic tumor cells). Methods for generating tumor vaccines are well known in the art (See e.g., U.S. Pat. Nos. 5,994,523 and 6,207,147 each of which is herein incorporated by reference).

The vaccines may comprise one or more tumor antigens in a pharmaceutical composition. In some cases, the tumor antigen is inactivated prior to administration. In other embodiments, the vaccine further comprises one or more additional therapeutic agents (e.g., cytokines or cytokine expressing cells).

In certain cases, cells selected from a patient, such as fibroblasts, obtained, for example, from a routine skin biopsy, are genetically modified to express one or of the desired protein. Alternatively, patient cells that may normally serve as antigen presenting cells in the immune system such as macrophages, monocytes, and lymphocytes may also be genetically modified to express one or more of the desired antigens. The antigen expressing cells are then mixed with the patient's tumor cells (e.g., a tumor antigen), for example in the form of irradiated tumor cells, or alternatively in the form of purified natural or recombinant tumor antigen, and employed in immunizations, for example subcutaneously, to induce systemic anti-tumor immunity. The vaccines may be administered using any suitable method, including but not limited to, those described above.

Clonogenic assay. Clonogenic Assay for the Lung. Materials needed include DMEM 5% FCS (+p/s, HEPES); Collagenase type IV (Sigma); 60 µM 6-thioguanine; 50 ml conical tubes; 6 well tissue culture plates; 37° C. shaking incubator/tissue culture incubator; dissecting equipment: scissors, curved scissors, and forceps; 70 µm nylon cell strainers; ACK lysis; methanol; 0.03% (w/v) methylene blue solution. Preparation of collagenase medium has the following steps: to approx 25 ml medium per number of lung, add collagenase to make the medium 1.5 mg/ml concentration. To prepare a lung sample: (1) Remove lung from mouse and transfer it to a 6 well plate; 2) Add approx 200 µl of medium on the lung; 3) with curved scissors, mince the lung into small pieces; 4) use the curved portion of the closed scissors, transfer minced lung into a 50 ml conical tube 5 ml of collagenase medium; 5) add 5 ml of medium to the wells and pipette out and transfer the remaining lung pieces to the conical tube; 6) place in shaking incubator for 20 minutes at 37° C. at 175 r.p.m.; 7) pour the supernatant through a cell strainer into a clean 50 ml conical tube-any lung pieces on the cell strainer should return to the conical tube for a second digestion; 8) spin down at 1500 r.p.m. for 5 min in centrifuge; 9) discard supernatant after spinning down; 10) resuspend pellet in 1 ml of fresh collagenase free medium; 11) perform ACK lysis for 5 minutes; 12) count cells; 13) plate $3\times10^5$, $3\times10^4$, $3\times10^3$ cells into 12 well plate; 14) add 60 μM 6-thioguanine into each well; and 15) place plate in 37° C. tissue culture incubator, 5% $CO_2$ for 5-10 days.

Harvesting clonogenic metastatic colonies includes the following steps: (not necessary but easier to count colonies)—discard culture media from tissue culture plate; fix cells by adding 5 ml of methanol to each plate and swirl; and incubate at room temperature for 5 min (colonies should turn white); discard methanol and rinse each plate gently with 5 ml distilled water; (the cells should not come in contact with water until after the cells have been fixed); add 5 ml 0.03% (w/v) methylene blue solution to each plate; swirl to cover entire plate and incubate at room temperature for 5 min; discard dye and rinse plate gently with 5 ml distilled water; allow plate to air dry before counting blue colonies (one colony represents one clonogenic metastatic cells).

Mice and Cell Line. Female C3HXC57BL/6 F1 (C3B6F1), C57BL/6 and Balb/c mice, 4-8 weeks old were purchased from the National Cancer Institute, Frederick Cancer Research Facility (Frederick, Md.). 2C TCR transgenic mice on RAG-$1^{-/-}$/B6 background (2C mice) were provided by J. Chen (Massachusetts Institute of Technology, Boston, Mass.). OT-1 TCR transgenic mice on RAG-$1^{-/-}$/B6 background (OT-1 mice) were provided by A. Ma (The University of California at San Francisco). 2C and OT-1 mice were bred and maintained in the specific pathogen-free facility at the University of Chicago. Animal care and experiments were done in accordance with institutional and National Institutes of Health (NIH) guidelines and were approved by an animal use committee at the University of Chicago. The Ag104A fibrosarcoma expressing murine H-$2L^d$ (AG104-$L^d$) as described herein (see also Wick et al., 1997). B16-SIY melanoma cell line was generated as described in Blank et al., (2004). B16-OVA and 4T1 tumor, which is a 6-thioguanine-resistant cell line derived from a spontaneous mammary carcinoma, were both provided by Zhaoyang You, University of Pittsburgh. MC38 colon cancer cell line was provided by Y Liu (Ohio State University). Ag $104L^d$ and 4T1 tumor cells lines were grown in DMEM supplemented with 10% fetal calf serum (FCS). B16-OVA, B16-SIY and MC38 tumor cells were grown in RPMI supplemented with 10% fetal calf serum (FCS).

The generation of adenovirus-expressing mutant LIGHT. The mutant murine LIGHT (mmLIGHT) was generated as described herein. To construct recombinant mmLIGHT-Adenovirus, a BamH1/NotI fragment containing murine mutant LIGHT cDNA cut from pCDN3.1-mmLIGHT was cloned into the BamH/NotI sites of the first parental plasmid, pLEP-ubp (left end plasmid, Tetr) after human ubiquitin promoter (ubp). Subsequently, the pLEP-mmLIGHT was ligated to a second plasmid, pREP (right end plasmid, Ampr) at a unique intron-encoded Cla I site. The ligation product was packaged with λ phage packaging extracts. The pLEP/pREP hybrid cosmids were selected grown on Amp/Tet LB agar plate. Bgl II digestion was used to further identify recombinant cosmid containing insert mmLIGHT. The Adv-mmLIGHT DNA fragment was liberated from its recombinant cosmid by I-Ceu I digestion, and the mixture of I-CeuI digestion without further purification was transfected into 293 cells for recombinant adenovirus production (Adv-mmLIGHT).

Tumor injection, treatments and evaluation of metastases by colonogenic assay. For Ag104$L^d$ tumors, C3B6F1 mice were inoculated subcutaneously into the area around the tail base with the dose described in the results. For B16-SIY and MC38 tumors, B6 mice were inoculated subcutaneously into the area around the tail base with $10^6$ or $10^5$ tumor cells, respectively. For 4T1 tumors, Balb/c mice were inoculated subcutaneously into the area around the tail base or into the mammary fat pad with 105 tumor cells. The tumor nodules were inoculated with Ad-mutant LIGHT or Ad-control virus intratumorally in 50 μl PBS containing indicated amount of virus particles and p.f.u. For surgical excision of primary 4T1 tumors, mice were anesthetized before surgery, and tumors were resected with sterilized instruments. Wounds were closed with metallic clips. All mice survived surgery. Mice in which primary tumors recurred at the site of the surgical excision were eliminated from the experiments. For evaluation of metastases, lungs was collected and chopped before being dissociated in DMEM supplemented with 5% of FCS containing 1.5 mg/ml collagenase type 4 (Sigma) for 30 minutes in 37° C. shaking incubator at 178 rpm speed. Organs were then plated at various dilutions in the DMEM supplemented with 10% FCS and 60 μM 6-thioguanine. Individual colonies representing micrometastasis were counted after 5-10 days.

In vitro infection and vaccination with irradiated tumor cells. $1\times10^6$ cells were plated in 100 mm cell culture dish for 24 hours then infected with Ad-Control or Ad-mutant LIGHT at $4\times10^8$ p.f.u./ml for 24 hours. Cells were harvested and checked for mutant LIGHT expression by FACS staining with LTβR-Ig at 0.02 mg/mL followed by PE-coupled donkey anti-human IgG (Jackson, West grove, Pa.). For vaccination, tumor cells harvested after infection and confirmed for mutant LIGHT expression were irradiated at 1500 rads prior to subcutaneous injection into the mammary fat pad. All infections were performed in an approved biohazard hood.

Analysis of Cells by FACS. In order to detect mutant LIGHT expression on the tumor cells, Ag104$L^d$, B16-OVA, B16-SIY, MC38 and 4T1 tumor cells infected with Ad-mutant LIGHT were incubated with LTβR-Ig at 0.02 mg/mL followed by PE-coupled donkey anti-human IgG (Jackson, West grove, Pa.). For detection of proliferation and expression of CD44 and IFN-γ by CFSE-labeled 2C T cells, isolated lymph node (LN) cells, splenocytes, and tumor-infiltrating T cells (TIL) were stained as described herein (see also Yu et al., 2003, 2005). Samples were examined on a FACScan and data was analyzed with FlowJo softwares (Becton Dickinson, Franklin Lakes, N.J.).

Measurement of cytokines in the spleen and tumor. We prepared tumor and spleen homogenates as described (Yu et al., 2003). Briefly, comparable amounts of tumor or spleen tissues were collected, weighed and homogenized in PBS containing protease inhibitors, and the supernatants were collected by centrifugation. The amount of cytokines in the supernatants was quantified using the cytometric bead array kit (CBA) (BD Biosciences) on a FACS Caliber cytometer equipped with CellQuestPro and CBA software (Becton Dickinson) according to manufacture's instruction.

Adoptive Transfer of 2C T Cells. LN cells and splenocytes were isolated from 2C mice and $CD8^+$ T cells were negatively selected with a $CD8^+$ T cell enrichment kit (Miltenyi Biotec, Auburn, Calif.). When analyzed, >90% of the enriched $CD8^+$ cells expressed the 2C receptor. Approximately 3×10⁶ 2C T cells were transferred into OT-1 mice for assays of tumor growth. The same number of 2C T cells was transferred to each mouse in each experiment. To transfer CFSE-labeled T cells, T cells were labeled with CFSE as described herein (see also Yu et al., 2003). 3×10⁶ CFSE-labeled T cells were injected intravenously into the retro-orbital plexus in a 0.2-ml volume to the tumor-bearing mice. Cells were isolated from the inguinal lymph nodes (DLNs), the other lymph nodes (nondraining lymph nodes (NDLN)), spleen (SPL) or tumors at the time indicated.

Cell Isolation from tumor tissue. The mice were first bled to decrease the blood contamination of tumor tissue. The tumor tissues were collected, washed in the PBS, cut into pieces, and resuspended in DMEM supplemented with 5% FCS and 1.5 mg/ml collagenase D (collagenase D solution) for 40 min in a 37° C. shaking incubator. The single cell suspension was collected after 40 min, and the cell clumps were digested for another 40 min in the collagenase D solution until all tumor tissue had resolved into a single cell suspension.

Statistical analysis for difference in tumor growth. Because the tumor growth was observed repeatedly over time on the same mouse, the random effect models for longitudinal data were used to analyze such data. For each experiment, the tumor growth was assumed to depend on treatment and to follow a linear growth rate over time. The model gave an overall estimate of the intercept and slope of the linear growth for each group. Both the intercept and slope were allowed to vary among individual mouse. The slope, i.e., the growth rate was compared was different among different treatment groups. Because the actual tumor growth may not follow a linear growth trend over the entire follow up period. The increase of tumor growth was slow at the early stage and became rapid at the later stage in some experiments. A quadratic term was added to the follow-up time in the above random effect models.

Wild type human LIGHT DNA sequence (SEQ ID NO: 14) (sequence encoding a protease site EQLI (SEQ ID NO: 17) is shown in bold):

```
ATGGAGGAGAGTGTCGTACGGCCCTCAGTGTTTGTGGTGGATGGAC

AGACCGACATCCCATTCACGAGGCTGGGACGAAGCCACCGGAGACAGTCG

TGCAGTGTGGCCCGGGTGGGTCTGGGTCTCTTGCTGTTGCTGATGGGGC

TGGGCTGGCCGTCCAAGGCTGGTTCCTCCTGCAGCTGCACTGGCGTCTAG

GAGAGATGGTCACCCGCCTGCCTGACGGACCTGCAGGCTCCTGGGAGCAG

CTGATACAAGAGCGAAGGTCTCACGAGGTCAACCCAGCAGCGCATCTCAC
```

```
AGGGGCCAACTCCAGCTTGACCGGCAGCGGGGGGCCGCTGTTATGGGAGA

CTCAGCTGGGCCTGGCCTTCCTGAGGGGCCTCAGCTACCACGATGGGGCC

CTTGTGGTCACCAAAGCTGGCTACTACTACATCTACTCCAAGGTGCAGCT

GGGCGGTGTGGGCTGCCCGCTGGGCCTGGCCAGCACCATCACCCACGGCC

TCTACAAGCGCACACCCCGCTACCCCGAGGAGCTGGAGCTGTTGGTCAGC

CAGCAGTCACCCTGCGGACGGGCCACCAGCAGCTCCCGGGTCTGGTGGGA

CAGCAGCTTCCTGGGTGGTGTGGTACACCTGGAGGCTGGGGAGAAGGTGG

TCGTCCGTGTGCTGGATGAACGCCTGGTTCGACTGCGTGATGGTACCCGG

TCTTACTTCGGGGCTTTCATGGTGTGA-3'
```

Native human LIGHT amino acid sequence (SEQ ID NO: 15) (protease digestion site is bold underlined):

```
MEESVVRPSVFVVDGQTDIPFTRLGRSHRRQSCSVARVGLGLLLLL

MGAGLAVQGWFLLQLHWRLGEMVTRLPDGPAGSWEQLIQERRSHEVNPAA

HLTGANSSLTGSGGPLLWETQLGLAFLRGLSYHDGALVVTKAGYYYIYSK

VQLGGVGCPLGLASTITHGLYKRTPRYPEELELLVSQQSPCGRATSSSRV

WWDSSFLGGVVHLEAGEKVVVRVLDERLVRLRDGTRSYFGAFMV
```

One aspect of a mutant human LIGHT amino acid sequence (SEQ ID NO: 16) (EQLI (SEQ ID NO: 17) is absent, indicated by dots):

```
MEESVVRPSVFVVDGQTDIPFTRLGRSHRRQSCSVARVGLGLLLLLMGAG

LAVQGWFLLQLHWRLGEMVTRLPDGPAGSW . . . QERRSHEVNPAAH

LTGANSSLTGSGGPLLWETQLGLAFLRGLSYHDGALVVTKAGYYYIYSKV

QLGGVGCPLGLASTITHGLYKRTPRYPEELELLVSQQSPCGRATSSSRVW

WDSSFLGGVVHLEAGEKVVVRVLDERLVRLRDGTRSYFGAFMV
```

Codon optimized nucleotide sequence for mouse mutant LIGHT, starting ATG is highlighted in bold: (SEQ ID NO: 18)

```
  1 GGGCGAATTGGGTACCGGATCCGCGACCATGGAGAGCGTGGTGCAGCCCAGCGTGTTCGT
    ---------+---------+---------+---------+---------+---------+

61 GGTGGACGGCCAGACCGACATCCCCTTCAGGAGGCTGGAGCAGAACCACAGGCGGAGGAG
    ---------+---------+---------+---------+---------+---------+

121 ATGTGGCACCGTGCAGGTGTCCCTGGCCCTGGTGCTGCTGCTGGGCGCTGGCCTGGCCAC
    ---------+---------+---------+---------+---------+---------+

181 CCAGGGCTGGTTTCTGCTGAGGCTGCACCAGAGGCTGGGCGACATCGTGGCCCACCTGCC
    ---------+---------+---------+---------+---------+---------+

241 CGATGGCGGCAAGGGCAGCTGGCAGGACCAGAGGAGCCACCAGGCCAACCCTGCCGCCCA
    ---------+---------+---------+---------+---------+---------+
```

-continued

```
301 CCTGACAGGCGCCAACGCCAGCCTGATCGGCATCGGCGGACCCCTGCTGTGGGAGACCAG
    ---------+---------+---------+---------+---------+---------+

361 GCTGGGCCTGGCTTTCCTGAGGGGCCTGACCTACCACGACGGCGCCCTGGTGACCATGGA
    ---------+---------+---------+---------+---------+---------+

421 GCCCGGCTACTACTACGTGTACAGCAAGGTGCAGCTGTCCGGAGTGGGCTGCCCTCAGGG
    ---------+---------+---------+---------+---------+---------+

481 CCTGGCCAACGGCCTGCCCATCACCCACGGCCTGTACAAGAGGACCAGCAGATACCCCAA
    ---------+---------+---------+---------+---------+---------+

541 GGAGCTGGAGCTGCTGGTCTCCAGGCGGAGCCCCTGTGGCAGGGCCAACAGCAGCCGAGT
    ---------+---------+---------+---------+---------+---------+

601 GTGGTGGGACAGCAGCTTCCTGGGCGGCGTGGTGCACCTGGAGGCCGGCGAGGAGGTGGT
    ---------+---------+---------+---------+---------+---------+

661 GGTGAGGGTGCCCGGCAACAGGCTGGTGAGGCCCAGGGACGGCACCAGGAGCTACTTCGG
    ---------+---------+---------+---------+---------+---------+

721 CGCCTTCATGGTGTGATGAGCGGCCGCGAGCTCCAGCTTTTGTTCCC
    ---------+---------+---------+---------+-------
```

Codon optimized nucleotide sequence for human mutant LIGHT, starting ATG is highlighted in bold. (SEQ ID NO: 19)

```
GAATTCGAGCTCGGTACCCGAGACGGTACCGGATCCGCCACCATGGAGGAGAGCGTTGTG
AGGCCCAGCGTGTTCGTGGTGGACGGCCAGACCGACATCCCCTTCACCCGGCTGGGCCGG
AGCCACCGGAGGCAGAGCTGCTCCGTGGCCAGAGTGGGGCTGGGCCTGCTGCTCCTGCTG
ATGGGAGCCGGCCTGGCCGTGCAGGGCTGGTTCCTGCTGCAGCTGCACTGGCGGCTGGGC
GAGATGGTGACCCGGCTGCCCGATGGCCCTGCCGGCAGCTGGCAGGAGCGGCGGAGCCAC
GAGGTGAACCCTGCCGCCCACCTGACCGGCGCCAACAGCAGCCTGACCGGCAGCGGCGGA
CCCCTGCTGTGGGAGACCCAGCTGGGCCTGGCCTTCCTGAGGGGCCTGAGCTACCACGAC
GGCGCCCTGGTGGTGACCAAGGCCGGCTACTACTACATCTACAGCAAGGTGCAGCTGGGC
GGAGTGGGCTGCCCTCTGGGGCTGGCCAGCACCATCACCCACGGCCTGTACAAGCGGACC
CCCAGATACCCCGAGGAGCTGGAGCTGCTGGTGTCCCAGCAGAGCCCCTGTGGCAGGGCC
ACCTCCAGCAGCCGGGTGTGGTGGGACAGCAGCTTCCTGGGCGGCGTGGTGCACCTGGAG
GCCGGCGAGAAAGTGGTTGTGAGGGTGCTGGACGAGCGGCTTGTGAGGCTGAGGGACGGC
ACCCGGAGCTACTTCGGCGCCTTCATGGTGTGATGAGCGGCCGCGAGCTCGTCTCGGGGA
TCCTCTAGAGTCGACCTGCAGGCATGCAAGCTTG
```

Generation of mutant LIGHT Expression Vectors and Clones pcDNA3.1-LIGHT was used as template to generate two dsDNA fragments A and B by PCR. For generation of fragment A (~500 b.p.), sense primer 5'-CATGGATCCAA-GACCATGGAGAGTGTGGTACA-3' (SEQ ID NO: 20) (the bold text indicated BamHI site) and antisense primer 5'-AG-ATCGTTGATCTTGCCAGGAGCCTTTGCC-3' (SEQ ID NO: 21) were used. To generate fragment B (~200 b.p.), sense primer 5'-GGCAAAGGCTCCTGGCAAGATCAAC-GATCT-3' (SEQ ID NO: 22) and antisense primer 5'-AC-CTCTAGATCAGACCATGAAAGCTCCGA-3' (SEQ ID NO: 23) (the underlined text indicated XbaI site) were used. The antisense primer for fragment A is complimentary with sense primer for fragment B, which covers sequences for amino acid (a.a.) 73-87 among which a.a. 79-82 were deleted. Fragments A and B were mixed, denatured at 94° C. and cooled down to room temperature to anneal the two DNA fragments. The annealed DNA product was used as template for a PCR reaction and the product was cloned into pcDNA3.1 using BamHI and XbaI. The deletion of a.a. 79-82 was verified by sequencing. To generate pMFG-mutant LIGHT, pcDNA3.1-mutant LIGHT was digested with NcoI and BamHI and ligated to a NcoI and BamHI-digested the pMFG-S-TPA plasmid (Mulligan RC, Massachusetts Institute of Technology, Boston, MA).

PUBLICATIONS CITED

The publications cited are incorporated by reference to the extent they relate to the present invention.

Ali et al., *Gene Therapy* 1: 367-384 (1994).
Anderson, *Science* 256: 808-813 (1992).
Armentano et al., *J. Virol.* 71: 2408-2416 (1997).
Berkner et al., *Curr. Top. Microbiol. Immunol.* 158: 39-61 (1992).

Blank et al., PD-L1/B7H-1 inhibits the effector phase of tumor rejection by T cell receptor (TCR) transgenic CD8+ T cells. *Cancer Res* 64: 1140-1145 (2004).

Boon, T. & van der Bruggen, P. Human tumor antigens recognized by T lymphocytes. *J. Exp. Med.* 183, 725-29 (1996).

Boyce, et al., *PNAS* 93: 2348-2352 (1996).

Brandyopadhyay et al., *Mol. Cell. Biol.* 4: 749-754 (1984).

Cannon, R. E. et al. Induction of transgene expression in Tg.AC(v-Ha-ras) transgenic mice concomitant with DNA hypomethylation. *Mol Carcinog* 21, 244-50 (1998).

Carter, "The Growth Cycle of Adeno-Associated Virus," in *Handbook of Parvoviruses*, vol. 1, pp. 155-168, Tijssen, ed., CRC Press (1990).

Chen, L., Linsley, P. S. & Hellstrom, K. E. Costimulation of T cells for tumor immunity. *Immunol Today* 14, 483-6. (1993).

Chen et al., *Proc. Nat. Acad. Sci. USA* 94: 1645-1650 (1997).

Cyster, J. G. Chemokines and cell migration in secondary lymphoid organs. *Science* 286, 2098-102. (1999).

Dougall, W. C. et al. RANK is essential for osteoclast and lymph node development. *Genes Dev* 13, 2412-24. (1999).

Engelhardt et al., *Hum. Gene Ther.* 5: 1217-1229 (1994).

Ettinger, R. The role of tumor necrosis factor and lymphotoxin in lymphoid organ development. *Curr Top Microbiol Immunol* 251, 203-10 (2000).

Fu, Y. X. & Chaplin, D. D. Development and maturation of secondary lymphoid tissues. *Annu Rev Immunol* 17, 399-433 (1999).

Glorioso et al., *Nature Med* 7: 33-40 (2001).

Golasten et al., *New Engl. J. Med.* 309: 288-296 (1983).

Hofmann, et al., *PNAS* 92: 10099-10103 (1995).

Hu and Pathak, *Pharmacol Rev.* 52: 493-512 (2000).

Ishibashi et al., *J. Clin. Invest.* 92: 883-893 (1993).

Ishibashi et al., *J. Clin. Invest.* 93: 1889-1893 (1994).

Jooss et al., *Hum Gene Ther.* 7: 1555-1566 (1996).

Kang, H. S. et al. Signaling via LTbetaR on the lamina propria stromal cells of the gut is required for IgA production. *Nat Immunol* 3, 576-82 (2002).

Kay et al., *Pro. Nat. Acad. Sci. USA* 94: 4686-4691.

Kim, D. et al. Regulation of peripheral lymph node genesis by the tumor necrosis factor family member TRANCE. *J Exp Med* 192, 1467-78. (2000).

Kong, Y. Y. et al. Activated T cells regulate bone loss and joint destruction in adjuvant arthritis through osteoprotegerin ligand. *Nature* 402, 304-9. (1999).

Kuriyama et al., *Hum. Gene Ther.* 11: 2219-2230 (2000).

Leder, A., Kuo, A., Cardiff, R. D., Sinn, E. & Leder, P. v-Ha-ras transgene abrogates the initiation step in mouse skin tumorigenesis: effects of phorbol esters and retinoic acid. *Proc. Natl. Acad. Sci. U.S.A.* 87, 9178-82 (1990).

Mauri, D. N. et al. LIGHT, a new member of the TNF superfamily, and lymphotoxin alpha are ligands for herpesvirus entry mediator. *Immunity* 8, 21-30. (1998).

Madzak et al., *J. Gen. Virol.* 73: 1533 36 (1992)

Melero, I. et al. Monoclonal antibodies against the 4-1BB T-cell activation molecule eradicate established tumors. *Nat Med* 3, 682-5. (1997).

Miller, *Curr. Top. Microbiol. Immunol.* 158: 1-24 (1992).

Miller et al., *Nature* 357: 455-450 (1992)

Moss et al., Curr. Top. *Microbiol. Immunol.* 158: 25 38 (1992).

Margulskee, *Curr. Top. Microbiol. Immunol.* 158: 67-93 (1992).

Muzyczka, *Curr. Top. Microbiol. Immunol.* 158: 97-123 (1992).

Ochsenbein, A. F. et al. Roles of tumour localization, second signals and cross priming in cytotoxic T-cell induction. *Nature* 411, 1058-64. (2001).

Ostrand-Rosenberg, S. et al. Cell-based vaccines for the stimulation of immunity to metastatic cancers. *Immunol Rev* 170, 101-14. (1999).

Peace, D. J. et al. Lysis of ras oncogene-transformed cells by specific cytotoxic T lymphocytes elicited by primary in vitro immunization with mutated ras peptide. *J Exp Med* 179, 473-9 (1994).

Rooney, I. A. et al. The lymphotoxin-beta receptor is necessary and sufficient for LIGHT-mediated apoptosis of tumor cells. *J Biol Chem* 275, 14307-15. (2000).

Rosenberg, S. A. Progress in human tumour immunology and immunotherapy. *Nature* 411, 380-4. (2001).

Ruddle, N. H. Lymphoid neo-organogenesis: lymphotoxin's role in inflammation and development. *Immunol Res* 19, 119-25 (1999).

Sarma, S. et al. Cytotoxic T lymphocytes to an unmutated tumor rejection antigen P1A: normal development but restrained effector function in vivo. *J Exp Med* 189, 811-20. (1999).

Schreiber, H. Tumor Immunology. in *Fundamental Immunology* (ed. Paul, W. E.) 1247-1280 (Lippincott Raven Press, New York, 1999).

Schieder et al., *Nature Genetics* 18: 180-183 (1998).

Sha, W. C. et al. Selective expression of an antigen receptor on CD8-bearing T lymphocytes in transgenic mice. *Nature* 335, 271-4 (1988).

Somia and Verma, *Nature Rev.* 1: 91-99 (2000).

Tamada, K. et al. Modulation of T-cell-mediated immunity in tumor and graft-versus-host disease models through the LIGHT co-stimulatory pathway. *Nat Med* 6, 283-9. (2000).

Tanzawa et al., *FEBS Letters* 118(1): 81-84 (1980).

van Beusechem et al., *Gene Ther.* 7: 1940-1946 (2000).

Wang, J. et al. The complementation of lymphotoxin deficiency with LIGHT, a newly discovered TNF family member, for the restoration of secondary lymphoid structure and function. *Eur J Immunol* 32: 1969 (2002).

Wang, J. et al. The regulation of T cell homeostasis and autoimmunity by T cell derived LIGHT. *J. Clinic. Invest.* 108:1771-1780 (2001).

Watanabe, *Atherosclerosis* 36: 261-268 (1986).

Wick, M. et al. Antigenic cancer cells grow progressively in immune hosts without evidence for T cell exhaustion or systemic anergy. *J Exp Med* 186, 229-38. (1997).

Wilson, *Nature* 365: 691-692 (1993).

Wu, Q. et al. The requirement of membrane lymphotoxin for the presence of dendritic cells in lymphoid tissues. *J Exp Med* 190, 629-38 (1999).

Ye, Q. et al. Modulation of LIGHT-HVEM costimulation prolongs cardiac allograft survival. *J Exp Med* 195, 795-800. (2002).

Ye, Z. et al. Gene therapy for cancer using single-chain Fv fragments specific for 4-1BB. *Nat Med* 8, 343-8. (2002).

Yu, P. et al., Complementary role of CD4+ T cells and secondary lymphoid tissues for cross-presentation of tumor antigen to CD8+ T cells. *J Exp Med* 197:985-995 (2003).

P. et al., Intratumor depletion of CD4+ cells unmasks tumor immunogenicity leading to the rejection of late-stage tumors. *J Exp Med* 201: 779-791 (2005).

Zhai, Y. et al. LIGHT, a novel ligand for lymphotoxin beta receptor and TR2/HVEM induces apoptosis and suppresses in vivo tumor formation via gene transfer. *Journal of Clinical Investigation* 102, 1142-51 (1998).

Zinkernagel, R. M. Immunity against solid tumors? *Int J Cancer* 93, 1-5. (2001).
U.S. Pat. No. 6,048,551
U.S. Pat. No. 5,436,146
U.S. Pat. No. 4,980,286
U.S. Pat. No. 5,994,523
U.S. Pat. No. 6,207,147
U.S. Pat. No. 4,797,368
U.S. Pat. No. 5,399,346

---

We claim

1. A method of reducing tumor burden, the method comprising:
   (a) introducing a mutant human LIGHT (homologous to lymphotoxin, exhibits inducible expression, and competes with HSV glycoprotein D for herpes virus entry mediator, a receptor expressed by T lymphocytes) protein or a fragment comprising an extracellular domain of native LIGHT into a tumor site, wherein the mutant LIGHT protein or the LIGHT fragment is resistant to protease digestion and is stably present on the tumor cell surface, wherein the mutant LIGHT has an amino acid change in a proteolytic site comprising an amino acid sequence EQLI (SEQ ID NO: 17) from positions 81-84 of native LIGHT protein, or does not have the proteolytic site; and
   (b) reducing tumor burden by stimulating activation of tumor-specific T-cells against the tumor by the stable presence of protease resistant mutant LIGHT.

2. The method of claim 1, wherein the mutant LIGHT protein is introduced directly into the tumor site.

3. The method of claim 1, wherein the mutant LIGHT protein is introduced adjacent to the tumor site.

4. The method of claim 1, wherein the tumor burden is reduced by stimulation of cytotoxic T-lymphocytes.

5. The method of claim 1, wherein the tumor burden is reduced by stimulation of production of chemokines, adhesion molecules, and costimulatory molecules for priming naïve T-cells.

6. The method of claim 1 wherein the tumor burden measured is metastastic disease.

7. The method of claim 1, wherein the mutant LIGHT protein or a fragment comprising the extracellular domain of native LIGHT is expressed on the tumor cell surface following introduction of a nucleic acid molecule.

8. A method of reducing tumor burden, the method comprising:
   (a) introducing a mutant human LIGHT (homologous to lymphotoxin, exhibits inducible expression, and competes with HSV glycoprotein D for herpes virus entry mediator, a receptor expressed by T lymphocytes) fragment comprising an extracellular domain of native LIGHT wherein the extracellular domain of native LIGHT comprises SEQ ID NO: 1 in which one or more of the amino acids EQLI (SEQ ID NO: 17) from positions 81-84 of native LIGHT protein, is either deleted or mutated, into a tumor site, wherein the mutant LIGHT fragment is resistant to protease digestion and is stably present on the tumor cell surface; and
   (b) reducing tumor burden by stimulating activation of tumor-specific T-cells against the tumor by the stable presence of protease resistant mutant LIGHT.

* * * * *

UNITED STATES PATENT AND TRADEMARK OFFICE
CERTIFICATE OF CORRECTION

PATENT NO. : 7,811,983 B2  
APPLICATION NO. : 11/500177  
DATED : October 12, 2010  
INVENTOR(S) : Yang-Xin Fu et al.

Page 1 of 1

It is certified that error appears in the above-identified patent and that said Letters Patent is hereby corrected as shown below:

In Column 59, Claim 1, Line 43,
"LIGIIT" should read --LIGHT--.

Signed and Sealed this
Fifteenth Day of March, 2011

David J. Kappos
*Director of the United States Patent and Trademark Office*

UNITED STATES PATENT AND TRADEMARK OFFICE
CERTIFICATE OF CORRECTION

PATENT NO. : 7,811,983 B2  
APPLICATION NO. : 11/500177  
DATED : October 12, 2010  
INVENTOR(S) : Yang-Xin Fu It is certified that error appears in the above-identified patent and that said Letters Patent is hereby corrected as shown below:

In the Claims

Please amend claim 6 as follows:

col. 60, line 40, delete the word "metastastic" and insert in its place the word --metastatic--

Signed and Sealed this
Twenty-fourth Day of December, 2013

Margaret A. Focarino
*Commissioner for Patents of the United States Patent and Trademark Office*